United States Patent
Hess-Stumpp et al.

(10) Patent No.: US 6,780,594 B2
(45) Date of Patent: Aug. 24, 2004

(54) METHOD FOR IN VITRO DIAGNOSIS OF ENDOMETRIOSIS

(75) Inventors: Holger Hess-Stumpp, Berlin (DE); Bernard Haendler, Berlin (DE); Joern Kraetzschmar, Berlin (DE); Berrholt Kreft, Berlin (DE); Elke Winterhager, Essen (DE); Pedro Regidor, Essen (DE); Simone Scotti, Hattingen (DE)

(73) Assignee: Schering Aktiengesellschaft, Berlin (DE)

(*) Notice: Subject to any disclaimer, the term of this patent is extended or adjusted under 35 U.S.C. 154(b) by 0 days.

(21) Appl. No.: 09/961,403

(22) Filed: Sep. 25, 2001

(65) Prior Publication Data

US 2003/0077589 A1 Apr. 24, 2003

Related U.S. Application Data

(60) Provisional application No. 60/243,265, filed on Oct. 26, 2000.

(30) Foreign Application Priority Data

Sep. 25, 2000 (DE) .......................................... 100 48 633

(51) Int. Cl.[7] .......................... C12Q 1/68; C07H 21/02; C07H 21/04
(52) U.S. Cl. .......................... 435/6; 536/23.1; 536/24.3
(58) Field of Search ............................ 435/6; 536/23.1, 536/24.3

(56) References Cited

U.S. PATENT DOCUMENTS

| | | | |
|---|---|---|---|
| 5,478,725 A | * | 12/1995 | Lessey |
| 5,843,673 A | * | 12/1998 | Sharpe-Timms |
| 6,033,860 A | | 3/2000 | Lockhart et al. |
| 6,121,230 A | * | 9/2000 | Charnock-Jones et al. |
| 6,376,201 B2 | * | 4/2002 | Miron et al. |
| 6,387,629 B1 | * | 5/2002 | Schneider et al. |

FOREIGN PATENT DOCUMENTS

| | | |
|---|---|---|
| DE | 19824230 A1 | 12/1999 |
| WO | WO 9513821 A | 5/1995 |
| WO | WO 9935293 A | 7/1999 |
| WO | WO 99/50456 | 10/1999 |

OTHER PUBLICATIONS

Kennedy et al., "The Genetics of Endometriosis," *Journal of Reproductive Medicine*, (Mar. 1998), vol. 43, No. 3, Suppl pp. 263–268.

Spitsyn et al., "Genetic aspects of endometriosis: Preculiarities of the distribution of polymorphic gene frequency," *Genetika*, (1996) vol. 32, No. 12, pp. 1693–1699.

Poropatich et al., "MSN–1 Antibody in the evelution of femal genital tract Adenocarcinomas", *Int. j. Gynecol Pathol.* (1990), 9 (1), pp. 73–79.

Zhu et al., "Cellular gene expression altered by human cytomegalovirus: Global monitoring with oligonucleotide arrays," *Proc. Natl. Acad. Sci.* USA, vol. 95, pp 14470–14475, Nov. 1998, Microbiology.

Kauma et al. "Production of Fibronectin by Peritoneal Macrophages and bConcentration of Fibronectin in Peritoneal Fluid From Patients with or Wiithout Endometriosis," Database accession No. PREV198886075193, Bd. 72, Nr. 1, 1988, pp. 13–18.

* cited by examiner

*Primary Examiner*—Ethan Whisenant
(74) *Attorney, Agent, or Firm*—Millen, White, Zelano & Branigan, P.C.

(57) ABSTRACT

The invention relates to a method for diagnosis of endometriosis, whereby the amount of gene product of at least one gene from the group that consists of fibronectin, insulin-like growth factor binding protein-2, transmembrane receptor PTK7, platelet-derived growth factor receptor alpha, collagen type XVIII alpha 1, subtilisin-like protein (PACE4), laminin M chain (merosin), elastin, collagen type IV alpha 2, p27 interferon alpha-inducible gene, reticulocalbin, aldehyde dehydrogenase 6, gravin, nidogen and phospholipase C epsilon is determined in a patient sample.

11 Claims, 15 Drawing Sheets

| Data Bank No., Name | Comparison of Endometriosis versus Normal (Secr. Phase) | Comparison of Endometriosis versus Normal (Prol. Phase) | Comparison of Secr. versus Prol. Phase (Endometrium) |
|---|---|---|---|
| X02761, fibronectin (FN precursor) | down (0 up - 16 down) | down (4 up -12 down) | up (18 up - 1 down) |
| S37730, insulin-like growth factor binding protein-2 | down (1-15) | nc (13-13) | up (17-2) |
| U40271, Human transmembrane receptor precursor (PTK7) | down (0-14) | nc (6-2) | up (9-1) |
| M21574, platelet-derived growth factor receptor alpha (PDGFRA) | down (0-13) | nc (8-10) | up (17-0) |
| L22548, collagen type XVIII alpha 1 (COL18A1) | down (0-13) | down (0-8) | up (17-0) |
| M80482, subtilisin-like protein (PACE4) | down (1-13) | down (4-13) | up (22-2) |
| Z26653, laminin M chain (merosin) | down (1-13) | nc (9-10) | up (17-1) |
| M36860, U77846, Elastin | down (0-12) | nc (0-0) | up (25-0) |
| X05610, type IV collagen alpha -2 chain | down (0-12) | nc (3-3) | up (11-0) |
| X67325, p27 interferon alpha-inducible gene | down (1-12) | nc (9-10) | up (10-2) |

Figure 1a

| Data Bank No., Name | Comparison of Endometriosis versus Normal (Secr. Phase) | Comparison of Endometriosis versus Normal (Prol. Phase) | Comparison of Secr. versus Prol. Phase (Endometrium) |
|---|---|---|---|
| D42073, reticulocalbin | down (0-11) | nc (8-5) | up (11-2) |
| U07919, aldehyde dehydrogenase 6 | down (1-11) | nc (13-9) | up (22-0) |
| U81607, gravin | down (1-11) | nc (8-7) | up (18-1) |
| M30269, nidogen | down (0-10) | nc (8-14) | up (15-3) |
| D42108, phospholipase C Epsilon | down (1-10) | nc (12-14) | up (25-0) |

| Seq.IDNO | Name | Protein Sequence |
|---|---|---|
| 1 | Fibronectin | MLRGPGPGLL LLAVQCLGTA VPSTGASKSK RQAQQMVQPQ SPVAVSQSKP GCYDNGKHYQ INQQWERTYL GNALVCTCYG GSRGFNCESK PEAEETCFDK YTGNTYRVGD TYERPKDSMI WDCTCIGAGR GRISCTIANR CHEGGQSYKI GDTWRRPHET GGYMLECVCL GNGKGEWTCK PIAEKCFDHA AGTSYVVGET WEKPYQGWMM VDCTCLGEGS GRITCTSRNR CNDQDTRTSY RIGDTWSKKD NRGNLLQCIC TGNGRGEWKC ERHTSVQTTS SGSGPFTDVR AAVYQPQPHP QPPPYGHCVT DSGVVYSVGM QWLKTQGNKQ MLCTCLGNGV SCQETAVTQT YGGNSNGEPC VLPFTYNGRT FYSCTTEGRQ DGHLWCSTTS NYEQDQKYSF CTDHTVLVQT QGGNSNGALC HFPFLYNNHN YTDCTSEGRR DNMKWCGTTQ NYDADQKFGF CPMAAHEEIC TTNEGVMYRI GDQWDKQHDM GHMMRCTCVG NGRGEWTCIA YSQLRDQCIV DDITYNVNDT FHKRHEEGHM LNCTCFGQGR GRWKCDPVDQ CQDSETGTFY QIGDSWEKYV HGVRYQCYCY GRGIGEWHCQ PLQTYPSSSG PVEVFITETP SQPNSHPIQW NAPQPSHISK YILRWRPKNS VGRWKEATIP GHLNSYTIKG LKPGVVYEGQ LISIQQYGHQ EVTRFDFTTT STSTPVTSNT VTGETTPFSP LVATSESVTE ITASSFVVSW VSASDTVSGF RVEYELSEEG DEPQYLDLPS TATSVNIPDL LPGRKYIVNV YQISEDGEQS LILSTSQTTA PDAPPDPTVD QVDDTSIVVR WSRPQAPITG YRIVYSPSVE GSSTELNLPE TANSVTLSDL QPGVQYNITI YAVEENQEST PVVIQQETTG TPRSDTVPSP RDLQFVEVTD VKVTIMWTPP ESAVTGYRVD VIPVNLPGEH GQRLPISRNT FAEVTGLSPG VTYYFKVFAV SHGRESKPLT AQQTTKLDAP TNLQFVNETD STVLVRWTPP RAQITGYRLT VGLTRRGQPR QYNVGPSVSK YPLRNLQPAS EYTVSLVAIK GNQESPKATG VFTTLQPGSS IPPYNTEVTE TTIVITWTPA PRIGFKLGVR PSQGGEAPRE VTSDSGSIVV SGLTPGVEYV YTIQVLRDGQ ERDAPIVNKV VTPLSPPTNL HLEANPDTGV LTVSWERSTT PDITGYRITT TPTNGQQGNS LEEVVHADQS SCTFDNLSPG LEYNVSVYTV KDDKESVPIS DTIIPAVPPP TDLRFTNIGP DTMRVTWAPP PSIDLTNFLV RYSPVKNEED VAELSISPSD NAVVLTNLLP GTEYVVSVSS VYEQHESTPL RGRQKTGLDS PTGIDFSDIT ANSFTVHWIA PRATITGYRI RHHPEHFSGR PREDRVPHSR NSITLTNLTP GTEYVVSIVA LNGREESPLL IGQQSTVSDV PRDLEVVAAT PTSLLISWDA |

Figure 2b

| Seq.IDNO | Name | Protein Sequence |
|---|---|---|
|  |  | PAVTVRYRI TYGETGGNSP VQEFTVPGSK STATISGLKP GVDYTITVYA VTGRGDSPAS SKPISINYRT EIDKPSQMQV TDVQDNSISV KWLPSSSPVT GYRVTTTPKN GPGPTKTKTA GPDQTEMTIE GLQPTVEYVV SVYAQNPSGE SQPLVQTAVT NIDRPKGLAF TDVDVDSIKI AWESPQGQVS RYRVTYSSPE DGIHELFPAP DGEEDTAELQ GLRPGSEYTV SVVALHDDME SQPLIGTQST AIPAPTDLKF TQVTPTSLSA QWTPPNVQLT GYRVRVTPKE KTGPMKEINL APDSSSVVVS GLMVATKYEV SVYALKDTLT SRPAQGVVTT LENVSPPRRA RVTDATETTI TISWRTKTET ITGFQVDAVP ANGQTPIQRT IKPDVRSYTI TGLQPGTDYK IYLYTLNDNA RSSPVVIDAS TAIDAPSNLR FLATTPNSLL VSWQPPRARI TGYIIKYEKP GSPPREVVPR PRPGVTEATI TGLEPGTEYT IYVIALKNNQ KSEPLIGRKK TDELPQLVTL PHPNLHGPEI LDVPSTVQKT PFVTHPGYDT GNGIQLPGTS GQQPSVGQQM IFEEHGFRRT TPPTTATPIR HRPRPYPPNV GEEIQIGHIP REDVDYHLYP HGPGLNPNAS TGQEALSQTT ISWAPFQDTS EYIISCHPVG PTDDSCFDPY PGTSTSATLT GLTRGATYNI IVEALKDQQR HKVREEVVTV GNSVNEGLNQ PTDDSCFDPY TVSHYAVGDE WERMSESGFK LLCQCLGFGS GHFRCDSSRW CHDNGVNYKI GEKWDRQGEN GQMMSCTCLG NGKGEFKCDP HEATCYDDGK TYHVGEQWQK EYLGAICSCT CFGGQRGWRC DNCRRPGGEP SPEGTTGQSY NQYSQRYHQR TNTNVNCPIE CFMPLDVQAD REDSRE |
| 2 | Insulin-like growth factor binding protein-2 | MLPRVGCPAL PLPPPLLPL LPLLLLLLGA SGGGGGARAE VLFRCPPCTP ERLAACGPPP VAPPAAVAAV AGGARMPCAE LVREPGCGCC SVCARLEGEA CGVYTPRCGQ GLRCYPHPGS ELPLQALVMG EGTCEKRRDA EYGASPEQVA DNGDDHSEGG LVENHVDSTM NMLGGGSAG RKPLKSGMKE LAVFREKVTE QHRQMGKGGK HHLGLEEPKK LRPPPARTPC QQELDQVLER ISTMRLPDER GPLEHLYSLH IPNCDKHGLY NLKQCKMSLN GQRGECWCVN PNTGKLIQGA PTIRGDPECH LFYNEQQEAR GVHTQRMQ |

Figure 2c

| Seq.IDNO | Name | Protein Sequence |
|---|---|---|
| 3 | Transmembrane receptor PTK7 | MGAARGSPAR PRRLPLLSVL LLPLLGGTQT AIVFIKQPSS QDALQGRRAL LRCEVEAPGP VHVYWLLDGA PVQDTERRFA QGSSLSFAAV DPLQDSGTFQ CVARDDVTGE EARSANASFN IKWIEAGPVV LKHPASEAEI QPQTQVKLRC HIDGHPRPTY QWFRDGTPLS DGQSNHTVSS KERNLTLRPA GPEHSGLYSC CAHSAFSQAC SSQNFTLSIA DESFARVVLA PQDVVVARYE EAMFHCQFSA QPPPSLQWLF EDETPITNRS RPPHLRRATV FANGSLLLTQ VRPRNAGIYR CIGQGQRGPP IILEATLHLA EIEDMPLFEP RVFTAGSEER VTCLPPKGLP EPSVWWEHAG VRLPTHGRVY QKGHELVLAN IAESDAGVYT CHAANLAGQR RQDVNITVAT VPSWLKKPQD SQLEEGKPGY LDCLTQATPK PTVVWYRNQM LISEDSRFEV FKNGTLRINS VEVYDGTWYR CMSSTPAGSI EAQAVLQVLE KLKFTPPPQP QQCMGFDKEA TVPCSATGRE KPTIKWERAD GSSLPEWVTD NAGTLHFARV TRDDAGNYTC IASNGPQGQI RAHVQLTVAV FITFKVEPER TTVYQGHTAL LQCEAQGDPK PLIQWKGKDR ILDPTKLGPR MHIFQNGSLV IHDVAPEDSG RYTCIAGNSC NIKHTEAPLY VVDKPVPEES EGPGSPPPYK MIQTIGLSVG AAVAYIIAVL GLMFYCKKRC KAKRLQKQPE GEEPEMECLN GGPLQNGQPS AEIQEEVALT SLGSGPAATN KRHSTSDKMH FPRSSLQPIT TLGKSEFGEV FLAKAQGLEE GVAETLVLVK SLQSKDEQQQ LDFRRELEMF GKLNHANVVR LLGLCREAEP HYMVLEYVDL EDLKQFLRIS KSKDEKLKSQ PLSTKQKVAL CTQVALGMEH LSNNRFVHKD LAARNCLVSA QRQVKVSALG LSKDVYNSEY YHFRQAWVAL RWMSPEAILE GDFSTKSDVW ASGVLMWEVF THGEMPHGGQ ADDEVLADLQ AGKARLPQPE GCPSKLYRLM QRCWALSPKD RPSFSEIASA LGDSTVDSKP |
| 4 | Platelet-derived growth factor receptor alpha | MGTSHPAFLV LGCLLTGLSL ILCQLSLPSI LPNENEKVVQ LNSSFSLRCF GESEVSWQYP MSEEESSDVE IRNEENNSGL FVTVLEVSSA SAAHTGLYTC YYNHTQTEEN ELEGRHIYIY VPDPDVAFVP LGMTDYLVIV EDDDSAIIPC RTTDPETPVT LHNSEGVVPA SYDSRQGFNG TFTVGPYICE ATVKKKFQT IPFNVYALKA |

Figure 2d

| Seq.IDNO | Name | Protein Sequence |
|---|---|---|
| | | TSELDLEMEA LKTVYKSGET IVVTCAVFNN EVVDLQWTYP GEVKGKGITM LEEIKVPSIK LVYTLTVPEA |
| | | TVKDSGDYEC AARQATREVK EMKKVTISVH EKGFIEIKPT FSQLEAVNLH EVKHFVVEVR AYPPPRISWL |
| | | KNNLTLIENL TEITTDVEKI QEIRYRSKLK LIRAKEEDSG HYTIVAQNED AVKSYTFELL TQVPSSILDL |
| | | VDDHHGSTGG QTVRCTAEGT PLPDIEWMIC KDIKKCNNET SWTILANNVS NIITEIHSRD RSTVEGRVTF |
| | | AKVEETIAVR CLAKNLLGAE NRELKLVAPT LRSELTVAAA VLVLLVIVII SLIVLVIWK QKPRYEIRWR |
| | | VIESISPDGH EYIYVDPMQL PYDSRWEFPR DGLVLGRVLG SGAFGKVVEG TAYGLSRSQP VMKVAVKMLK |
| | | PTARSSEKQA LMSELKIMTH LGPHLNIVNL LGACTKSGPI YIITEYCFYG DLVNYLHKNR DSFLSHHPEK |
| | | PKKELDIFGL NPADESTRSY VILSFENNGD YMDMKQADTT QYVPMLERKE VSKYSDIQRS LYDRPASYKK |
| | | KSMLDSEVKN LLSDDNSEGL TLLDLLSFTY QVARGMEFLA SKNCVHRDLA ARNVLLAQGK IVKICDFGLA |
| | | RDIMHDSNYV SKGSTFLPVK WMAPESIFDN LYTTLSDVWS YGILLWEIFS LGGTPYPGMM VDSTFYNKIK |
| | | SGYRMAKPDH ATSEVYEIMV KCWNSEPEKR PSFYHLSEIV ENLLPGQYKK SYEKIHLDFL |
| | | KSDHPAVARMVDSDNAYIG VTYKNEEDKL KDWEGGLDEQ RLSADSGYII PLPDIDPVPE EEDLGKRNRH |
| | | SSQTSEESAI ETGSSSSTFI KREDETIEDI DMMDDIGIDS SDLVEDSFL |
| 5 | Collagen type XVIII alpha 1 | GEVGADGIPG FPGLPGREGI AGPQGPKGDR GSRGEKGDPG KDGLGQPGLP GPRGPPGPVV YVSEQDGSVL |
| | | SVPGPEGRRG FAGFPGPAGP KGNLGSKGEL GSPGPKGEKG EPGSIFSPDG GALGPAQKGA KGEPGFRGPP |
| | | GLYGRPGYKG EIGFPGRPGR PGMNGLKGEK PGEVGPPGP GPPFPFDFLQ KEAEMKGEKG DRGDAGQKGE RGEPGGGGFF |
| | | SSRPGPPGLP GNQGPPGPKG PKGEVGPPGP PGQFPFDFLQ KEAEMKGEKG DRGDAGQKGE RGEPGGGGFF |
| | | GSSLPGAPGA PGPRGYPGIP GPKGESIRGQ PGPPGPQGPP GIGYEGRQGP PGPPGPPGPP SFPGPHRQTI |
| | | SVPGPPGPPG PPGPPGTMGA SSGQVRLWAT RQAMLGQVHE VPEGWLIFVA EQEELYVRVQ NGFRKVQLEA |
| | | RTPLPRGTDN EVAALQPPVV QLHDSNPYPR REHPHPTARP WRADDILASP PGLPEPQPYP GGPHHSSYVH |
| | | CGPARPTSPP AHSHRDFQPV LHLVALNSPL SGGMRGIRGA DFQCFQQARA VGLAGTFRAF LSSRLQDLYS |

Figure 2e

| Seq.IDNO | Name | Protein sequence |
|---|---|---|
| 6 | Subtilisin-like protein (PACE4) | IVRRADRAAV PIVNLKDELL FPSWEALFSG SEGPLKPGAR IFSFDGKDVL RHPTWPQKSV WHGSDPNGRR LTESYCETWR TEAPSATGQA SSLLGGRLLG QSAASCHHAY IVLCIENSFM TASK<br>MPPRAPPAPG PRPPPRAAAA TDTAAGAGGA GGAGGAGGPG FRPLAPRPWR WLILLALPAA CSAPPPRPVY TNHWAVQVLG GPAEADRVAA AHGYLNLGQI GNLEDYYHFY HSKTFKRSTL SSRGPHTFLR MDPQVKHLQQ QEVKRRVKRQ VRSDPQALYF NDPIWSNMWY LHCGDKNSRC RSEMNVQAAW KRGYTGKNVV VTILDDGIER NHPDLAPNYD SYASYDVNGN DYDPSPRYDA SNENKHGTRC AGEVAASANN SYCIVGIAYN AKIGGIRMLD GDVTDVVEAK SLGIRPNYID IYSASWGPDD DGKTVDGPGR LAKQAFEYGI KKGRQGLGSI FVWASGNGGR EGDYCSCDGY TNSIYTISVS SATENGYKPW YLEECASTLA TTYSSGAFYE RKIVTTDLRQ RCTDGHTGTS VSAPMVAGII ALALEANSQL TWRDVQHLLV KTSRPAHLKA SDWKVNGAGH KVSHFYGFGL VDAEALVEA KKWTAVPSQH MCVAASDKRP RSIPLVQVLR TTALTSACAE HSDQRVVYLE HVVVRTSISH PRRGDLQIYL VSPSGTKSQL LAKRLLDLSN EGFTNWEFMT VHCWGEKAEG QWTLEIQDLP SQVRNPEKQG KLKEWSLILY GTAEHPYHTF SAHQSRSRML ELSAPELEPP KAALSPSQVE VPEDEEDYTA QSTPGSANIL QTSVCHPECG DKGCDGPNAD QCLNCVHFSL GSVKTSRKCV SVCPLGYFGD TAARRCRRCH KGCETCSSRA ATQCLSCRRG FYHHQEMNTC VTLCPAGFYA DESQKNCLKC HPSCKKCVDE PEKCTVCKEG FSLARGSCIP DCEPGTYFDS ELIRCGECHH TCGTCVGPGR EECIHCAKNF HFHDWKCVPA CGEGFYPEEM PGLPHKVCRR CDENCLSCAG SSRNCSRCKT GFTQLGTSCI TNHTCSNADE TFCEMVKSNR LCERKLFIQF CCRTCLLAG |
| 7 | Laminin M chain (Merosin) | MPGAAGVLLL LLLSGGLGGV QAQRPQQQRQ SQAHQQRGLF PAVLNLASNA LITTNATCGE KGPEMYCKLV EHVPGQPVRN PQCRICNQNS SNPNQRHPIT NAIDGKNTWW QSPSIKNGIE YHYVTITLDL QQVFQIAYVI VKAANSPRPG NNILERSLDD VEYKPWQYHA VTDTECLTLY NIYPRTGPPS YAKDDEVICT SFYSKIHPLE NGEIHISLIN GRPSADDPSP ELLEFTSARY IRLRFQRIRT LNADLMMFAH KDPREIDPIV TRRYYYSVKD ISVGGMCICY GHARACPLDP ATNKSRCECE HNTCGDSCDQ CCPGFHQKPW RAGTFLTKTE CEACNCHGKA |

Figure 2f

| Seq.IDNO | Name | Protein Sequence |
|---|---|---|
| | | EECYYDENVA RRNLSLNIRG KYIGGGVCIN CTQNTAGINC ETCTDGFFRP KGVSPNYPRP CQPCHCDPIG |
| | | SLNEVCVKDE KHARRGLAPG SCHCKTGFGG VSCDRCARGY TGYPDCKACN CSGLGSKNED PCFGPCICKE |
| | | NVEGGDCSRC KSGFFNLQED NWKGCDECFC SGVSNRCQSS YWTYGKIQDM SGWYLTDLPG RIRVAPQQDD |
| | | LDSPQQISIS NAEARQALPH SYYWSAPAPY LGNKLPAVGG QLTFTISYDL EEEEEDTERV LQLMIILEGN |
| | | DLSISTAQDE VYLHPSEEHT NVLLLKEESF TIHGTHFPVR RKEFMTVLAN LKRVLLQITY SFGMDAIFRL |
| | | SSVNLESAVS YPTDGSIAAA VEVCQCPPGY TGSSCESCWP RHRRVNGTIF GGICEPCQCF GHAESCDDVT |
| | | GECLNCKDHT GGPYCDKCLP GFYGEPTKGT SEDCQPCACP LNIPSNNFSP TCHLDRSLGL ICDGCPVGYT |
| | | GPRCERCAEG YFGQPSVPGG SCQPCQCNDN LDFSIPGSCD SLSGSCLICK PGTTGRYCEL CADGYFGDAV |
| | | DAKNCQPCRC NAGGSFSEVC HSQTGQCECR ANVQGQRCDK CKAGTFGLQS ARGCVPCNCN SFGSKSFDCE |
| | | ESGQCWCQPG VTGKKCDRCA HGYFNFQEGG CTACECSHLG NNCDPKTGRC ICPPNTIGEK CSKCAPNTWG |
| | | HSITTGCKAC NCSTVGSLDF QCNVNTGQCN CHPKFSGAKC TECSRGHWNY PRCNLCDCFL PGTDATTCDS |
| | | ETKKCSCSDQ TGQCTCKVNV EGIHCDRCRP GKFGLDAKNP LGCSSCYCFG TTTQCSEAKG LIRTWVTLKA |
| | | EQTILPLVDE ALQHTTTKGI VFQHPEIVAH MDLMREDLHL EPFYWKLPEQ FEGKKLMAYG GKLKYAIYFE |
| | | AREETGFSTY NPQVIIRGGT PTHARIIVRH MAAPLIGQLT RHEIEMTEKE WKYYGDDPRV HRTVTREDFL |
| | | DILYDIHYIL IKATYGNFMR QSRISEISME VAEQGRGTTM TPPADLIEKC DCPLGYSGLS CEACLPGFYR |
| | | LRSQPGGRTP GPTLGTCVPC QCNGHSSLCD PETSICQNCQ HHTAGDFCER CALGYYGIVK GLPNDCQQCA |
| | | CPLISSSNNF SPSCVAEGLD DYRCTACPRG YEGQYCERCA PGYTGSPGNP GGSCQECECD PYGSLPVPCD |
| | | PVTGFCTCRP GATGRKCDGC KWHHAREGWE CVFCGDECTG LLLGDLARLE QMVMSINLTG PLPAPYKMLY |
| | | GLENMTQELK HILSPQRAPE RLIQLAEGNL NTLVTEMNEL LTRATKVTAD GEQTGQDAER TNTRAKSLGE |
| | | FIKELARDAE AVNEKAIKLN ETLGTRDEAF ERNLEGLQKE IDQMIKELRR KNLETQKEIA EDELVAAEAL |
| | | LKKVKKLFGE SRGENEEMEK DLREKLADYK NKVDDAWDLL REATDKIREA NRLFAVNQKN MTALEKKEA |
| | | VESGKRQIEN TLKEGNDILD EANRLADEIN SIIDYVEDIQ TKLPPMSEEL NDKIDDLSQE IKDRKLAEKV |

Figure 2g

| Seq.IDNO | Name | Protein Sequence |
|---|---|---|
|  |  | SQAESHAAQL NDSSAVLDGI LDEAKNISFN ATAAFKAYSN IKDYIDEAEK VAKEAKDLAH EATKLATGPR GLLKEDAKGC LQKSFRILNE AKKLANDVKE NEDHLNGLKT RIENADARNG DLLRTLNDTL GKLSAIPNDT AAKLQAVKDK ARQANDTAKD VLAQITELHQ NLDGLKKNYN KLADSVAKTN AVVKDPSKNK IIADADATVK NLEQEADRLI DKLKPIKELE DNLKKNISEI KELINQARKQ ANSIKVSVSS GGDCIRTYKP EIKKGSYNNI VVNVKTAVAD NLLFYLGSAK FIDFLAIEMR KGKVSFLWDV GSGVGRVEYP DLTIDDSYWY RIVASRTGRN GTISVRALDG PKASIVPSTH HSTSPPGYTI LDVDANAMLF VGGLTGKLKK ADAVRVITFT GCMGETYFDN KPIGLWNFRE KEGDCKGCTV SPQVEDSEGT ATRDLRDFMS VELTDGHIKV SYDLGSGMAS VVSNQNHNDG KWKSFTLSRI QKQANISIVD IDTNQEENIA TSSSGNNFGL DLKADDKIYF GGLPTLRNLS MKARPEVNLK KYSGCLKDIE ISRTPYNILS SPDYVGVTKG CSLENVYTVS FPKPGFVELS PVPIDVGTEI NLSFSTKNES GILLGSGGT PAPPRRKRRQ TGQAYYVILL NRGRLEVHLS TGARTMRKIV IRPEPNLFHD GREHSVHVER TRGIFTVQVD ENRRYMQNLT VEQPIEVKKL FVGGAPPEFQ PSPLRNIPPF EGCIWNLVIN SVPMDFARPV SFKNADIGRC AHQKLREDED GAAPAEIVIQ PEPVPTPAFP TPTPVLTHGP CAAESEPALL IGSKQFGLSR NSHIAIAFDD TKVKNRLTIE LEVRTEAESG LLFYMAAINH ADFATVQLRN GLPYFSYDLG SGDTHTMIPT KINDGQWHKI KIMRSKQEGI LYVDGASNRT ISPKKADILD VVGMLYVGGL PINYTTRRIG PVTYSIDGCV RNLHMAEAPA DLEQPTSSFH VGTCFANAQR GTYFDGTGFA KAVGGFKVGL DLLVEFEFAT TTTTGVLLGI SSQKMDGMGI EMIDEKLMFH VDNGAGRFTA VYDAGVPGHL CDGQWHKVTA NKIKHRIELT VDGNQVEAQS PNPASTSADT NDPVFVGGFP DDLKQFGLTT SIPFRGCIRS LKLTKGTASH WRLILPRPWN |
| 8 | Elastin | MAGLTAAAPR PGVLLLLLSI LHPSRPGGVP GAIPGGVPGG VFYPGAGLGA LGGGALGPGG KPLKPVPGGL AGAGLGAGLG AFPAVTFPGA LVPGGVADAA AAYKAAKAGA GLGGVPGVGG LGVSAGAVVP QPGAGVKPGK VPGVGLPGVY PGGVLPGARF PGVGVLPGVP TGAGVKPKAP GVGGAFAGIP GVGPFGGPQP GVPLGYPIKA PKLPGGYGLP YTTGKLPYGY GPGGVAGAAG KAGYPTGTGV GPQAAAAAAA KAAAKFGAGA AGVLPGVGGA |

Figure 2h

| Seq.IDNO | Name | Protein Sequence |
|---|---|---|
| | | GVPGVPGAIP GIGGIAGVGT PAAAAAAAAA AKAAKYGAAA GLVPGGPGFG PGVVGVPGAG VPGVGVPGAG |
| | | IPVVPGAGIP GAAVPGVVSP EAAAKAAAKA AKYGARPGVG VGGIPTYGVG AGGFPGFVG VGGIPGVAGV |
| | | PSVGGVPGVG GVPGVGISPE AQAAAAAAKA KYGVGTPAAA AAKAAAKAAQ FALLNLAGLV PGVGVAPGVG |
| | | VAPGVGVAPG VGLAPGVGVA PGVGVAPGVG VAPGIGPGGV AAAAKSAAKV AAKAQLRAAA GLGAGIPGLG |
| | | VGVGVPGLGV GAGVPGLGVG AGVPGFGAVP GALAAAKAAK YGAAVPGVLG GLGALGGVGI PGGVVGAGPA |
| | | AAAAAAKAAA KAAQFGLVGA AGLGGLGVGG LGVPGVGGLG GIPPAAAAKA AKYGAAGLGG VLGGAGQFPL |
| | | GGVAARPGFG LSPIFPGGAC LGKACGRKRK | |
| 9 | Alpha-2 type IV collagen | MGRDQRAVAG PALRRWLLLG TVTVGFLAQS VLAGVKKFDV PCGGRDCSGG CQCYPEKGGR GQPGPVGPQG |
| | | YNGPPGLQGF PGLQGRKGDK GERGAPGVTG PKGDVGARGV SGFPGADGIP GHPGQGGPRG RPGYDGCNGT |
| | | QGDSGPQGPP GSEGFTGPPG PQGPKGQKGE PYALPKEERD RYRGEPGEPG LVGFQGPPGR PGHVGQMGPV |
| | | GAPGRPGPPG PPGPKGQQGN RGLGFYGVKG EKGDVGQPGP NGIPSDTLHP IIAPTGVTFH PDQYKGEKGS |
| | | EGEPGIRGIS LKGEEGIMGF PGLRGYPGLS GEKGSPGQKG SRGLDGYQGP DGPRGPKGEA GDPGPPGLPA |
| | | YSPHPSLAKG ARGDPGFPGA QGEPGSQGEP GDPGLPGPPG LSIGDGDQRR GLPGEMGPKG FIGDPGIPAL |
| | | YGGPPGPGDK RGPPGPPGLP GPPGPDGFLF GLKGAKGRAG FPGLPGSPGA RGPKGWKGDA GECRCTEGDE |
| | | AIKGLPGLPG PKGFAGINGE PGRKGDKGDP GQHGLPGFPG LKGVPGNIGA PGPGAKGDS RTITTKGERG |
| | | QPGVPGVPGM KGDDGSPGRD GLDGFPGLPG PPGDGIKGPP GDPGYPGIPG TKGTPGEMGP PGLGLPGLKG |
| | | QRGFPGDAGL PGPPGFLGPP GPAGTPGQID CDTDVKRAVG GDRQEAIQPG CIAGPKGLPG LPGPPGPTGA |
| | | KGLRGIPGFA GADGGPGPRG LPGDAGREGF PGPPGFIGPR GSKGAVGLPG PDGSPGPIGL PGPDGPPGER |
| | | GLPGEVLGAQ PGPRGDAGVP GQPGLKGLPG DRGPPGFRGS QGMPGMPGLK GQPGLPGPSG QPGLYGPPGL |
| | | HGFPGAPGQE GPLGLPGIPG REGLPGDRGD PGDTGAPGPV GMKGLSGDRG DAGFTGEQGH PGSPGFKGID |
| | | GMPGTPGLKG DRGSPGMDGF QGMPGLKGRP GFPGSKGEAG FFGIPLGKGL AGEPGFKGSR GDPGPPGPPP |

Figure 2i

| Seq.IDNO | Name | Protein Sequence |
|---|---|---|
| | | VILPGMKDIK GEKGDEGPMG LKGYLGAKGI QGMPGIPGLS GIPGLPGRPG HIKGVKGDIG VPGIPGLPGF PGVAGPPGIT GFPGFIGSRG DKGAPGRAGL YGEIGATGDF GDIGDTINLP GRPGLKGERG TTGIPGLKGF FGEKGTEGDI GFPGITGVTG VQGPPGLKGQ TGFPGLTCPP GSQELGRIG LPGGKGDDGW PGAPGLPGFP GLRGIRGLHG LPGTKGFPGS PGSDIHGDPG FPGPPGERGD PGEANTLPGP VGVPGQKGDQ GAPGERGPPG SPGLQGFPGI TPPSNISGAP GDKGAPGIFG LKGYRGPPGP PGSAALPGSK GDTGNPGAPG TPGTKGWAGD SGPQGRPGVF GLPGEKGPRG EQGFMGNTGP TGAVGDRGPK GPKGDPGFPG APGTVGAPGI AGIPQKIAIQ PGTVGPQGRR GPPGAPGEIG PQGPPGEPGF RGAPGKAGPQ GRGGVSAVPG FRGDEGPIGH QGPIGQEGAP GRPGSPGLPG MPGRSVSIGY LLVKHSQTDQ EPMCPVGMNK LWSGYSLLYF EGQEKAHNQD LGLAGSCLAR FSTMPFLYCN PGDVCYYASR NDKSYWLSTT APLPMMPVAE DEIKPYISRC SVCEAPAIAI AVHSQDVSIP HCPAGWRSLW IGYSFLMHTA AGDEGGGQSL VSPGSCLEDF RATPFIECNG GRGTCHYYAN KYSFWLTTIP EQSFQGSPSA DTLKAGLIRT HISRCQVCMK NL |
| 10 | p27 | MEASALTSSA VTSVAKVVRV ASGSAVVLPL ARIATVVIGG VVAMAAVPMV LSAMGFTAAG IASSSIAAKM MSAAAIANGG GVASGSLVGT LQSLGATGLS GLTKFILGSI GSAIAAVIAR FY |
| 11 | Reticulocalbin | MARGGRGRRL GLALGLLLAL VLAPRVLRAK PTVRKERVVR PDSELGERPP EDNQSFQYDH EAFLGKEDSK TFDQLTPDES KERLGKIVDR IDNDGDFVT TEELKTWIKR VQKRYIFDNV AKVWKDYDRD KDDKISWEEY KQATYGYYLG NPAEFHDSSD HHTFKKMLPR DERRFKAADL NGDLTATREE FTAFLHPEEF EHMKEIVVLE TLEDIDKNGD GFVDQDEYIA DMFSHEENGP EPDWVLSERE QFNEFRDLNK DGKLDKDEIR HWILPQDYDH AQAEARHLVY ESDKNKDEKL TKEEILENWN MFVGSQATNY GEDLTKNHDE L |
| 12 | Aldehyde dehydrogenase 6 | MATANGAVEN GQPDGKPPAL PRPIRNLEVK FTKIFINNEW HESKSGKKFA TCNPSTREQI CEVEEGDKPD VDKAVEAAQV AFQRGSPWRR LDALSRGRLL HQLADLVERD RATLAALETM DTGKPFLHAF FIDLEGCIRT |

Figure 2j

| Seq.IDNO | Name | Protein Sequence |
|---|---|---|
| | | LRYFAGWADK IQGKTIPTDD NVVCFTRHEP IGVCGAITPW NFPLLMLVWK LAPALCCGNT MVLKPAEQTP LTALYLGSLI KEAGFPPGVV NIVPGFGPTV GAAISSHPQI NKIAFTGSTE VGKLVKEAAS RSNLKRVTLE LGGKNPCIVC ADADLDLAVE CAHQGVFFNQ GQCCTAASRV FVEEQVYSEF VRRSVEYAKK RPVGDPFDVK TEQGPQIDQK QFDKILELIE SGKKEGAKLE CGGSAMEDKG LFIKPTVFSE VTDNMRIAKE EIFGPVQPIL KFKSIEEVIK RANSTDYGLT AAVFTKNLDK ALKLASALES GTVWINCYNA LYAQAPFGGF KMSGNGRELG EYALAEYTEV KTVTIKLGDK NP |
| 13 | Gravin | MGAGSSTEQR SPEQPPEGSS TPAEPEPSGG GPSAEAAPDT TADPAIAASD PATKLLQKNG QLSTINGVAE QDELSLQEGD LNGQKGALNG QGALNSQEEE EVIVTEVGQR DSEDVSERDS DKEMATKSAV VHDITDDGQE ENRNIEQIPS SESNLEELTQ PTESQANDIG FKKVFKFVGF KFTVKKDKTE KPDTVQLLTV KKDEGEGAAG AGDHQDPSLG AGEAASKESE PKQSTEKPEE TLKREQSHAE ISPPAESGQA VEECKEEGEE KQEKEPSKSA ESPTSPVTSE TGSTFKKFFT QGWAGWRKKT SFRKPKEDEV EASEKKKEQE PEKVDTEEDG KAEVASEKLT ASEQAHPQEP AESAHEPRLS AEYEKVELPS EEQVSGSQGP SEEKPAPLAT EVFDEKIEVH QEEVVAEVHV STVEERTEEQ KTEVEETAGS VPAEELVGMD AEPQEAEPAK ELVKLKETCV SGEDPTQGAD LSPDEKVLSK PPEGVVSEVE MLSSQERMKV QGSPLKKLFT STGLKKLSGK KQKGKRGGGD EESGEHTQVP ADSPDSQEEQ KGESSASSPE EPEEITCLEK GLAEVQQDGE AEEGATSDGE KKREGVTPWA SFKKMVTPKK RVRRPSESDK EDELDKVKSA TLSSTESTAS EMQEEMKGSV EEPKPEEPKR KVDTSVSWEA LICVGSSKKR ARRRSSSDEE GGPKAMGGDH QKADEAGKDK ETGTDGILAG SQEHDPGQGS SSPEQAGSPT EGEGVSTWES FKKRLVTPRKK SKSKLEEKSE DSIAGSGVEH STPDTEPGKE ESWVSIKKFI PGRRKKRPDG KQEQAPVEDA GPTGANEDDS DVPAVVPLSE YDAVEREKME AQQAQKGAEQ PEQKAATEVS KELSESQVHM MAAAVADGTR AATIIEERSP SWISASVTEP LEQVEAEAAL LTEEVLEREV IAEEEPPTVT EPLPENREAR GDTVVSEAEL TPEAVTAAET AGPLGSEEGT EASAAEETTE MVSAVSQLTD SPDTTEEATP VQEVEGGVPD IEEQERRTQE VLQAVAEKVK |

Figure 2k

| Seq.IDNO | Name | Protein Sequence |
|---|---|---|
|  |  | EESQLPGTGG PEDVLQPVQR AEAERPEEQA EASGLKKETD VVLKVDAQEA KTEPFTQGKV VGQTTPESFE<br>KAPQVTESIE SSELVTTCQA ETLAGVKSQE MVMEQAIPPD SVETPTDSET DGSTPVADFD APGTTQKDEI<br>VEIHEENEVA SGTQSGGTEA EAVPAQKERP PAPSSFVFQE ETKEQSKMED TLEHTDKEVS VETVSILSKT<br>EGTQEADQYA DEKTKDVPFF EGLEGSIDTG ITVSREKVTE VALKGEGTEE AECKKDDALE LQSHAKSPPS<br>PVEREMVVQV EREKTEAEPT HVNEEKLEHE TAVTVSEEVS KQLLQTVNVP IIDGAKEVSS LEGSPPPCLG<br>QEEAVCTKIQ VQSSEASFTL TAAAEEEKVL GETANILETG ETLEPAGAHL VLEEKSSEKN EDFAAHPGED<br>AVPTGPDCQA KSTPVIVSAT TKKGLSSDLE GEKTTSLKWK SDEVDEQVAC QEVKVSVAIE DLEPENGILE<br>LETKSSKLVQ NIIQTAVDQF VRTEETATEM LTSELQTQAH VIKADSQDAG QETEKEGEEP QASAQDETPI<br>TSAKEESEST AVGQAHSDIS KDMSEASEKT MTVEVEGSTV NDQQLEEVVL PSEEEGGGAG TKSVPEDDGH<br>ALLAERIEKS LVEPKEDEKG DDVDDPENQN SALADTDASG GLTKESPDTN GPKQKEKEDA QEVELQEGKV<br>HSESDKAITP QAQELQKQE RESAKSELTE S |
| 14 | Nidogen | MLASSSRIRA AWTRALLLPL LLAGPVGCLS RQELFPFGPG QGDLELEDGD DFVSPALELS GALRFYDRSD<br>IDAVYVTNG IIATSEPPAK ESHPGLFPPT FGAVAPFLAD LDTTDGLGKV YREDLSPSI TQRAAECVHR<br>GFPEISFQPS SAVVVTWESV APYQGPSRDP DQKGKRNTFQ AVLASSDSSS YAIFLYPEDG LQFHTTFSKK<br>ENNQVPAVVA FSQGSVGFLW KSNGAYNIFA NDRESIENLA KSSNSGQQGV WVFEIGSPAT TNGVVPADVI<br>LGTEDGAEYD DEDEDYDLAT TRLGLEDVGT TPFSYKALRR GGADTYSVPS VLSPRRAATE RPLGPPTERT<br>RSFQLAVETF HQQHPQVIDV DEVEETGVVF SYNTDSRQTC ANNRHQCSVH AECRDYATGF CCSCVAGYTG<br>NGRQCVAEGS PQRVNGKVKG RIFVGSSQVP IVFENTDLHS YVVMNHGRSY TAISTIPETV GYSLLPLAPV<br>GGIIGWMFAV EQDGFKNGFS ITGGEFTRQA EVTFVGHPGN LVIKQRFSGI DEHGHLTIDT ELEGRVPQIP |

Figure 21

| Seq.IDNO | Name | Protein Sequence |
|---|---|---|
|  |  | FGSSVHIEPY TELYHYSTSV ITSSSTREYT VTEPERDGAS PSRIYTYQWR QTITFQECVH DDSRPALPST<br>QQLSVDSVFV LYNQEEKILR YAFSNSIGPV REGSPDALQN PCYIGTHGCD TNAACRPGPR TQFTCECSIG<br>FRGDGRTCYD IDECSEQPSV CGSHTICNNH PGTFRCECVE GYQFSDEGTC VAVVDQRPIN YCETGLHNCD<br>IPQRAQCIYT GGSSYTCSCL PGFSGDGQAC QDVDECQPSR CHPDAFCYNT PGSFTCQCKP GYQGDGFRCV<br>PGEVEKTRCQ HEREHILGAA GATDPQRPIP PGLFVPECDA HGHYAPTQCH GSTGYCWCVD RDGREVEGTR<br>TRPGMTPPCL STVAPPIHQG PAVPTAVIPL PPGTHLLFAQ TGKIERLPLE GNTMRKTEAK AFLHVPAKVI<br>IGLAFDCVDK MVYWTDITEP SIGRASLHGG EPTTIIRQDL GSPEGIAVDH LGRNIFWTDS NLDRIEVAKL<br>DGTQRRVLFE TDLVNPRGIV TDSVRGNLYW SIGRASLHGG ETSYMDGTNR RILVQDDLGL PNGLHFDAFS<br>SQLCWDAGT NRAECLNPSQ PSRRKALEGL QYPFAVTSYG KNLYFTDWKM NSVVALDLAI SKETDAFQPH<br>KQTRLYGITT ALSQCPQGHN YCSVNNGGCT HLCLATPGSR TCRCPDNTLG VDCIERK |
| 15 | Phospholipase Epsilon | C MPSEKKISSA NDCISFMQAG CELKKVRPNS RIYNRFFTLD TDLQALRWEP SKKDLEKAKL DISAIKEIRL<br>GKNTETFTNN GLADQICEDC AFSILHGENY ESLDLVANSA DVANIWVSGL RYLVSRSKQP LDFMEGNQNT<br>PRFMWLKTVF EAADVDGNGI MLEDTSVELI KQLNPTLKEA KIRLKFKEIQ KSKEKLTTRV TEEEFCEAFC<br>ELCTRPEVYF LLVQISKNKE YLDANDLMLF LEAEQGVTHI TEDICLDIIR RYELSEEGRQ KGFLAIDGFT<br>QYLLSSECDI FDPEQKKVAQ DMTQPLSHYY INASHNTYLI EDQFRGPADI NGYIRALKMG CRSVELDVSD<br>GSDNEPILCN RNNMTTHVSF RSVIEVINKF AFVASEYPLI LCLGNHCSLP QQKVMAQQMK KVFGNKLYTE<br>APLPSESYLP SPEKLKRMII VKGKKLPSDP DVLEGEVTDE DEEAQMSRRM SVDYNGEQKQ IRLCRELSDL<br>VSICKSVQYR DFELSMKSQN YWEMCSFSET EASRIANEYP EDFVNYNKKF LSRIYPSAMR IDSSNLNPQD<br>FWNCGCQIVA MNFQTPGPMM DLHTGWFLQN GGCGYVLRPS IMRDEVSYFS ANTKGILPGV SPLALHIKI<br>SGQNFPKPKG ACAKGDVIDP YVCIEIHGIP ADCSEQRTKT VQQNSDNPIF DETFEFQVNL PELAMIRFVV<br>LDDDYIGDEF IGQYTIPFEC LQPGYRHVPL RSFVGDIMEH VTLFVHIAIT NRSGGGKAQK RSLSVRMGKK |

Figure 2m

| Seq.IDNO | Name | Protein Sequence |
|---|---|---|
| | | VREYTMLRNI GLKTIDDIFK IAVHPLREAI DMRENMQNAI VSIKELCGLP PIASLKQCLL TLSSRLITSD NTPSVSLVMK DSFPYLEPLG AIPDVQKKML TAYDLMIQES RFLIEMADTV QEKIVQCQKA GMEFHEELHN LGAKEGLKGR KLNKATESFA WNITVLKGQG DLLKNAKNEA IENMKQIQLA CLSCGLSKAP SSSAEAKSKR SLEAIEEKES SEENGKL |

SEQUENCE LISTING

<160> NUMBER OF SEQ ID NOS: 15

<210> SEQ ID NO 1
<211> LENGTH: 2386
<212> TYPE: PRT
<213> ORGANISM: Homo sapiens

<400> SEQUENCE: 1

```
Met Leu Arg Gly Pro Gly Pro Gly Leu Leu Leu Ala Val Gln Cys
  1               5                  10                  15

Leu Gly Thr Ala Val Pro Ser Thr Gly Ala Ser Lys Ser Lys Arg Gln
                20                  25                  30

Ala Gln Gln Met Val Gln Pro Gln Ser Pro Val Ala Val Ser Gln Ser
            35                  40                  45

Lys Pro Gly Cys Tyr Asp Asn Gly Lys His Tyr Gln Ile Asn Gln Gln
    50                  55                  60

Trp Glu Arg Thr Tyr Leu Gly Asn Ala Leu Val Cys Thr Cys Tyr Gly
 65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
            260                 265                 270

His Thr Ser Val Gln Thr Thr Ser Ser Gly Ser Gly Pro Phe Thr Asp
        275                 280                 285

Val Arg Ala Ala Val Tyr Gln Pro Gln Pro His Pro Gln Pro Pro Pro
    290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
            340                 345                 350

Gly Asn Ser Asn Gly Glu Pro Cys Val Leu Pro Phe Thr Tyr Asn Gly
```

-continued

```
              355                 360                 365
Arg Thr Phe Tyr Ser Cys Thr Thr Glu Gly Arg Gln Asp Gly His Leu
    370                 375                 380
Trp Cys Ser Thr Thr Ser Asn Tyr Glu Gln Asp Gln Lys Tyr Ser Phe
385                 390                 395                 400
Cys Thr Asp His Thr Val Leu Val Gln Thr Gln Gly Gly Asn Ser Asn
                405                 410                 415
Gly Ala Leu Cys His Phe Pro Phe Leu Tyr Asn Asn His Asn Tyr Thr
                420                 425                 430
Asp Cys Thr Ser Glu Gly Arg Arg Asp Asn Met Lys Trp Cys Gly Thr
        435                 440                 445
Thr Gln Asn Tyr Asp Ala Asp Gln Lys Phe Gly Phe Cys Pro Met Ala
    450                 455                 460
Ala His Glu Glu Ile Cys Thr Thr Asn Glu Gly Val Met Tyr Arg Ile
465                 470                 475                 480
Gly Asp Gln Trp Asp Lys Gln His Asp Met Gly His Met Met Arg Cys
                485                 490                 495
Thr Cys Val Gly Asn Gly Arg Gly Glu Trp Thr Cys Ile Ala Tyr Ser
                500                 505                 510
Gln Leu Arg Asp Gln Cys Ile Val Asp Asp Ile Thr Tyr Asn Val Asn
        515                 520                 525
Asp Thr Phe His Lys Arg His Glu Glu Gly His Met Leu Asn Cys Thr
    530                 535                 540
Cys Phe Gly Gln Gly Arg Gly Arg Trp Lys Cys Asp Pro Val Asp Gln
545                 550                 555                 560
Cys Gln Asp Ser Glu Thr Gly Thr Phe Tyr Gln Ile Gly Asp Ser Trp
                565                 570                 575
Glu Lys Tyr Val His Gly Val Arg Tyr Gln Cys Tyr Cys Tyr Gly Arg
                580                 585                 590
Gly Ile Gly Glu Trp His Cys Gln Pro Leu Gln Thr Tyr Pro Ser Ser
        595                 600                 605
Ser Gly Pro Val Glu Val Phe Ile Thr Glu Thr Pro Ser Gln Pro Asn
    610                 615                 620
Ser His Pro Ile Gln Trp Asn Ala Pro Gln Pro Ser His Ile Ser Lys
625                 630                 635                 640
Tyr Ile Leu Arg Trp Arg Pro Lys Asn Ser Val Gly Arg Trp Lys Glu
                645                 650                 655
Ala Thr Ile Pro Gly His Leu Asn Ser Tyr Thr Ile Lys Gly Leu Lys
                660                 665                 670
Pro Gly Val Val Tyr Glu Gly Gln Leu Ile Ser Ile Gln Gln Tyr Gly
        675                 680                 685
His Gln Glu Val Thr Arg Phe Asp Phe Thr Thr Thr Ser Thr Ser Thr
    690                 695                 700
Pro Val Thr Ser Asn Thr Val Thr Gly Glu Thr Thr Pro Phe Ser Pro
705                 710                 715                 720
Leu Val Ala Thr Ser Glu Ser Val Thr Glu Ile Thr Ala Ser Ser Phe
                725                 730                 735
Val Val Ser Trp Val Ser Ala Ser Asp Thr Val Ser Gly Phe Arg Val
                740                 745                 750
Glu Tyr Glu Leu Ser Glu Glu Gly Asp Glu Pro Gln Tyr Leu Asp Leu
        755                 760                 765
Pro Ser Thr Ala Thr Ser Val Asn Ile Pro Asp Leu Leu Pro Gly Arg
    770                 775                 780
```

-continued

```
Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
                805                 810                 815

Pro Thr Val Asp Gln Val Asp Asp Thr Ser Ile Val Val Arg Trp Ser
            820                 825                 830

Arg Pro Gln Ala Pro Ile Thr Gly Tyr Arg Ile Val Tyr Ser Pro Ser
        835                 840                 845

Val Glu Gly Ser Ser Thr Glu Leu Asn Leu Pro Glu Thr Ala Asn Ser
850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
            900                 905                 910

Leu Gln Phe Val Glu Val Thr Asp Val Lys Val Thr Ile Met Trp Thr
        915                 920                 925

Pro Pro Glu Ser Ala Val Thr Gly Tyr Arg Val Asp Val Ile Pro Val
930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
            980                 985                 990

Gln Thr Thr Lys Leu Asp Ala Pro Thr Asn Leu Gln Phe Val Asn Glu
        995                 1000                1005

Thr Asp Ser Thr Val Leu Val Arg Trp Thr Pro Pro Arg Ala Gln Ile
    1010                1015                1020

Thr Gly Tyr Arg Leu Thr Val Gly Leu Thr Arg Arg Gly Gln Pro Arg
1025                1030                1035                1040

Gln Tyr Asn Val Gly Pro Ser Val Ser Lys Tyr Pro Leu Arg Asn Leu
                1045                1050                1055

Gln Pro Ala Ser Glu Tyr Thr Val Ser Leu Val Ala Ile Lys Gly Asn
            1060                1065                1070

Gln Glu Ser Pro Lys Ala Thr Gly Val Phe Thr Thr Leu Gln Pro Gly
        1075                1080                1085

Ser Ser Ile Pro Pro Tyr Asn Thr Glu Val Thr Glu Thr Thr Ile Val
    1090                1095                1100

Ile Thr Trp Thr Pro Ala Pro Arg Ile Gly Phe Lys Leu Gly Val Arg
1105                1110                1115                1120

Pro Ser Gln Gly Gly Glu Ala Pro Arg Glu Val Thr Ser Asp Ser Gly
                1125                1130                1135

Ser Ile Val Val Ser Gly Leu Thr Pro Gly Val Glu Tyr Val Tyr Thr
            1140                1145                1150

Ile Gln Val Leu Arg Asp Gly Gln Glu Arg Asp Ala Pro Ile Val Asn
        1155                1160                1165

Lys Val Val Thr Pro Leu Ser Pro Pro Thr Asn Leu His Leu Glu Ala
    1170                1175                1180

Asn Pro Asp Thr Gly Val Leu Thr Val Ser Trp Glu Arg Ser Thr Thr
1185                1190                1195                1200
```

-continued

Pro Asp Ile Thr Gly Tyr Arg Ile Thr Thr Pro Thr Asn Gly Gln
            1205                1210                1215

Gln Gly Asn Ser Leu Glu Glu Val Val His Ala Asp Gln Ser Ser Cys
        1220                1225                1230

Thr Phe Asp Asn Leu Ser Pro Gly Leu Glu Tyr Asn Val Ser Val Tyr
    1235                1240                1245

Thr Val Lys Asp Asp Lys Glu Ser Val Pro Ile Ser Asp Thr Ile Ile
1250                1255                1260

Pro Ala Val Pro Pro Pro Thr Asp Leu Arg Phe Thr Asn Ile Gly Pro
1265                1270                1275                1280

Asp Thr Met Arg Val Thr Trp Ala Pro Pro Ser Ile Asp Leu Thr
            1285                1290                1295

Asn Phe Leu Val Arg Tyr Ser Pro Val Lys Asn Glu Glu Asp Val Ala
        1300                1305                1310

Glu Leu Ser Ile Ser Pro Ser Asp Asn Ala Val Val Leu Thr Asn Leu
    1315                1320                1325

Leu Pro Gly Thr Glu Tyr Val Val Ser Val Ser Ser Val Tyr Glu Gln
    1330                1335                1340

His Glu Ser Thr Pro Leu Arg Gly Arg Gln Lys Thr Gly Leu Asp Ser
1345                1350                1355                1360

Pro Thr Gly Ile Asp Phe Ser Asp Ile Thr Ala Asn Ser Phe Thr Val
            1365                1370                1375

His Trp Ile Ala Pro Arg Ala Thr Ile Thr Gly Tyr Arg Ile Arg His
        1380                1385                1390

His Pro Glu His Phe Ser Gly Arg Pro Arg Glu Asp Arg Val Pro His
    1395                1400                1405

Ser Arg Asn Ser Ile Thr Leu Thr Asn Leu Thr Pro Gly Thr Glu Tyr
    1410                1415                1420

Val Val Ser Ile Val Ala Leu Asn Gly Arg Glu Glu Ser Pro Leu Leu
1425                1430                1435                1440

Ile Gly Gln Gln Ser Thr Val Ser Asp Val Pro Arg Asp Leu Glu Val
            1445                1450                1455

Val Ala Ala Thr Pro Thr Ser Leu Leu Ile Ser Trp Asp Ala Pro Ala
        1460                1465                1470

Val Thr Val Arg Tyr Tyr Arg Ile Thr Tyr Gly Glu Thr Gly Gly Asn
    1475                1480                1485

Ser Pro Val Gln Glu Phe Thr Val Pro Gly Ser Lys Ser Thr Ala Thr
    1490                1495                1500

Ile Ser Gly Leu Lys Pro Gly Val Asp Tyr Thr Ile Thr Val Tyr Ala
1505                1510                1515                1520

Val Thr Gly Arg Gly Asp Ser Pro Ala Ser Ser Lys Pro Ile Ser Ile
            1525                1530                1535

Asn Tyr Arg Thr Glu Ile Asp Lys Pro Ser Gln Met Gln Val Thr Asp
        1540                1545                1550

Val Gln Asp Asn Ser Ile Ser Val Lys Trp Leu Pro Ser Ser Ser Pro
    1555                1560                1565

Val Thr Gly Tyr Arg Val Thr Thr Pro Lys Asn Gly Pro Gly Pro
    1570                1575                1580

Thr Lys Thr Lys Thr Ala Gly Pro Asp Gln Thr Glu Met Thr Ile Glu
1585                1590                1595                1600

Gly Leu Gln Pro Thr Val Glu Tyr Val Val Ser Val Tyr Ala Gln Asn
            1605                1610                1615

Pro Ser Gly Glu Ser Gln Pro Leu Val Gln Thr Ala Val Thr Asn Ile

-continued

```
              1620            1625            1630
Asp Arg Pro Lys Gly Leu Ala Phe Thr Asp Val Asp Val Asp Ser Ile
            1635            1640            1645
Lys Ile Ala Trp Glu Ser Pro Gln Gly Gln Val Ser Arg Tyr Arg Val
        1650            1655            1660
Thr Tyr Ser Ser Pro Glu Asp Gly Ile His Glu Leu Phe Pro Ala Pro
1665            1670            1675            1680
Asp Gly Glu Glu Asp Thr Ala Glu Leu Gln Gly Leu Arg Pro Gly Ser
            1685            1690            1695
Glu Tyr Thr Val Ser Val Val Ala Leu His Asp Asp Met Glu Ser Gln
        1700            1705            1710
Pro Leu Ile Gly Thr Gln Ser Thr Ala Ile Pro Ala Pro Thr Asp Leu
            1715            1720            1725
Lys Phe Thr Gln Val Thr Pro Thr Ser Leu Ser Ala Gln Trp Thr Pro
            1730            1735            1740
Pro Asn Val Gln Leu Thr Gly Tyr Arg Val Arg Val Thr Pro Lys Glu
1745            1750            1755            1760
Lys Thr Gly Pro Met Lys Glu Ile Asn Leu Ala Pro Asp Ser Ser Ser
            1765            1770            1775
Val Val Val Ser Gly Leu Met Val Ala Thr Lys Tyr Glu Val Ser Val
            1780            1785            1790
Tyr Ala Leu Lys Asp Thr Leu Thr Ser Arg Pro Ala Gln Gly Val Val
        1795            1800            1805
Thr Thr Leu Glu Asn Val Ser Pro Pro Arg Arg Ala Arg Val Thr Asp
    1810            1815            1820
Ala Thr Glu Thr Thr Ile Thr Ile Ser Trp Arg Thr Lys Thr Glu Thr
1825            1830            1835            1840
Ile Thr Gly Phe Gln Val Asp Ala Val Pro Ala Asn Gly Gln Thr Pro
            1845            1850            1855
Ile Gln Arg Thr Ile Lys Pro Asp Val Arg Ser Tyr Thr Ile Thr Gly
            1860            1865            1870
Leu Gln Pro Gly Thr Asp Tyr Lys Ile Tyr Leu Tyr Thr Leu Asn Asp
        1875            1880            1885
Asn Ala Arg Ser Ser Pro Val Val Ile Asp Ala Ser Thr Ala Ile Asp
        1890            1895            1900
Ala Pro Ser Asn Leu Arg Phe Leu Ala Thr Thr Pro Asn Ser Leu Leu
1905            1910            1915            1920
Val Ser Trp Gln Pro Pro Arg Ala Arg Ile Thr Gly Tyr Ile Ile Lys
            1925            1930            1935
Tyr Glu Lys Pro Gly Ser Pro Pro Arg Glu Val Val Pro Arg Pro Arg
            1940            1945            1950
Pro Gly Val Thr Glu Ala Thr Ile Thr Gly Leu Glu Pro Gly Thr Glu
            1955            1960            1965
Tyr Thr Ile Tyr Val Ile Ala Leu Lys Asn Asn Gln Lys Ser Glu Pro
        1970            1975            1980
Leu Ile Gly Arg Lys Lys Thr Asp Glu Leu Pro Gln Leu Val Thr Leu
1985            1990            1995            2000
Pro His Pro Asn Leu His Gly Pro Glu Ile Leu Asp Val Pro Ser Thr
            2005            2010            2015
Val Gln Lys Thr Pro Phe Val Thr His Pro Gly Tyr Asp Thr Gly Asn
        2020            2025            2030
Gly Ile Gln Leu Pro Gly Thr Ser Gly Gln Gln Pro Ser Val Gly Gln
        2035            2040            2045
```

```
Gln Met Ile Phe Glu Glu His Gly Phe Arg Arg Thr Thr Pro Pro Thr
    2050                2055                2060
Thr Ala Thr Pro Ile Arg His Arg Pro Arg Pro Tyr Pro Pro Asn Val
2065                2070                2075                2080
Gly Glu Glu Ile Gln Ile Gly His Ile Pro Arg Glu Asp Val Asp Tyr
            2085                2090                2095
His Leu Tyr Pro His Gly Pro Gly Leu Asn Pro Asn Ala Ser Thr Gly
        2100                2105                2110
Gln Glu Ala Leu Ser Gln Thr Thr Ile Ser Trp Ala Pro Phe Gln Asp
        2115                2120                2125
Thr Ser Glu Tyr Ile Ile Ser Cys His Pro Val Gly Thr Asp Glu Glu
        2130                2135                2140
Pro Leu Gln Phe Arg Val Pro Gly Thr Ser Thr Ser Ala Thr Leu Thr
2145                2150                2155                2160
Gly Leu Thr Arg Gly Ala Thr Tyr Asn Ile Ile Val Glu Ala Leu Lys
            2165                2170                2175
Asp Gln Gln Arg His Lys Val Arg Glu Glu Val Val Thr Val Gly Asn
        2180                2185                2190
Ser Val Asn Glu Gly Leu Asn Gln Pro Thr Asp Asp Ser Cys Phe Asp
        2195                2200                2205
Pro Tyr Thr Val Ser His Tyr Ala Val Gly Asp Glu Trp Glu Arg Met
    2210                2215                2220
Ser Glu Ser Gly Phe Lys Leu Leu Cys Gln Cys Leu Gly Phe Gly Ser
2225                2230                2235                2240
Gly His Phe Arg Cys Asp Ser Ser Arg Trp Cys His Asp Asn Gly Val
            2245                2250                2255
Asn Tyr Lys Ile Gly Glu Lys Trp Asp Arg Gln Gly Glu Asn Gly Gln
        2260                2265                2270
Met Met Ser Cys Thr Cys Leu Gly Asn Gly Lys Gly Glu Phe Lys Cys
        2275                2280                2285
Asp Pro His Glu Ala Thr Cys Tyr Asp Asp Gly Lys Thr Tyr His Val
    2290                2295                2300
Gly Glu Gln Trp Gln Lys Glu Tyr Leu Gly Ala Ile Cys Ser Cys Thr
2305                2310                2315                2320
Cys Phe Gly Gly Gln Arg Gly Trp Arg Cys Asp Asn Cys Arg Arg Pro
            2325                2330                2335
Gly Gly Glu Pro Ser Pro Glu Gly Thr Thr Gly Gln Ser Tyr Asn Gln
        2340                2345                2350
Tyr Ser Gln Arg Tyr His Gln Arg Thr Asn Thr Asn Val Asn Cys Pro
        2355                2360                2365
Ile Glu Cys Phe Met Pro Leu Asp Val Gln Ala Asp Arg Glu Asp Ser
    2370                2375                2380
Arg Glu
2385

<210> SEQ ID NO 2
<211> LENGTH: 328
<212> TYPE: PRT
<213> ORGANISM: Homo sapiens

<400> SEQUENCE: 2

Met Leu Pro Arg Val Gly Cys Pro Ala Leu Pro Leu Pro Pro Pro Pro
1               5                   10                  15
Leu Leu Pro Leu Leu Pro Leu Leu Leu Leu Leu Leu Gly Ala Ser Gly
```

-continued

```
                20                  25                  30
Gly Gly Gly Gly Ala Arg Ala Glu Val Leu Phe Arg Cys Pro Pro Cys
                35                  40                  45

Thr Pro Glu Arg Leu Ala Ala Cys Gly Pro Pro Val Ala Pro Pro
 50                  55                  60

Ala Ala Val Ala Ala Val Ala Gly Gly Ala Arg Met Pro Cys Ala Glu
 65                  70                  75                  80

Leu Val Arg Glu Pro Gly Cys Gly Cys Cys Ser Val Cys Ala Arg Leu
                85                  90                  95

Glu Gly Glu Ala Cys Gly Val Tyr Thr Pro Arg Cys Gly Gln Gly Leu
                100                 105                 110

Arg Cys Tyr Pro His Pro Gly Ser Glu Leu Pro Leu Gln Ala Leu Val
                115                 120                 125

Met Gly Glu Gly Thr Cys Glu Lys Arg Arg Asp Ala Glu Tyr Gly Ala
                130                 135                 140

Ser Pro Glu Gln Val Ala Asp Asn Gly Asp Asp His Ser Glu Gly Gly
145                 150                 155                 160

Leu Val Glu Asn His Val Asp Ser Thr Met Asn Met Leu Gly Gly Gly
                165                 170                 175

Gly Ser Ala Gly Arg Lys Pro Leu Lys Ser Gly Met Lys Glu Leu Ala
                180                 185                 190

Val Phe Arg Glu Lys Val Thr Glu Gln His Arg Gln Met Gly Lys Gly
                195                 200                 205

Gly Lys His His Leu Gly Leu Glu Glu Pro Lys Lys Leu Arg Pro Pro
                210                 215                 220

Pro Ala Arg Thr Pro Cys Gln Gln Glu Leu Asp Gln Val Leu Glu Arg
225                 230                 235                 240

Ile Ser Thr Met Arg Leu Pro Asp Glu Arg Gly Pro Leu Glu His Leu
                245                 250                 255

Tyr Ser Leu His Ile Pro Asn Cys Asp Lys His Gly Leu Tyr Asn Leu
                260                 265                 270

Lys Gln Cys Lys Met Ser Leu Asn Gly Gln Arg Gly Glu Cys Trp Cys
                275                 280                 285

Val Asn Pro Asn Thr Gly Lys Leu Ile Gln Gly Ala Pro Thr Ile Arg
290                 295                 300

Gly Asp Pro Glu Cys His Leu Phe Tyr Asn Glu Gln Gln Glu Ala Arg
305                 310                 315                 320

Gly Val His Thr Gln Arg Met Gln
                325

<210> SEQ ID NO 3
<211> LENGTH: 1070
<212> TYPE: PRT
<213> ORGANISM: Homo sapiens

<400> SEQUENCE: 3

Met Gly Ala Ala Arg Gly Ser Pro Ala Arg Pro Arg Arg Leu Pro Leu
 1                   5                  10                  15

Leu Ser Val Leu Leu Leu Pro Leu Leu Gly Gly Thr Gln Thr Ala Ile
                20                  25                  30

Val Phe Ile Lys Gln Pro Ser Ser Gln Asp Ala Leu Gln Gly Arg Arg
                35                  40                  45

Ala Leu Leu Arg Cys Glu Val Glu Ala Pro Gly Pro Val His Val Tyr
 50                  55                  60
```

-continued

```
Trp Leu Leu Asp Gly Ala Pro Val Gln Asp Thr Glu Arg Arg Phe Ala
 65                  70                  75                  80

Gln Gly Ser Ser Leu Ser Phe Ala Ala Val Asp Pro Leu Gln Asp Ser
                 85                  90                  95

Gly Thr Phe Gln Cys Val Ala Arg Asp Asp Val Thr Gly Glu Glu Ala
            100                 105                 110

Arg Ser Ala Asn Ala Ser Phe Asn Ile Lys Trp Ile Glu Ala Gly Pro
        115                 120                 125

Val Val Leu Lys His Pro Ala Ser Glu Ala Glu Ile Gln Pro Gln Thr
    130                 135                 140

Gln Val Lys Leu Arg Cys His Ile Asp Gly His Pro Arg Pro Thr Tyr
145                 150                 155                 160

Gln Trp Phe Arg Asp Gly Thr Pro Leu Ser Asp Gly Gln Ser Asn His
                165                 170                 175

Thr Val Ser Ser Lys Glu Arg Asn Leu Thr Leu Arg Pro Ala Gly Pro
            180                 185                 190

Glu His Ser Gly Leu Tyr Ser Cys Cys Ala His Ser Ala Phe Ser Gln
        195                 200                 205

Ala Cys Ser Ser Gln Asn Phe Thr Leu Ser Ile Ala Asp Glu Ser Phe
    210                 215                 220

Ala Arg Val Val Leu Ala Pro Gln Asp Val Val Ala Arg Tyr Glu
225                 230                 235                 240

Glu Ala Met Phe His Cys Gln Phe Ser Ala Gln Pro Pro Ser Leu
                245                 250                 255

Gln Trp Leu Phe Glu Asp Glu Thr Pro Ile Thr Asn Arg Ser Arg Pro
            260                 265                 270

Pro His Leu Arg Arg Ala Thr Val Phe Ala Asn Gly Ser Leu Leu Leu
        275                 280                 285

Thr Gln Val Arg Pro Arg Asn Ala Gly Ile Tyr Arg Cys Ile Gly Gln
    290                 295                 300

Gly Gln Arg Gly Pro Pro Ile Ile Leu Glu Ala Thr Leu His Leu Ala
305                 310                 315                 320

Glu Ile Glu Asp Met Pro Leu Phe Glu Pro Arg Val Phe Thr Ala Gly
                325                 330                 335

Ser Glu Glu Arg Val Thr Cys Leu Pro Pro Lys Gly Leu Pro Glu Pro
            340                 345                 350

Ser Val Trp Trp Glu His Ala Gly Val Arg Leu Pro Thr His Gly Arg
        355                 360                 365

Val Tyr Gln Lys Gly His Glu Leu Val Leu Ala Asn Ile Ala Glu Ser
    370                 375                 380

Asp Ala Gly Val Tyr Thr Cys His Ala Ala Asn Leu Ala Gly Gln Arg
385                 390                 395                 400

Arg Gln Asp Val Asn Ile Thr Val Ala Thr Val Pro Ser Trp Leu Lys
                405                 410                 415

Lys Pro Gln Asp Ser Gln Leu Glu Glu Gly Lys Pro Gly Tyr Leu Asp
            420                 425                 430

Cys Leu Thr Gln Ala Thr Pro Lys Pro Thr Val Val Trp Tyr Arg Asn
        435                 440                 445

Gln Met Leu Ile Ser Glu Asp Ser Arg Phe Glu Val Phe Lys Asn Gly
    450                 455                 460

Thr Leu Arg Ile Asn Ser Val Glu Val Tyr Asp Gly Thr Trp Tyr Arg
465                 470                 475                 480

Cys Met Ser Ser Thr Pro Ala Gly Ser Ile Glu Ala Gln Ala Val Leu
```

-continued

```
                485                 490                 495
Gln Val Leu Glu Lys Leu Lys Phe Thr Pro Pro Gln Pro Gln Gln
            500                 505                 510
Cys Met Gly Phe Asp Lys Glu Ala Thr Val Pro Cys Ser Ala Thr Gly
        515                 520                 525
Arg Glu Lys Pro Thr Ile Lys Trp Glu Arg Ala Asp Gly Ser Ser Leu
    530                 535                 540
Pro Glu Trp Val Thr Asp Asn Ala Gly Thr Leu His Phe Ala Arg Val
545                 550                 555                 560
Thr Arg Asp Asp Ala Gly Asn Tyr Thr Cys Ile Ala Ser Asn Gly Pro
                565                 570                 575
Gln Gly Gln Ile Arg Ala His Val Gln Leu Thr Val Ala Val Phe Ile
            580                 585                 590
Thr Phe Lys Val Glu Pro Glu Arg Thr Thr Val Tyr Gln Gly His Thr
        595                 600                 605
Ala Leu Leu Gln Cys Glu Ala Gln Gly Asp Pro Lys Pro Leu Ile Gln
    610                 615                 620
Trp Lys Gly Lys Asp Arg Ile Leu Asp Pro Thr Lys Leu Gly Pro Arg
625                 630                 635                 640
Met His Ile Phe Gln Asn Gly Ser Leu Val Ile His Asp Val Ala Pro
                645                 650                 655
Glu Asp Ser Gly Arg Tyr Thr Cys Ile Ala Gly Asn Ser Cys Asn Ile
            660                 665                 670
Lys His Thr Glu Ala Pro Leu Tyr Val Val Asp Lys Pro Val Pro Glu
        675                 680                 685
Glu Ser Glu Gly Pro Gly Ser Pro Pro Tyr Lys Met Ile Gln Thr
    690                 695                 700
Ile Gly Leu Ser Val Gly Ala Ala Val Ala Tyr Ile Ile Ala Val Leu
705                 710                 715                 720
Gly Leu Met Phe Tyr Cys Lys Lys Arg Cys Lys Ala Lys Arg Leu Gln
                725                 730                 735
Lys Gln Pro Glu Gly Glu Glu Pro Glu Met Glu Cys Leu Asn Gly Gly
            740                 745                 750
Pro Leu Gln Asn Gly Gln Pro Ser Ala Glu Ile Gln Glu Glu Val Ala
        755                 760                 765
Leu Thr Ser Leu Gly Ser Gly Pro Ala Ala Thr Asn Lys Arg His Ser
    770                 775                 780
Thr Ser Asp Lys Met His Phe Pro Arg Ser Ser Leu Gln Pro Ile Thr
785                 790                 795                 800
Thr Leu Gly Lys Ser Glu Phe Gly Glu Val Phe Leu Ala Lys Ala Gln
                805                 810                 815
Gly Leu Glu Glu Gly Val Ala Glu Thr Leu Val Leu Val Lys Ser Leu
            820                 825                 830
Gln Ser Lys Asp Glu Gln Gln Leu Asp Phe Arg Arg Glu Leu Glu
        835                 840                 845
Met Phe Gly Lys Leu Asn His Ala Asn Val Val Arg Leu Leu Gly Leu
    850                 855                 860
Cys Arg Glu Ala Glu Pro His Tyr Met Val Leu Glu Tyr Val Asp Leu
865                 870                 875                 880
Glu Asp Leu Lys Gln Phe Leu Arg Ile Ser Lys Ser Lys Asp Glu Lys
                885                 890                 895
Leu Lys Ser Gln Pro Leu Ser Thr Lys Gln Lys Val Ala Leu Cys Thr
            900                 905                 910
```

```
Gln Val Ala Leu Gly Met Glu His Leu Ser Asn Asn Arg Phe Val His
            915                 920                 925

Lys Asp Leu Ala Ala Arg Asn Cys Leu Val Ser Ala Gln Arg Gln Val
    930                 935                 940

Lys Val Ser Ala Leu Gly Leu Ser Lys Asp Val Tyr Asn Ser Glu Tyr
945                 950                 955                 960

Tyr His Phe Arg Gln Ala Trp Val Ala Leu Arg Trp Met Ser Pro Glu
                965                 970                 975

Ala Ile Leu Glu Gly Asp Phe Ser Thr Lys Ser Asp Val Trp Ala Ser
            980                 985                 990

Gly Val Leu Met Trp Glu Val Phe Thr His Gly Glu Met Pro His Gly
            995                 1000                1005

Gly Gln Ala Asp Asp Glu Val Leu Ala Asp Leu Gln Ala Gly Lys Ala
    1010                1015                1020

Arg Leu Pro Gln Pro Glu Gly Cys Pro Ser Lys Leu Tyr Arg Leu Met
1025                1030                1035                1040

Gln Arg Cys Trp Ala Leu Ser Pro Lys Asp Arg Pro Ser Phe Ser Glu
                1045                1050                1055

Ile Ala Ser Ala Leu Gly Asp Ser Thr Val Asp Ser Lys Pro
            1060                1065                1070

<210> SEQ ID NO 4
<211> LENGTH: 1088
<212> TYPE: PRT
<213> ORGANISM: Homo sapiens

<400> SEQUENCE: 4

Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
```

-continued

```
                        210                 215                 220
Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Ile Lys Val Pro Ser Ile Lys Leu Val
            260                 265                 270

Tyr Thr Leu Thr Val Pro Glu Ala Thr Val Lys Asp Ser Gly Asp Tyr
            275                 280                 285

Glu Cys Ala Ala Arg Gln Ala Thr Arg Glu Val Lys Glu Met Lys Lys
290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
                325                 330                 335

Val Glu Val Arg Ala Tyr Pro Pro Arg Ile Ser Trp Leu Lys Asn
            340                 345                 350

Asn Leu Thr Leu Ile Glu Asn Leu Thr Glu Ile Thr Thr Asp Val Glu
            355                 360                 365

Lys Ile Gln Glu Ile Arg Tyr Arg Ser Lys Leu Lys Leu Ile Arg Ala
370                 375                 380

Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
                405                 410                 415

Ile Leu Asp Leu Val Asp Asp His His Gly Ser Thr Gly Gly Gln Thr
            420                 425                 430

Val Arg Cys Thr Ala Glu Gly Thr Pro Leu Pro Asp Ile Glu Trp Met
            435                 440                 445

Ile Cys Lys Asp Ile Lys Lys Cys Asn Asn Glu Thr Ser Trp Thr Ile
            450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
                485                 490                 495

Ile Ala Val Arg Cys Leu Ala Lys Asn Leu Leu Gly Ala Glu Asn Arg
            500                 505                 510

Glu Leu Lys Leu Val Ala Pro Thr Leu Arg Ser Glu Leu Thr Val Ala
            515                 520                 525

Ala Ala Val Leu Val Leu Leu Val Ile Val Ile Ile Ser Leu Ile Val
530                 535                 540

Leu Val Val Ile Trp Lys Gln Lys Pro Arg Tyr Glu Ile Arg Trp Arg
545                 550                 555                 560

Val Ile Glu Ser Ile Ser Pro Asp Gly His Glu Tyr Ile Tyr Val Asp
                565                 570                 575

Pro Met Gln Leu Pro Tyr Asp Ser Arg Trp Glu Phe Pro Arg Asp Gly
            580                 585                 590

Leu Val Leu Gly Arg Val Leu Gly Ser Gly Ala Phe Gly Lys Val Val
            595                 600                 605

Glu Gly Thr Ala Tyr Gly Leu Ser Arg Ser Gln Pro Val Met Lys Val
            610                 615                 620

Ala Val Lys Met Leu Lys Pro Thr Ala Arg Ser Ser Glu Lys Gln Ala
625                 630                 635                 640
```

```
Leu Met Ser Glu Leu Lys Ile Met Thr His Leu Gly Pro His Leu Asn
                645                 650                 655

Ile Val Asn Leu Leu Gly Ala Cys Thr Lys Ser Gly Pro Ile Tyr Ile
            660                 665                 670

Ile Thr Glu Tyr Cys Phe Tyr Gly Asp Leu Val Asn Tyr Leu His Lys
        675                 680                 685

Asn Arg Asp Ser Phe Leu Ser His His Pro Glu Lys Pro Lys Lys Glu
    690                 695                 700

Leu Asp Ile Phe Gly Leu Asn Pro Ala Asp Glu Ser Thr Arg Ser Tyr
705                 710                 715                 720

Val Ile Leu Ser Phe Glu Asn Asn Gly Asp Tyr Met Asp Met Lys Gln
                725                 730                 735

Ala Asp Thr Thr Gln Tyr Val Pro Met Leu Glu Arg Lys Glu Val Ser
            740                 745                 750

Lys Tyr Ser Asp Ile Gln Arg Ser Leu Tyr Asp Arg Pro Ala Ser Tyr
        755                 760                 765

Lys Lys Lys Ser Met Leu Asp Ser Glu Val Lys Asn Leu Leu Ser Asp
    770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
                805                 810                 815

Arg Asp Leu Ala Ala Arg Asn Val Leu Leu Ala Gln Gly Lys Ile Val
            820                 825                 830

Lys Ile Cys Asp Phe Gly Leu Ala Arg Asp Ile Met His Asp Ser Asn
        835                 840                 845

Tyr Val Ser Lys Gly Ser Thr Phe Leu Pro Val Lys Trp Met Ala Pro
    850                 855                 860

Glu Ser Ile Phe Asp Asn Leu Tyr Thr Thr Leu Ser Asp Val Trp Ser
865                 870                 875                 880

Tyr Gly Ile Leu Leu Trp Glu Ile Phe Ser Leu Gly Gly Thr Pro Tyr
                885                 890                 895

Pro Gly Met Met Val Asp Ser Thr Phe Tyr Asn Lys Ile Lys Ser Gly
            900                 905                 910

Tyr Arg Met Ala Lys Pro Asp His Ala Thr Ser Glu Val Tyr Glu Ile
        915                 920                 925

Met Val Lys Cys Trp Asn Ser Glu Pro Glu Lys Arg Pro Ser Phe Tyr
    930                 935                 940

His Leu Ser Glu Ile Val Glu Asn Leu Leu Pro Gly Gln Tyr Lys Lys
945                 950                 955                 960

Ser Tyr Glu Lys Ile His Leu Asp Phe Leu Lys Ser Asp His Pro Ala
                965                 970                 975

Val Ala Arg Met Val Asp Ser Asp Asn Ala Tyr Ile Gly Val Thr Tyr
            980                 985                 990

Lys Asn Glu Glu Asp Lys Leu Lys Asp Trp Glu Gly Gly Leu Asp Glu
        995                 1000                1005

Gln Arg Leu Ser Ala Asp Ser Gly Tyr Ile Ile Pro Leu Pro Asp Ile
    1010                1015                1020

Asp Pro Val Pro Glu Glu Glu Asp Leu Gly Lys Arg Asn Arg His Ser
1025                1030                1035                1040

Ser Gln Thr Ser Glu Glu Ser Ala Ile Glu Thr Gly Ser Ser Ser Ser
                1045                1050                1055
```

```
Thr Phe Ile Lys Arg Glu Asp Glu Thr Ile Glu Asp Ile Asp Met Met
            1060                1065                1070

Asp Asp Ile Gly Ile Asp Ser Ser Asp Leu Val Glu Asp Ser Phe Leu
            1075                1080                1085

<210> SEQ ID NO 5
<211> LENGTH: 684
<212> TYPE: PRT
<213> ORGANISM: Homo sapiens

<400> SEQUENCE: 5

Gly Glu Val Gly Ala Asp Gly Ile Pro Gly Phe Pro Gly Leu Pro Gly
 1               5                  10                  15

Arg Glu Gly Ile Ala Gly Pro Gln Gly Pro Lys Gly Asp Arg Gly Ser
            20                  25                  30

Arg Gly Glu Lys Gly Asp Pro Gly Lys Asp Gly Leu Gly Gln Pro Gly
        35                  40                  45

Leu Pro Gly Pro Arg Gly Pro Pro Gly Pro Val Val Tyr Val Ser Glu
    50                  55                  60

Gln Asp Gly Ser Val Leu Ser Val Pro Gly Pro Glu Gly Arg Arg Gly
 65                 70                  75                  80

Phe Ala Gly Phe Pro Gly Pro Ala Gly Pro Lys Gly Asn Leu Gly Ser
                85                  90                  95

Lys Gly Glu Leu Gly Ser Pro Gly Pro Lys Gly Glu Lys Gly Glu Pro
            100                 105                 110

Gly Ser Ile Phe Ser Pro Asp Gly Gly Ala Leu Gly Pro Ala Gln Lys
        115                 120                 125

Gly Ala Lys Gly Glu Pro Gly Phe Arg Gly Pro Pro Gly Leu Tyr Gly
    130                 135                 140

Arg Pro Gly Tyr Lys Gly Glu Ile Gly Phe Pro Gly Arg Pro Gly Arg
145                 150                 155                 160

Pro Gly Met Asn Gly Leu Lys Gly Glu Lys Gly Glu Pro Gly Asp Ala
                165                 170                 175

Ser Leu Gly Phe Gly Met Arg Gly Met Pro Gly Pro Pro Gly Pro Pro
            180                 185                 190

Gly Pro Pro Gly Pro Pro Gly Thr Pro Val Tyr Asp Ser Asn Val Phe
        195                 200                 205

Ala Glu Ser Ser Arg Pro Gly Pro Pro Gly Leu Pro Gly Asn Gln Gly
    210                 215                 220

Pro Pro Gly Pro Lys Gly Pro Lys Gly Glu Val Gly Pro Pro Gly Pro
225                 230                 235                 240

Pro Gly Gln Phe Pro Phe Asp Phe Leu Gln Lys Glu Ala Glu Met Lys
                245                 250                 255

Gly Glu Lys Gly Asp Arg Gly Asp Ala Gly Gln Lys Gly Glu Arg Gly
            260                 265                 270

Glu Pro Gly Gly Gly Phe Phe Gly Ser Ser Leu Pro Gly Ala Pro
        275                 280                 285

Gly Ala Pro Gly Pro Arg Gly Tyr Pro Gly Ile Pro Gly Pro Lys Gly
    290                 295                 300

Glu Ser Ile Arg Gly Gln Pro Gly Pro Pro Gly Pro Gln Gly Pro Pro
305                 310                 315                 320

Gly Ile Gly Tyr Glu Gly Arg Gln Gly Pro Pro Gly Pro Pro Gly Pro
                325                 330                 335

Pro Gly Pro Pro Ser Phe Pro Gly Pro His Arg Gln Thr Ile Ser Val
            340                 345                 350
```

```
Pro Gly Pro Pro Gly Pro Pro Gly Pro Pro Gly Thr Met
        355                 360                 365

Gly Ala Ser Ser Gly Gln Val Arg Leu Trp Ala Thr Arg Gln Ala Met
        370                 375                 380

Leu Gly Gln Val His Glu Val Pro Glu Gly Trp Leu Ile Phe Val Ala
385                 390                 395                 400

Glu Gln Glu Glu Leu Tyr Val Arg Val Gln Asn Gly Phe Arg Lys Val
                405                 410                 415

Gln Leu Glu Ala Arg Thr Pro Leu Pro Arg Gly Thr Asp Asn Glu Val
                420                 425                 430

Ala Ala Leu Gln Pro Pro Val Val Gln Leu His Asp Ser Asn Pro Tyr
            435                 440                 445

Pro Arg Arg Glu His Pro His Pro Thr Ala Arg Pro Trp Arg Ala Asp
        450                 455                 460

Asp Ile Leu Ala Ser Pro Pro Gly Leu Pro Glu Pro Gln Pro Tyr Pro
465                 470                 475                 480

Gly Gly Pro His His Ser Ser Tyr Val His Cys Gly Pro Ala Arg Pro
                485                 490                 495

Thr Ser Pro Pro Ala His Ser His Arg Asp Phe Gln Pro Val Leu His
                500                 505                 510

Leu Val Ala Leu Asn Ser Pro Leu Ser Gly Gly Met Arg Gly Ile Arg
            515                 520                 525

Gly Ala Asp Phe Gln Cys Phe Gln Gln Ala Arg Ala Val Gly Leu Ala
        530                 535                 540

Gly Thr Phe Arg Ala Phe Leu Ser Ser Arg Leu Gln Asp Leu Tyr Ser
545                 550                 555                 560

Ile Val Arg Arg Ala Asp Arg Ala Ala Val Pro Ile Val Asn Leu Lys
                565                 570                 575

Asp Glu Leu Leu Phe Pro Ser Trp Glu Ala Leu Phe Ser Gly Ser Glu
            580                 585                 590

Gly Pro Leu Lys Pro Gly Ala Arg Ile Phe Ser Phe Asp Gly Lys Asp
        595                 600                 605

Val Leu Arg His Pro Thr Trp Pro Gln Lys Ser Val Trp His Gly Ser
610                 615                 620

Asp Pro Asn Gly Arg Arg Leu Thr Glu Ser Tyr Cys Glu Thr Trp Arg
625                 630                 635                 640

Thr Glu Ala Pro Ser Ala Thr Gly Gln Ala Ser Ser Leu Leu Gly Gly
                645                 650                 655

Arg Leu Leu Gly Gln Ser Ala Ala Ser Cys His His Ala Tyr Ile Val
            660                 665                 670

Leu Cys Ile Glu Asn Ser Phe Met Thr Ala Ser Lys
        675                 680

<210> SEQ ID NO 6
<211> LENGTH: 969
<212> TYPE: PRT
<213> ORGANISM: Homo sapiens

<400> SEQUENCE: 6

Met Pro Pro Arg Ala Pro Pro Ala Pro Gly Pro Arg Pro Pro Pro Arg
 1               5                  10                  15

Ala Ala Ala Ala Thr Asp Thr Ala Ala Gly Ala Gly Ala Gly Ala Gly
                20                  25                  30

Ala Gly Gly Ala Gly Gly Pro Gly Phe Arg Pro Leu Ala Pro Arg Pro
```

```
                35                  40                  45
Trp Arg Trp Leu Leu Leu Ala Leu Pro Ala Ala Cys Ser Ala Pro
 50                  55                  60

Pro Pro Arg Pro Val Tyr Thr Asn His Trp Ala Val Gln Val Leu Gly
 65                  70                  75                  80

Gly Pro Ala Glu Ala Asp Arg Val Ala Ala His Gly Tyr Leu Asn
                 85                  90                  95

Leu Gly Gln Ile Gly Asn Leu Glu Asp Tyr Tyr His Phe Tyr His Ser
                100                 105                 110

Lys Thr Phe Lys Arg Ser Thr Leu Ser Ser Arg Gly Pro His Thr Phe
                115                 120                 125

Leu Arg Met Asp Pro Gln Val Lys Trp Leu Gln Gln Gln Glu Val Lys
130                 135                 140

Arg Arg Val Lys Arg Gln Val Arg Ser Asp Pro Gln Ala Leu Tyr Phe
145                 150                 155                 160

Asn Asp Pro Ile Trp Ser Asn Met Trp Tyr Leu His Cys Gly Asp Lys
                165                 170                 175

Asn Ser Arg Cys Arg Ser Glu Met Asn Val Gln Ala Ala Trp Lys Arg
                180                 185                 190

Gly Tyr Thr Gly Lys Asn Val Val Thr Ile Leu Asp Asp Gly Ile
                195                 200                 205

Glu Arg Asn His Pro Asp Leu Ala Pro Asn Tyr Asp Ser Tyr Ala Ser
                210                 215                 220

Tyr Asp Val Asn Gly Asn Asp Tyr Asp Pro Ser Pro Arg Tyr Asp Ala
225                 230                 235                 240

Ser Asn Glu Asn Lys His Gly Thr Arg Cys Ala Gly Glu Val Ala Ala
                245                 250                 255

Ser Ala Asn Asn Ser Tyr Cys Ile Val Gly Ile Ala Tyr Asn Ala Lys
                260                 265                 270

Ile Gly Gly Ile Arg Met Leu Asp Gly Asp Val Thr Asp Val Val Glu
                275                 280                 285

Ala Lys Ser Leu Gly Ile Arg Pro Asn Tyr Ile Asp Ile Tyr Ser Ala
290                 295                 300

Ser Trp Gly Pro Asp Asp Asp Gly Lys Thr Val Asp Gly Pro Gly Arg
305                 310                 315                 320

Leu Ala Lys Gln Ala Phe Glu Tyr Gly Ile Lys Lys Gly Arg Gln Gly
                325                 330                 335

Leu Gly Ser Ile Phe Val Trp Ala Ser Gly Asn Gly Gly Arg Glu Gly
                340                 345                 350

Asp Tyr Cys Ser Cys Asp Gly Tyr Thr Asn Ser Ile Tyr Thr Ile Ser
                355                 360                 365

Val Ser Ser Ala Thr Glu Asn Gly Tyr Lys Pro Trp Tyr Leu Glu Glu
370                 375                 380

Cys Ala Ser Thr Leu Ala Thr Thr Tyr Ser Ser Gly Ala Phe Tyr Glu
385                 390                 395                 400

Arg Lys Ile Val Thr Thr Asp Leu Arg Gln Arg Cys Thr Asp Gly His
                405                 410                 415

Thr Gly Thr Ser Val Ser Ala Pro Met Val Ala Gly Ile Ile Ala Leu
                420                 425                 430

Ala Leu Glu Ala Asn Ser Gln Leu Thr Trp Arg Asp Val Gln His Leu
                435                 440                 445

Leu Val Lys Thr Ser Arg Pro Ala His Leu Lys Ala Ser Asp Trp Lys
450                 455                 460
```

-continued

```
Val Asn Gly Ala Gly His Lys Val Ser His Phe Tyr Gly Phe Gly Leu
465                 470                 475                 480

Val Asp Ala Glu Ala Leu Val Glu Ala Lys Lys Trp Thr Ala Val
            485                 490                 495

Pro Ser Gln His Met Cys Val Ala Ala Ser Asp Lys Arg Pro Arg Ser
                500                 505                 510

Ile Pro Leu Val Gln Val Leu Arg Thr Thr Ala Leu Thr Ser Ala Cys
            515                 520                 525

Ala Glu His Ser Asp Gln Arg Val Val Tyr Leu Glu His Val Val Val
        530                 535                 540

Arg Thr Ser Ile Ser His Pro Arg Arg Gly Asp Leu Gln Ile Tyr Leu
545                 550                 555                 560

Val Ser Pro Ser Gly Thr Lys Ser Gln Leu Leu Ala Lys Arg Leu Leu
                565                 570                 575

Asp Leu Ser Asn Glu Gly Phe Thr Asn Trp Glu Phe Met Thr Val His
            580                 585                 590

Cys Trp Gly Glu Lys Ala Glu Gly Gln Trp Thr Leu Glu Ile Gln Asp
            595                 600                 605

Leu Pro Ser Gln Val Arg Asn Pro Glu Lys Gln Gly Lys Leu Lys Glu
        610                 615                 620

Trp Ser Leu Ile Leu Tyr Gly Thr Ala Glu His Pro Tyr His Thr Phe
625                 630                 635                 640

Ser Ala His Gln Ser Arg Ser Arg Met Leu Glu Leu Ser Ala Pro Glu
                645                 650                 655

Leu Glu Pro Pro Lys Ala Ala Leu Ser Pro Ser Gln Val Glu Val Pro
            660                 665                 670

Glu Asp Glu Glu Asp Tyr Thr Ala Gln Ser Thr Pro Gly Ser Ala Asn
        675                 680                 685

Ile Leu Gln Thr Ser Val Cys His Pro Glu Cys Gly Asp Lys Gly Cys
        690                 695                 700

Asp Gly Pro Asn Ala Asp Gln Cys Leu Asn Cys Val His Phe Ser Leu
705                 710                 715                 720

Gly Ser Val Lys Thr Ser Arg Lys Cys Val Ser Val Cys Pro Leu Gly
                725                 730                 735

Tyr Phe Gly Asp Thr Ala Ala Arg Arg Cys Arg Arg Cys His Lys Gly
            740                 745                 750

Cys Glu Thr Cys Ser Ser Arg Ala Ala Thr Gln Cys Leu Ser Cys Arg
        755                 760                 765

Arg Gly Phe Tyr His His Gln Glu Met Asn Thr Cys Val Thr Leu Cys
770                 775                 780

Pro Ala Gly Phe Tyr Ala Asp Glu Ser Gln Lys Asn Cys Leu Lys Cys
785                 790                 795                 800

His Pro Ser Cys Lys Lys Cys Val Asp Glu Pro Glu Lys Cys Thr Val
                805                 810                 815

Cys Lys Glu Gly Phe Ser Leu Ala Arg Gly Ser Cys Ile Pro Asp Cys
            820                 825                 830

Glu Pro Gly Thr Tyr Phe Asp Ser Glu Leu Ile Arg Cys Gly Glu Cys
        835                 840                 845

His His Thr Cys Gly Thr Cys Val Gly Pro Gly Arg Glu Glu Cys Ile
        850                 855                 860

His Cys Ala Lys Asn Phe His Phe His Asp Trp Lys Cys Val Pro Ala
865                 870                 875                 880
```

-continued

```
Cys Gly Glu Gly Phe Tyr Pro Glu Glu Met Pro Gly Leu Pro His Lys
                885                 890                 895

Val Cys Arg Arg Cys Asp Glu Asn Cys Leu Ser Cys Ala Gly Ser Ser
            900                 905                 910

Arg Asn Cys Ser Arg Cys Lys Thr Gly Phe Thr Gln Leu Gly Thr Ser
        915                 920                 925

Cys Ile Thr Asn His Thr Cys Ser Asn Ala Asp Glu Thr Phe Cys Glu
    930                 935                 940

Met Val Lys Ser Asn Arg Leu Cys Glu Arg Lys Leu Phe Ile Gln Phe
945                 950                 955                 960

Cys Cys Arg Thr Cys Leu Leu Ala Gly
                965

<210> SEQ ID NO 7
<211> LENGTH: 3070
<212> TYPE: PRT
<213> ORGANISM: Homo sapiens

<400> SEQUENCE: 7

Met Pro Gly Ala Ala Gly Val Leu Leu Leu Leu Leu Ser Gly Gly Gly
1               5                   10                  15

Leu Gly Gly Val Gln Ala Gln Arg Pro Gln Gln Gln Arg Gln Ser Gln
            20                  25                  30

Ala His Gln Gln Arg Gly Leu Phe Pro Ala Val Leu Asn Leu Ala Ser
        35                  40                  45

Asn Ala Leu Ile Thr Thr Asn Ala Thr Cys Gly Glu Lys Gly Pro Glu
    50                  55                  60

Met Tyr Cys Lys Leu Val Glu His Val Pro Gly Gln Pro Val Arg Asn
65                  70                  75                  80

Pro Gln Cys Arg Ile Cys Asn Gln Asn Ser Asn Pro Asn Gln Arg
                85                  90                  95

His Pro Ile Thr Asn Ala Ile Asp Gly Lys Asn Thr Trp Trp Gln Ser
            100                 105                 110

Pro Ser Ile Lys Asn Gly Ile Glu Tyr His Tyr Val Thr Ile Thr Leu
        115                 120                 125

Asp Leu Gln Gln Val Phe Gln Ile Ala Tyr Val Ile Val Lys Ala Ala
    130                 135                 140

Asn Ser Pro Arg Pro Gly Asn Trp Ile Leu Glu Arg Ser Leu Asp Asp
145                 150                 155                 160

Val Glu Tyr Lys Pro Trp Gln Tyr His Ala Val Thr Asp Thr Glu Cys
                165                 170                 175

Leu Thr Leu Tyr Asn Ile Tyr Pro Arg Thr Gly Pro Pro Ser Tyr Ala
            180                 185                 190

Lys Asp Asp Glu Val Ile Cys Thr Ser Phe Tyr Ser Lys Ile His Pro
        195                 200                 205

Leu Glu Asn Gly Glu Ile His Ile Ser Leu Ile Asn Gly Arg Pro Ser
    210                 215                 220

Ala Asp Asp Pro Ser Pro Glu Leu Leu Glu Phe Thr Ser Ala Arg Tyr
225                 230                 235                 240

Ile Arg Leu Arg Phe Gln Arg Ile Arg Thr Leu Asn Ala Asp Leu Met
                245                 250                 255

Met Phe Ala His Lys Asp Pro Arg Glu Ile Asp Pro Ile Val Thr Arg
            260                 265                 270

Arg Tyr Tyr Tyr Ser Val Lys Asp Ile Ser Val Gly Gly Met Cys Ile
        275                 280                 285
```

-continued

Cys Tyr Gly His Ala Arg Ala Cys Pro Leu Asp Pro Ala Thr Asn Lys
        290                 295                 300

Ser Arg Cys Glu Cys Glu His Asn Thr Cys Gly Asp Ser Cys Asp Gln
305                 310                 315                 320

Cys Cys Pro Gly Phe His Gln Lys Pro Trp Arg Ala Gly Thr Phe Leu
                325                 330                 335

Thr Lys Thr Glu Cys Glu Ala Cys Asn Cys His Gly Lys Ala Glu Glu
            340                 345                 350

Cys Tyr Tyr Asp Glu Asn Val Ala Arg Arg Asn Leu Ser Leu Asn Ile
        355                 360                 365

Arg Gly Lys Tyr Ile Gly Gly Val Cys Ile Asn Cys Thr Gln Asn
    370                 375                 380

Thr Ala Gly Ile Asn Cys Glu Thr Cys Thr Asp Gly Phe Phe Arg Pro
385                 390                 395                 400

Lys Gly Val Ser Pro Asn Tyr Pro Arg Pro Cys Gln Pro Cys His Cys
                405                 410                 415

Asp Pro Ile Gly Ser Leu Asn Glu Val Cys Val Lys Asp Glu Lys His
            420                 425                 430

Ala Arg Arg Gly Leu Ala Pro Gly Ser Cys His Cys Lys Thr Gly Phe
        435                 440                 445

Gly Gly Val Ser Cys Asp Arg Cys Ala Arg Gly Tyr Thr Gly Tyr Pro
    450                 455                 460

Asp Cys Lys Ala Cys Asn Cys Ser Gly Leu Gly Ser Lys Asn Glu Asp
465                 470                 475                 480

Pro Cys Phe Gly Pro Cys Ile Cys Lys Glu Asn Val Glu Gly Gly Asp
                485                 490                 495

Cys Ser Arg Cys Lys Ser Gly Phe Phe Asn Leu Gln Glu Asp Asn Trp
            500                 505                 510

Lys Gly Cys Asp Glu Cys Phe Cys Ser Gly Val Ser Asn Arg Cys Gln
        515                 520                 525

Ser Ser Tyr Trp Thr Tyr Gly Lys Ile Gln Asp Met Ser Gly Trp Tyr
    530                 535                 540

Leu Thr Asp Leu Pro Gly Arg Ile Arg Val Ala Pro Gln Gln Asp Asp
545                 550                 555                 560

Leu Asp Ser Pro Gln Gln Ile Ser Ile Ser Asn Ala Glu Ala Arg Gln
                565                 570                 575

Ala Leu Pro His Ser Tyr Tyr Trp Ser Ala Pro Ala Pro Tyr Leu Gly
            580                 585                 590

Asn Lys Leu Pro Ala Val Gly Gly Gln Leu Thr Phe Thr Ile Ser Tyr
        595                 600                 605

Asp Leu Glu Glu Glu Glu Asp Thr Glu Arg Val Leu Gln Leu Met
    610                 615                 620

Ile Ile Leu Glu Gly Asn Asp Leu Ser Ile Ser Thr Ala Gln Asp Glu
625                 630                 635                 640

Val Tyr Leu His Pro Ser Glu Glu His Thr Asn Val Leu Leu Leu Lys
                645                 650                 655

Glu Glu Ser Phe Thr Ile His Gly Thr His Phe Pro Val Arg Arg Lys
            660                 665                 670

Glu Phe Met Thr Val Leu Ala Asn Leu Lys Arg Val Leu Leu Gln Ile
        675                 680                 685

Thr Tyr Ser Phe Gly Met Asp Ala Ile Phe Arg Leu Ser Ser Val Asn
    690                 695                 700

-continued

Leu Glu Ser Ala Val Ser Tyr Pro Thr Asp Gly Ser Ile Ala Ala Ala
705                 710                 715                 720

Val Glu Val Cys Gln Cys Pro Pro Gly Tyr Thr Gly Ser Ser Cys Glu
            725                 730                 735

Ser Cys Trp Pro Arg His Arg Val Asn Gly Thr Ile Phe Gly Gly
        740                 745                 750

Ile Cys Glu Pro Cys Gln Cys Phe Gly His Ala Glu Ser Cys Asp Asp
        755                 760                 765

Val Thr Gly Glu Cys Leu Asn Cys Lys Asp His Thr Gly Gly Pro Tyr
770                 775                 780

Cys Asp Lys Cys Leu Pro Gly Phe Tyr Gly Glu Pro Thr Lys Gly Thr
785                 790                 795                 800

Ser Glu Asp Cys Gln Pro Cys Ala Cys Pro Leu Asn Ile Pro Ser Asn
                805                 810                 815

Asn Phe Ser Pro Thr Cys His Leu Asp Arg Ser Leu Gly Leu Ile Cys
                820                 825                 830

Asp Gly Cys Pro Val Gly Tyr Thr Gly Pro Arg Cys Glu Arg Cys Ala
        835                 840                 845

Glu Gly Tyr Phe Gly Gln Pro Ser Val Pro Gly Gly Ser Cys Gln Pro
        850                 855                 860

Cys Gln Cys Asn Asp Asn Leu Asp Phe Ser Ile Pro Gly Ser Cys Asp
865                 870                 875                 880

Ser Leu Ser Gly Ser Cys Leu Ile Cys Lys Pro Gly Thr Thr Gly Arg
                885                 890                 895

Tyr Cys Glu Leu Cys Ala Asp Gly Tyr Phe Gly Asp Ala Val Asp Ala
            900                 905                 910

Lys Asn Cys Gln Pro Cys Arg Cys Asn Ala Gly Gly Ser Phe Ser Glu
            915                 920                 925

Val Cys His Ser Gln Thr Gly Gln Cys Glu Cys Arg Ala Asn Val Gln
930                 935                 940

Gly Gln Arg Cys Asp Lys Cys Lys Ala Gly Thr Phe Gly Leu Gln Ser
945                 950                 955                 960

Ala Arg Gly Cys Val Pro Cys Asn Cys Asn Ser Phe Gly Ser Lys Ser
                965                 970                 975

Phe Asp Cys Glu Glu Ser Gly Gln Cys Trp Cys Gln Pro Gly Val Thr
            980                 985                 990

Gly Lys Lys Cys Asp Arg Cys Ala His Gly Tyr Phe Asn Phe Gln Glu
            995                 1000                1005

Gly Gly Cys Thr Ala Cys Glu Cys Ser His Leu Gly Asn Asn Cys Asp
1010                1015                1020

Pro Lys Thr Gly Arg Cys Ile Cys Pro Pro Asn Thr Ile Gly Glu Lys
1025                1030                1035                1040

Cys Ser Lys Cys Ala Pro Asn Thr Trp Gly His Ser Ile Thr Thr Gly
                1045                1050                1055

Cys Lys Ala Cys Asn Cys Ser Thr Val Gly Ser Leu Asp Phe Gln Cys
            1060                1065                1070

Asn Val Asn Thr Gly Gln Cys Asn Cys His Pro Lys Phe Ser Gly Ala
            1075                1080                1085

Lys Cys Thr Glu Cys Ser Arg Gly His Trp Asn Tyr Pro Arg Cys Asn
            1090                1095                1100

Leu Cys Asp Cys Phe Leu Pro Gly Thr Asp Ala Thr Thr Cys Asp Ser
1105                1110                1115                1120

Glu Thr Lys Lys Cys Ser Cys Ser Asp Gln Thr Gly Gln Cys Thr Cys

-continued

```
                1125                1130                1135
Lys Val Asn Val Glu Gly Ile His Cys Asp Arg Cys Arg Pro Gly Lys
        1140                1145                1150
Phe Gly Leu Asp Ala Lys Asn Pro Leu Gly Cys Ser Ser Cys Tyr Cys
        1155                1160                1165
Phe Gly Thr Thr Thr Gln Cys Ser Glu Ala Lys Gly Leu Ile Arg Thr
        1170                1175                1180
Trp Val Thr Leu Lys Ala Glu Gln Thr Ile Leu Pro Leu Val Asp Glu
1185                1190                1195                1200
Ala Leu Gln His Thr Thr Thr Lys Gly Ile Val Phe Gln His Pro Glu
        1205                1210                1215
Ile Val Ala His Met Asp Leu Met Arg Glu Asp Leu His Leu Glu Pro
        1220                1225                1230
Phe Tyr Trp Lys Leu Pro Glu Gln Phe Glu Gly Lys Lys Leu Met Ala
        1235                1240                1245
Tyr Gly Gly Lys Leu Lys Tyr Ala Ile Tyr Phe Glu Ala Arg Glu Glu
        1250                1255                1260
Thr Gly Phe Ser Thr Tyr Asn Pro Gln Val Ile Ile Arg Gly Gly Thr
1265                1270                1275                1280
Pro Thr His Ala Arg Ile Ile Val Arg His Met Ala Ala Pro Leu Ile
        1285                1290                1295
Gly Gln Leu Thr Arg His Glu Ile Glu Met Thr Glu Lys Glu Trp Lys
        1300                1305                1310
Tyr Tyr Gly Asp Asp Pro Arg Val His Arg Thr Val Thr Arg Glu Asp
        1315                1320                1325
Phe Leu Asp Ile Leu Tyr Asp Ile His Tyr Ile Leu Ile Lys Ala Thr
        1330                1335                1340
Tyr Gly Asn Phe Met Arg Gln Ser Arg Ile Ser Glu Ile Ser Met Glu
1345                1350                1355                1360
Val Ala Glu Gln Gly Arg Gly Thr Thr Met Thr Pro Ala Asp Leu
        1365                1370                1375
Ile Glu Lys Cys Asp Cys Pro Leu Gly Tyr Ser Gly Leu Ser Cys Glu
        1380                1385                1390
Ala Cys Leu Pro Gly Phe Tyr Arg Leu Arg Ser Gln Pro Gly Gly Arg
        1395                1400                1405
Thr Pro Gly Pro Thr Leu Gly Thr Cys Val Pro Cys Gln Cys Asn Gly
        1410                1415                1420
His Ser Ser Leu Cys Asp Pro Glu Thr Ser Ile Cys Gln Asn Cys Gln
1425                1430                1435                1440
His His Thr Ala Gly Asp Phe Cys Glu Arg Cys Ala Leu Gly Tyr Tyr
        1445                1450                1455
Gly Ile Val Lys Gly Leu Pro Asn Asp Cys Gln Gln Cys Ala Cys Pro
        1460                1465                1470
Leu Ile Ser Ser Ser Asn Asn Phe Ser Pro Ser Cys Val Ala Glu Gly
        1475                1480                1485
Leu Asp Asp Tyr Arg Cys Thr Ala Cys Pro Arg Gly Tyr Glu Gly Gln
        1490                1495                1500
Tyr Cys Glu Arg Cys Ala Pro Gly Tyr Thr Gly Ser Pro Gly Asn Pro
1505                1510                1515                1520
Gly Gly Ser Cys Gln Glu Cys Glu Cys Asp Pro Tyr Gly Ser Leu Pro
        1525                1530                1535
Val Pro Cys Asp Pro Val Thr Gly Phe Cys Thr Cys Arg Pro Gly Ala
        1540                1545                1550
```

-continued

Thr Gly Arg Lys Cys Asp Gly Cys Lys His Trp His Ala Arg Glu Gly
1555                 1560                 1565

Trp Glu Cys Val Phe Cys Gly Asp Glu Cys Thr Gly Leu Leu Leu Gly
1570                 1575                 1580

Asp Leu Ala Arg Leu Glu Gln Met Val Met Ser Ile Asn Leu Thr Gly
1585                 1590                 1595                 1600

Pro Leu Pro Ala Pro Tyr Lys Met Leu Tyr Gly Leu Glu Asn Met Thr
            1605                 1610                 1615

Gln Glu Leu Lys His Leu Leu Ser Pro Gln Arg Ala Pro Glu Arg Leu
        1620                 1625                 1630

Ile Gln Leu Ala Glu Gly Asn Leu Asn Thr Leu Val Thr Glu Met Asn
1635                 1640                 1645

Glu Leu Leu Thr Arg Ala Thr Lys Val Thr Ala Asp Gly Glu Gln Thr
1650                 1655                 1660

Gly Gln Asp Ala Glu Arg Thr Asn Thr Arg Ala Lys Ser Leu Gly Glu
1665                 1670                 1675                 1680

Phe Ile Lys Glu Leu Ala Arg Asp Ala Glu Ala Val Asn Glu Lys Ala
            1685                 1690                 1695

Ile Lys Leu Asn Glu Thr Leu Gly Thr Arg Asp Glu Ala Phe Glu Arg
        1700                 1705                 1710

Asn Leu Glu Gly Leu Gln Lys Glu Ile Asp Gln Met Ile Lys Glu Leu
    1715                 1720                 1725

Arg Arg Lys Asn Leu Glu Thr Gln Lys Glu Ile Ala Glu Asp Glu Leu
1730                 1735                 1740

Val Ala Ala Glu Ala Leu Leu Lys Lys Val Lys Lys Leu Phe Gly Glu
1745                 1750                 1755                 1760

Ser Arg Gly Glu Asn Glu Glu Met Glu Lys Asp Leu Arg Glu Lys Leu
            1765                 1770                 1775

Ala Asp Tyr Lys Asn Lys Val Asp Asp Ala Trp Asp Leu Leu Arg Glu
        1780                 1785                 1790

Ala Thr Asp Lys Ile Arg Glu Ala Asn Arg Leu Phe Ala Val Asn Gln
    1795                 1800                 1805

Lys Asn Met Thr Ala Leu Glu Lys Lys Lys Glu Ala Val Glu Ser Gly
1810                 1815                 1820

Lys Arg Gln Ile Glu Asn Thr Leu Lys Glu Gly Asn Asp Ile Leu Asp
1825                 1830                 1835                 1840

Glu Ala Asn Arg Leu Ala Asp Glu Ile Asn Ser Ile Ile Asp Tyr Val
            1845                 1850                 1855

Glu Asp Ile Gln Thr Lys Leu Pro Pro Met Ser Glu Glu Leu Asn Asp
        1860                 1865                 1870

Lys Ile Asp Asp Leu Ser Gln Glu Ile Lys Asp Arg Lys Leu Ala Glu
    1875                 1880                 1885

Lys Val Ser Gln Ala Glu Ser His Ala Ala Gln Leu Asn Asp Ser Ser
1890                 1895                 1900

Ala Val Leu Asp Gly Ile Leu Asp Glu Ala Lys Asn Ile Ser Phe Asn
1905                 1910                 1915                 1920

Ala Thr Ala Ala Phe Lys Ala Tyr Ser Asn Ile Lys Asp Tyr Ile Asp
            1925                 1930                 1935

Glu Ala Glu Lys Val Ala Lys Glu Ala Lys Asp Leu Ala His Glu Ala
        1940                 1945                 1950

Thr Lys Leu Ala Thr Gly Pro Arg Gly Leu Leu Lys Glu Asp Ala Lys
    1955                 1960                 1965

```
Gly Cys Leu Gln Lys Ser Phe Arg Ile Leu Asn Glu Ala Lys Lys Leu
    1970                1975                1980

Ala Asn Asp Val Lys Glu Asn Glu Asp His Leu Asn Gly Leu Lys Thr
1985                1990                1995                2000

Arg Ile Glu Asn Ala Asp Ala Arg Asn Gly Asp Leu Leu Arg Thr Leu
            2005                2010                2015

Asn Asp Thr Leu Gly Lys Leu Ser Ala Ile Pro Asn Asp Thr Ala Ala
            2020                2025                2030

Lys Leu Gln Ala Val Lys Asp Lys Ala Arg Gln Ala Asn Asp Thr Ala
            2035                2040                2045

Lys Asp Val Leu Ala Gln Ile Thr Glu Leu His Gln Asn Leu Asp Gly
            2050                2055                2060

Leu Lys Lys Asn Tyr Asn Lys Leu Ala Asp Ser Val Ala Lys Thr Asn
2065                2070                2075                2080

Ala Val Val Lys Asp Pro Ser Lys Asn Lys Ile Ile Ala Asp Ala Asp
            2085                2090                2095

Ala Thr Val Lys Asn Leu Glu Gln Glu Ala Asp Arg Leu Ile Asp Lys
            2100                2105                2110

Leu Lys Pro Ile Lys Glu Leu Glu Asp Asn Leu Lys Lys Asn Ile Ser
    2115                2120                2125

Glu Ile Lys Glu Leu Ile Asn Gln Ala Arg Lys Gln Ala Asn Ser Ile
    2130                2135                2140

Lys Val Ser Val Ser Ser Gly Asp Cys Ile Arg Thr Tyr Lys Pro
2145                2150                2155                2160

Glu Ile Lys Lys Gly Ser Tyr Asn Asn Ile Val Val Asn Val Lys Thr
            2165                2170                2175

Ala Val Ala Asp Asn Leu Leu Phe Tyr Leu Gly Ser Ala Lys Phe Ile
            2180                2185                2190

Asp Phe Leu Ala Ile Glu Met Arg Lys Gly Lys Val Ser Phe Leu Trp
    2195                2200                2205

Asp Val Gly Ser Gly Val Gly Arg Val Glu Tyr Pro Asp Leu Thr Ile
    2210                2215                2220

Asp Asp Ser Tyr Trp Tyr Arg Ile Val Ala Ser Arg Thr Gly Arg Asn
2225                2230                2235                2240

Gly Thr Ile Ser Val Arg Ala Leu Asp Gly Pro Lys Ala Ser Ile Val
            2245                2250                2255

Pro Ser Thr His His Ser Thr Ser Pro Pro Gly Tyr Thr Ile Leu Asp
            2260                2265                2270

Val Asp Ala Asn Ala Met Leu Phe Val Gly Gly Leu Thr Gly Lys Leu
    2275                2280                2285

Lys Lys Ala Asp Ala Val Arg Val Ile Thr Phe Thr Gly Cys Met Gly
    2290                2295                2300

Glu Thr Tyr Phe Asp Asn Lys Pro Ile Gly Leu Trp Asn Phe Arg Glu
2305                2310                2315                2320

Lys Glu Gly Asp Cys Lys Gly Cys Thr Val Ser Pro Gln Val Glu Asp
            2325                2330                2335

Ser Glu Gly Thr Ala Thr Arg Asp Leu Arg Asp Phe Met Ser Val Glu
            2340                2345                2350

Leu Thr Asp Gly His Ile Lys Val Ser Tyr Asp Leu Gly Ser Gly Met
            2355                2360                2365

Ala Ser Val Val Ser Asn Gln Asn His Asn Asp Gly Lys Trp Lys Ser
            2370                2375                2380

Phe Thr Leu Ser Arg Ile Gln Lys Gln Ala Asn Ile Ser Ile Val Asp
```

-continued

```
                2385                2390                2395                2400
Ile Asp Thr Asn Gln Glu Glu Asn Ile Ala Thr Ser Ser Ser Gly Asn
                2405                2410                2415
Asn Phe Gly Leu Asp Leu Lys Ala Asp Asp Lys Ile Tyr Phe Gly Gly
            2420                2425                2430
Leu Pro Thr Leu Arg Asn Leu Ser Met Lys Ala Arg Pro Glu Val Asn
        2435                2440                2445
Leu Lys Lys Tyr Ser Gly Cys Leu Lys Asp Ile Glu Ile Ser Arg Thr
    2450                2455                2460
Pro Tyr Asn Ile Leu Ser Ser Pro Asp Tyr Val Gly Val Thr Lys Gly
2465                2470                2475                2480
Cys Ser Leu Glu Asn Val Tyr Thr Val Ser Phe Pro Lys Pro Gly Phe
            2485                2490                2495
Val Glu Leu Ser Pro Val Pro Ile Asp Val Gly Thr Glu Ile Asn Leu
        2500                2505                2510
Ser Phe Ser Thr Lys Asn Glu Ser Gly Ile Ile Leu Leu Gly Ser Gly
    2515                2520                2525
Gly Thr Pro Ala Pro Pro Arg Arg Lys Arg Arg Gln Thr Gly Gln Ala
    2530                2535                2540
Tyr Tyr Val Ile Leu Leu Asn Arg Gly Arg Leu Glu Val His Leu Ser
2545                2550                2555                2560
Thr Gly Ala Arg Thr Met Arg Lys Ile Val Ile Arg Pro Glu Pro Asn
            2565                2570                2575
Leu Phe His Asp Gly Arg Glu His Ser Val His Val Glu Arg Thr Arg
        2580                2585                2590
Gly Ile Phe Thr Val Gln Val Asp Glu Asn Arg Arg Tyr Met Gln Asn
    2595                2600                2605
Leu Thr Val Glu Gln Pro Ile Glu Val Lys Lys Leu Phe Val Gly Gly
    2610                2615                2620
Ala Pro Pro Glu Phe Gln Pro Ser Pro Leu Arg Asn Ile Pro Pro Phe
2625                2630                2635                2640
Glu Gly Cys Ile Trp Asn Leu Val Ile Asn Ser Val Pro Met Asp Phe
            2645                2650                2655
Ala Arg Pro Val Ser Phe Lys Asn Ala Asp Ile Gly Arg Cys Ala His
        2660                2665                2670
Gln Lys Leu Arg Glu Asp Glu Asp Gly Ala Ala Pro Ala Glu Ile Val
    2675                2680                2685
Ile Gln Pro Glu Pro Val Pro Thr Pro Ala Phe Pro Thr Pro Thr Pro
    2690                2695                2700
Val Leu Thr His Gly Pro Cys Ala Ala Glu Ser Glu Pro Ala Leu Leu
2705                2710                2715                2720
Ile Gly Ser Lys Gln Phe Gly Leu Ser Arg Asn Ser His Ile Ala Ile
            2725                2730                2735
Ala Phe Asp Asp Thr Lys Val Lys Asn Arg Leu Thr Ile Glu Leu Glu
        2740                2745                2750
Val Arg Thr Glu Ala Glu Ser Gly Leu Leu Phe Tyr Met Ala Ala Ile
    2755                2760                2765
Asn His Ala Asp Phe Ala Thr Val Gln Leu Arg Asn Gly Leu Pro Tyr
    2770                2775                2780
Phe Ser Tyr Asp Leu Gly Ser Gly Asp Thr His Thr Met Ile Pro Thr
2785                2790                2795                2800
Lys Ile Asn Asp Gly Gln Trp His Lys Ile Lys Ile Met Arg Ser Lys
            2805                2810                2815
```

```
Gln Glu Gly Ile Leu Tyr Val Asp Gly Ala Ser Asn Arg Thr Ile Ser
        2820                2825                2830

Pro Lys Lys Ala Asp Ile Leu Asp Val Val Gly Met Leu Tyr Val Gly
        2835                2840            2845

Gly Leu Pro Ile Asn Tyr Thr Thr Arg Arg Ile Gly Pro Val Thr Tyr
        2850                2855                2860

Ser Ile Asp Gly Cys Val Arg Asn Leu His Met Ala Glu Ala Pro Ala
2865                2870                2875                2880

Asp Leu Glu Gln Pro Thr Ser Ser Phe His Val Gly Thr Cys Phe Ala
            2885                2890                2895

Asn Ala Gln Arg Gly Thr Tyr Phe Asp Gly Thr Gly Phe Ala Lys Ala
        2900                2905                2910

Val Gly Gly Phe Lys Val Gly Leu Asp Leu Val Glu Phe Glu Phe
        2915                2920                2925

Ala Thr Thr Thr Thr Thr Gly Val Leu Leu Gly Ile Ser Ser Gln Lys
        2930                2935                2940

Met Asp Gly Met Gly Ile Glu Met Ile Asp Glu Lys Leu Met Phe His
2945                2950                2955                2960

Val Asp Asn Gly Ala Gly Arg Phe Thr Ala Val Tyr Asp Ala Gly Val
            2965                2970                2975

Pro Gly His Leu Cys Asp Gly Gln Trp His Lys Val Thr Ala Asn Lys
            2980                2985                2990

Ile Lys His Arg Ile Glu Leu Thr Val Asp Gly Asn Gln Val Glu Ala
        2995                3000                3005

Gln Ser Pro Asn Pro Ala Ser Thr Ser Ala Asp Thr Asn Asp Pro Val
        3010                3015                3020

Phe Val Gly Gly Phe Pro Asp Asp Leu Lys Gln Phe Gly Leu Thr Thr
3025                3030                3035                3040

Ser Ile Pro Phe Arg Gly Cys Ile Arg Ser Leu Lys Leu Thr Lys Gly
            3045                3050                3055

Thr Ala Ser His Trp Arg Leu Ile Leu Pro Arg Pro Trp Asn
            3060                3065                3070

<210> SEQ ID NO 8
<211> LENGTH: 730
<212> TYPE: PRT
<213> ORGANISM: Homo sapiens

<400> SEQUENCE: 8

Met Ala Gly Leu Thr Ala Ala Pro Arg Pro Gly Val Leu Leu Leu
  1               5                   10                  15

Leu Leu Ser Ile Leu His Pro Ser Arg Pro Gly Gly Val Pro Gly Ala
            20                  25                  30

Ile Pro Gly Gly Val Pro Gly Gly Val Phe Tyr Pro Gly Ala Gly Leu
        35                  40                  45

Gly Ala Leu Gly Gly Gly Ala Leu Gly Pro Gly Gly Lys Pro Leu Lys
    50                  55                  60

Pro Val Pro Gly Gly Leu Ala Gly Ala Gly Leu Gly Ala Gly Leu Gly
65                  70                  75                  80

Ala Phe Pro Ala Val Thr Phe Pro Gly Ala Leu Val Pro Gly Gly Val
                85                  90                  95

Ala Asp Ala Ala Ala Ala Tyr Lys Ala Ala Lys Ala Gly Ala Gly Leu
            100                 105                 110

Gly Gly Val Pro Gly Val Gly Gly Leu Gly Val Ser Ala Gly Ala Val
```

```
                115                 120                 125
Val Pro Gln Pro Gly Ala Gly Val Lys Pro Gly Lys Val Pro Gly Val
            130                 135                 140

Gly Leu Pro Gly Val Tyr Pro Gly Gly Val Leu Pro Gly Ala Arg Phe
145                 150                 155                 160

Pro Gly Val Gly Val Leu Pro Gly Val Pro Thr Gly Ala Gly Val Lys
                165                 170                 175

Pro Lys Ala Pro Gly Val Gly Ala Phe Ala Gly Ile Pro Gly Val
            180                 185                 190

Gly Pro Phe Gly Pro Gln Pro Gly Val Pro Leu Gly Tyr Pro Ile
            195                 200                 205

Lys Ala Pro Lys Leu Pro Gly Gly Tyr Gly Leu Pro Tyr Thr Thr Gly
            210                 215                 220

Lys Leu Pro Tyr Gly Tyr Gly Pro Gly Gly Val Ala Gly Ala Ala Gly
225                 230                 235                 240

Lys Ala Gly Tyr Pro Thr Gly Thr Gly Val Gly Pro Gln Ala Ala Ala
                245                 250                 255

Ala Ala Ala Ala Lys Ala Ala Lys Phe Gly Ala Gly Ala Ala Gly
            260                 265                 270

Val Leu Pro Gly Val Gly Gly Ala Gly Val Pro Gly Val Pro Gly Ala
            275                 280                 285

Ile Pro Gly Ile Gly Gly Ile Ala Gly Val Gly Thr Pro Ala Ala Ala
            290                 295                 300

Ala Ala Ala Ala Ala Ala Ala Lys Ala Ala Lys Tyr Gly Ala Ala Ala
305                 310                 315                 320

Gly Leu Val Pro Gly Gly Pro Gly Phe Gly Pro Gly Val Val Gly Val
                325                 330                 335

Pro Gly Ala Gly Val Pro Gly Val Gly Val Pro Gly Ala Gly Ile Pro
            340                 345                 350

Val Val Pro Gly Ala Gly Ile Pro Gly Ala Ala Val Pro Gly Val Val
            355                 360                 365

Ser Pro Glu Ala Ala Ala Lys Ala Ala Ala Lys Ala Ala Lys Tyr Gly
            370                 375                 380

Ala Arg Pro Gly Val Gly Val Gly Gly Ile Pro Thr Tyr Gly Val Gly
385                 390                 395                 400

Ala Gly Gly Phe Pro Gly Phe Gly Val Gly Val Gly Gly Ile Pro Gly
                405                 410                 415

Val Ala Gly Val Pro Ser Val Gly Gly Val Pro Gly Val Gly Gly Val
            420                 425                 430

Pro Gly Val Gly Ile Ser Pro Glu Ala Gln Ala Ala Ala Ala Lys
            435                 440                 445

Ala Ala Lys Tyr Gly Val Gly Thr Pro Ala Ala Ala Ala Lys Ala
            450                 455                 460

Ala Ala Lys Ala Ala Gln Phe Ala Leu Leu Asn Leu Ala Gly Leu Val
465                 470                 475                 480

Pro Gly Val Gly Val Ala Pro Gly Val Gly Val Ala Pro Gly Val Gly
                485                 490                 495

Val Ala Pro Gly Val Gly Leu Ala Pro Gly Val Gly Val Ala Pro Gly
            500                 505                 510

Val Gly Val Ala Pro Gly Val Gly Val Ala Pro Gly Ile Gly Pro Gly
            515                 520                 525

Gly Val Ala Ala Ala Ala Lys Ser Ala Ala Lys Val Ala Ala Lys Ala
530                 535                 540
```

-continued

```
Gln Leu Arg Ala Ala Gly Leu Gly Ala Gly Ile Pro Gly Leu Gly
545                 550                 555                 560

Val Gly Val Gly Val Pro Gly Leu Gly Val Gly Ala Gly Val Pro Gly
                565                 570                 575

Leu Gly Val Gly Ala Gly Val Pro Gly Phe Gly Ala Val Pro Gly Ala
                580                 585                 590

Leu Ala Ala Ala Lys Ala Ala Lys Tyr Gly Ala Ala Val Pro Gly Val
                595                 600                 605

Leu Gly Gly Leu Gly Ala Leu Gly Gly Val Gly Ile Pro Gly Gly Val
                610                 615                 620

Val Gly Ala Gly Pro Ala Ala Ala Ala Ala Ala Lys Ala Ala
625                 630                 635                 640

Lys Ala Ala Gln Phe Gly Leu Val Gly Ala Ala Gly Leu Gly Gly Leu
                645                 650                 655

Gly Val Gly Gly Leu Gly Val Pro Gly Val Gly Leu Gly Gly Ile
                660                 665                 670

Pro Pro Ala Ala Ala Ala Lys Ala Ala Lys Tyr Gly Ala Ala Gly Leu
                675                 680                 685

Gly Gly Val Leu Gly Gly Ala Gly Gln Phe Pro Leu Gly Gly Val Ala
                690                 695                 700

Ala Arg Pro Gly Phe Gly Leu Ser Pro Ile Phe Pro Gly Gly Ala Cys
705                 710                 715                 720

Leu Gly Lys Ala Cys Gly Arg Lys Arg Lys
                725                 730

<210> SEQ ID NO 9
<211> LENGTH: 1712
<212> TYPE: PRT
<213> ORGANISM: Homo sapiens

<400> SEQUENCE: 9

Met Gly Arg Asp Gln Arg Ala Val Ala Gly Pro Ala Leu Arg Arg Trp
1               5                   10                  15

Leu Leu Leu Gly Thr Val Thr Val Gly Phe Leu Ala Gln Ser Val Leu
                20                  25                  30

Ala Gly Val Lys Lys Phe Asp Val Pro Cys Gly Gly Arg Asp Cys Ser
                35                  40                  45

Gly Gly Cys Gln Cys Tyr Pro Glu Lys Gly Gly Arg Gly Gln Pro Gly
                50                  55                  60

Pro Val Gly Pro Gln Gly Tyr Asn Gly Pro Pro Gly Leu Gln Gly Phe
65                  70                  75                  80

Pro Gly Leu Gln Gly Arg Lys Gly Asp Lys Gly Glu Arg Gly Ala Pro
                85                  90                  95

Gly Val Thr Gly Pro Lys Gly Asp Val Gly Ala Arg Gly Val Ser Gly
                100                 105                 110

Phe Pro Gly Ala Asp Gly Ile Pro Gly His Pro Gly Gln Gly Gly Pro
                115                 120                 125

Arg Gly Arg Pro Gly Tyr Asp Gly Cys Asn Gly Thr Gln Gly Asp Ser
                130                 135                 140

Gly Pro Gln Gly Pro Pro Gly Ser Glu Gly Phe Thr Gly Pro Pro Gly
145                 150                 155                 160

Pro Gln Gly Pro Lys Gly Gln Lys Gly Glu Pro Tyr Ala Leu Pro Lys
                165                 170                 175

Glu Glu Arg Asp Arg Tyr Arg Gly Glu Pro Gly Glu Pro Gly Leu Val
```

```
                    180                 185                 190
Gly Phe Gln Gly Pro Pro Gly Arg Pro Gly His Val Gly Gln Met Gly
                195                 200                 205
Pro Val Gly Ala Pro Gly Arg Pro Gly Pro Pro Gly Pro Gly Pro
210                 215                 220
Lys Gly Gln Gln Gly Asn Arg Gly Leu Gly Phe Tyr Gly Val Lys Gly
225                 230                 235                 240
Glu Lys Gly Asp Val Gly Gln Pro Gly Pro Asn Gly Ile Pro Ser Asp
                245                 250                 255
Thr Leu His Pro Ile Ile Ala Pro Thr Gly Val Thr Phe His Pro Asp
                260                 265                 270
Gln Tyr Lys Gly Glu Lys Gly Ser Glu Gly Glu Pro Gly Ile Arg Gly
                275                 280                 285
Ile Ser Leu Lys Gly Glu Glu Gly Ile Met Gly Phe Pro Gly Leu Arg
                290                 295                 300
Gly Tyr Pro Gly Leu Ser Gly Glu Lys Gly Ser Pro Gly Gln Lys Gly
305                 310                 315                 320
Ser Arg Gly Leu Asp Gly Tyr Gln Gly Pro Asp Gly Pro Arg Gly Pro
                325                 330                 335
Lys Gly Glu Ala Gly Asp Pro Gly Pro Pro Gly Leu Pro Ala Tyr Ser
                340                 345                 350
Pro His Pro Ser Leu Ala Lys Gly Ala Arg Gly Asp Pro Gly Phe Pro
                355                 360                 365
Gly Ala Gln Gly Glu Pro Gly Ser Gln Gly Glu Pro Gly Asp Pro Gly
                370                 375                 380
Leu Pro Gly Pro Pro Gly Leu Ser Ile Gly Asp Gly Asp Gln Arg Arg
385                 390                 395                 400
Gly Leu Pro Gly Glu Met Gly Pro Lys Gly Phe Ile Gly Asp Pro Gly
                405                 410                 415
Ile Pro Ala Leu Tyr Gly Gly Pro Pro Gly Pro Asp Gly Lys Arg Gly
                420                 425                 430
Pro Pro Gly Pro Pro Gly Leu Pro Gly Pro Pro Gly Pro Asp Gly Phe
                435                 440                 445
Leu Phe Gly Leu Lys Gly Ala Lys Gly Arg Ala Gly Phe Pro Gly Leu
450                 455                 460
Pro Gly Ser Pro Gly Ala Arg Gly Pro Lys Gly Trp Lys Gly Asp Ala
465                 470                 475                 480
Gly Glu Cys Arg Cys Thr Glu Gly Asp Glu Ala Ile Lys Gly Leu Pro
                485                 490                 495
Gly Leu Pro Gly Pro Lys Gly Phe Ala Gly Ile Asn Gly Glu Pro Gly
                500                 505                 510
Arg Lys Gly Asp Lys Gly Asp Pro Gly Gln His Gly Leu Pro Gly Phe
                515                 520                 525
Pro Gly Leu Lys Gly Val Pro Gly Asn Ile Gly Ala Pro Gly Pro Lys
                530                 535                 540
Gly Ala Lys Gly Asp Ser Arg Thr Ile Thr Thr Lys Gly Glu Arg Gly
545                 550                 555                 560
Gln Pro Gly Val Pro Gly Val Pro Gly Met Lys Gly Asp Asp Gly Ser
                565                 570                 575
Pro Gly Arg Asp Gly Leu Asp Gly Phe Pro Gly Leu Pro Gly Pro Pro
                580                 585                 590
Gly Asp Gly Ile Lys Gly Pro Pro Gly Asp Pro Gly Tyr Pro Gly Ile
                595                 600                 605
```

```
Pro Gly Thr Lys Gly Thr Pro Gly Glu Met Gly Pro Pro Gly Leu Gly
    610                 615                 620

Leu Pro Gly Leu Lys Gly Gln Arg Gly Phe Pro Gly Asp Ala Gly Leu
625                 630                 635                 640

Pro Gly Pro Pro Gly Phe Leu Gly Pro Pro Gly Pro Ala Gly Thr Pro
                    645                 650                 655

Gly Gln Ile Asp Cys Asp Thr Asp Val Lys Arg Ala Val Gly Gly Asp
            660                 665                 670

Arg Gln Glu Ala Ile Gln Pro Gly Cys Ile Ala Gly Pro Lys Gly Leu
        675                 680                 685

Pro Gly Leu Pro Gly Pro Pro Gly Pro Thr Gly Ala Lys Gly Leu Arg
    690                 695                 700

Gly Ile Pro Gly Phe Ala Gly Ala Asp Gly Pro Gly Pro Arg Gly
705                 710                 715                 720

Leu Pro Gly Asp Ala Gly Arg Glu Gly Phe Pro Gly Pro Pro Gly Phe
                725                 730                 735

Ile Gly Pro Arg Gly Ser Lys Gly Ala Val Gly Leu Pro Gly Pro Asp
                740                 745                 750

Gly Ser Pro Gly Pro Ile Gly Leu Pro Gly Pro Asp Gly Pro Pro Gly
        755                 760                 765

Glu Arg Gly Leu Pro Gly Glu Val Leu Gly Ala Gln Pro Gly Pro Arg
    770                 775                 780

Gly Asp Ala Gly Val Pro Gly Gln Pro Gly Leu Lys Gly Leu Pro Gly
785                 790                 795                 800

Asp Arg Gly Pro Pro Gly Phe Arg Gly Ser Gln Gly Met Pro Gly Met
                805                 810                 815

Pro Gly Leu Lys Gly Gln Pro Gly Leu Pro Gly Pro Ser Gly Gln Pro
                820                 825                 830

Gly Leu Tyr Gly Pro Pro Gly Leu His Gly Phe Pro Gly Ala Pro Gly
        835                 840                 845

Gln Glu Gly Pro Leu Gly Leu Pro Gly Ile Pro Gly Arg Glu Gly Leu
    850                 855                 860

Pro Gly Asp Arg Gly Asp Pro Gly Asp Thr Gly Ala Pro Gly Pro Val
865                 870                 875                 880

Gly Met Lys Gly Leu Ser Gly Asp Arg Gly Asp Ala Gly Phe Thr Gly
                885                 890                 895

Glu Gln Gly His Pro Gly Ser Pro Gly Phe Lys Gly Ile Asp Gly Met
                900                 905                 910

Pro Gly Thr Pro Gly Leu Lys Gly Asp Arg Gly Ser Pro Gly Met Asp
        915                 920                 925

Gly Phe Gln Gly Met Pro Gly Leu Lys Gly Arg Pro Gly Phe Pro Gly
    930                 935                 940

Ser Lys Gly Glu Ala Gly Phe Phe Gly Ile Pro Gly Leu Lys Gly Leu
945                 950                 955                 960

Ala Gly Glu Pro Gly Phe Lys Gly Ser Arg Gly Asp Pro Gly Pro Pro
                965                 970                 975

Gly Pro Pro Pro Val Ile Leu Pro Gly Met Lys Asp Ile Lys Gly Glu
            980                 985                 990

Lys Gly Asp Glu Gly Pro Met Gly Leu Lys Gly Tyr Leu Gly Ala Lys
        995                 1000                1005

Gly Ile Gln Gly Met Pro Gly Ile Pro Gly Leu Ser Gly Ile Pro Gly
   1010                 1015                 1020
```

-continued

```
Leu Pro Gly Arg Pro Gly His Ile Lys Gly Val Lys Gly Asp Ile Gly
1025                1030                1035                1040

Val Pro Gly Ile Pro Gly Leu Pro Gly Phe Pro Gly Val Ala Gly Pro
                1045                1050                1055

Pro Gly Ile Thr Gly Phe Pro Gly Phe Ile Gly Ser Arg Gly Asp Lys
            1060                1065                1070

Gly Ala Pro Gly Arg Ala Gly Leu Tyr Gly Glu Ile Gly Ala Thr Gly
        1075                1080                1085

Asp Phe Gly Asp Ile Gly Asp Thr Ile Asn Leu Pro Gly Arg Pro Gly
    1090                1095                1100

Leu Lys Gly Glu Arg Gly Thr Thr Gly Ile Pro Gly Leu Lys Gly Phe
1105                1110                1115                1120

Phe Gly Glu Lys Gly Thr Glu Gly Asp Ile Gly Phe Pro Gly Ile Thr
                1125                1130                1135

Gly Val Thr Gly Val Gln Gly Pro Pro Gly Leu Lys Gly Gln Thr Gly
            1140                1145                1150

Phe Pro Gly Leu Thr Gly Pro Pro Gly Ser Gln Gly Glu Leu Gly Arg
        1155                1160                1165

Ile Gly Leu Pro Gly Gly Lys Gly Asp Asp Gly Trp Pro Gly Ala Pro
    1170                1175                1180

Gly Leu Pro Gly Phe Pro Gly Leu Arg Gly Ile Arg Gly Leu His Gly
1185                1190                1195                1200

Leu Pro Gly Thr Lys Gly Phe Pro Gly Ser Pro Gly Ser Asp Ile His
                1205                1210                1215

Gly Asp Pro Gly Phe Pro Gly Pro Pro Gly Glu Arg Gly Asp Pro Gly
            1220                1225                1230

Glu Ala Asn Thr Leu Pro Gly Pro Val Gly Val Pro Gly Gln Lys Gly
        1235                1240                1245

Asp Gln Gly Ala Pro Gly Glu Arg Gly Pro Pro Gly Ser Pro Gly Leu
    1250                1255                1260

Gln Gly Phe Pro Gly Ile Thr Pro Pro Ser Asn Ile Ser Gly Ala Pro
1265                1270                1275                1280

Gly Asp Lys Gly Ala Pro Gly Ile Phe Gly Leu Lys Gly Tyr Arg Gly
                1285                1290                1295

Pro Pro Gly Pro Pro Gly Ser Ala Ala Leu Pro Gly Ser Lys Gly Asp
            1300                1305                1310

Thr Gly Asn Pro Gly Ala Pro Gly Thr Pro Gly Thr Lys Gly Trp Ala
        1315                1320                1325

Gly Asp Ser Gly Pro Gln Gly Arg Pro Gly Val Phe Gly Leu Pro Gly
    1330                1335                1340

Glu Lys Gly Pro Arg Gly Glu Gln Gly Phe Met Gly Asn Thr Gly Pro
1345                1350                1355                1360

Thr Gly Ala Val Gly Asp Arg Gly Pro Lys Gly Pro Lys Gly Asp Pro
                1365                1370                1375

Gly Phe Pro Gly Ala Pro Gly Thr Val Gly Ala Pro Gly Ile Ala Gly
            1380                1385                1390

Ile Pro Gln Lys Ile Ala Ile Gln Pro Gly Thr Val Gly Pro Gln Gly
        1395                1400                1405

Arg Arg Gly Pro Pro Gly Ala Pro Gly Glu Ile Gly Pro Gln Gly Pro
    1410                1415                1420

Pro Gly Glu Pro Gly Phe Arg Gly Ala Pro Gly Lys Ala Gly Pro Gln
1425                1430                1435                1440

Gly Arg Gly Gly Val Ser Ala Val Pro Gly Phe Arg Gly Asp Glu Gly
```

-continued

```
                 1445                1450                1455
Pro Ile Gly His Gln Gly Pro Ile Gly Gln Glu Gly Ala Pro Gly Arg
            1460                1465                1470
Pro Gly Ser Pro Gly Leu Pro Gly Met Pro Gly Arg Ser Val Ser Ile
        1475                1480                1485
Gly Tyr Leu Leu Val Lys His Ser Gln Thr Asp Gln Glu Pro Met Cys
        1490                1495                1500
Pro Val Gly Met Asn Lys Leu Trp Ser Gly Tyr Ser Leu Leu Tyr Phe
1505                1510                1515                1520
Glu Gly Gln Glu Lys Ala His Asn Gln Asp Leu Gly Leu Ala Gly Ser
            1525                1530                1535
Cys Leu Ala Arg Phe Ser Thr Met Pro Phe Leu Tyr Cys Asn Pro Gly
            1540                1545                1550
Asp Val Cys Tyr Tyr Ala Ser Arg Asn Asp Lys Ser Tyr Trp Leu Ser
        1555                1560                1565
Thr Thr Ala Pro Leu Pro Met Met Pro Val Ala Glu Asp Glu Ile Lys
    1570                1575                1580
Pro Tyr Ile Ser Arg Cys Ser Val Cys Glu Ala Pro Ala Ile Ala Ile
1585                1590                1595                1600
Ala Val His Ser Gln Asp Val Ser Ile Pro His Cys Pro Ala Gly Trp
            1605                1610                1615
Arg Ser Leu Trp Ile Gly Tyr Ser Phe Leu Met His Thr Ala Ala Gly
            1620                1625                1630
Asp Glu Gly Gly Gly Gln Ser Leu Val Ser Pro Gly Ser Cys Leu Glu
            1635                1640                1645
Asp Phe Arg Ala Thr Pro Phe Ile Glu Cys Asn Gly Gly Arg Gly Thr
        1650                1655                1660
Cys His Tyr Tyr Ala Asn Lys Tyr Ser Phe Trp Leu Thr Thr Ile Pro
1665                1670                1675                1680
Glu Gln Ser Phe Gln Gly Ser Pro Ser Ala Asp Thr Leu Lys Ala Gly
            1685                1690                1695
Leu Ile Arg Thr His Ile Ser Arg Cys Gln Val Cys Met Lys Asn Leu
        1700                1705                1710

<210> SEQ ID NO 10
<211> LENGTH: 122
<212> TYPE: PRT
<213> ORGANISM: Homo sapiens

<400> SEQUENCE: 10

Met Glu Ala Ser Ala Leu Thr Ser Ser Ala Val Thr Ser Val Ala Lys
1               5                   10                  15
Val Val Arg Val Ala Ser Gly Ser Ala Val Val Leu Pro Leu Ala Arg
            20                  25                  30
Ile Ala Thr Val Val Ile Gly Gly Val Ala Met Ala Ala Val Pro
        35                  40                  45
Met Val Leu Ser Ala Met Gly Phe Thr Ala Ala Gly Ile Ala Ser Ser
    50                  55                  60
Ser Ile Ala Ala Lys Met Met Ser Ala Ala Ile Ala Asn Gly Gly
65                  70                  75                  80
Gly Val Ala Ser Gly Ser Leu Val Gly Thr Leu Gln Ser Leu Gly Ala
            85                  90                  95
Thr Gly Leu Ser Gly Leu Thr Lys Phe Ile Leu Gly Ser Ile Gly Ser
            100                 105                 110
```

-continued

```
Ala Ile Ala Ala Val Ile Ala Arg Phe Tyr
        115                 120

<210> SEQ ID NO 11
<211> LENGTH: 331
<212> TYPE: PRT
<213> ORGANISM: Homo sapiens

<400> SEQUENCE: 11

Met Ala Arg Gly Gly Arg Gly Arg Arg Leu Gly Leu Ala Leu Gly Leu
 1               5                  10                  15

Leu Leu Ala Leu Val Leu Ala Pro Arg Val Leu Arg Ala Lys Pro Thr
            20                  25                  30

Val Arg Lys Glu Arg Val Val Arg Pro Asp Ser Glu Leu Gly Glu Arg
        35                  40                  45

Pro Pro Glu Asp Asn Gln Ser Phe Gln Tyr Asp His Glu Ala Phe Leu
    50                  55                  60

Gly Lys Glu Asp Ser Lys Thr Phe Asp Gln Leu Thr Pro Asp Glu Ser
65                  70                  75                  80

Lys Glu Arg Leu Gly Lys Ile Val Asp Arg Ile Asp Asn Asp Gly Asp
                85                  90                  95

Gly Phe Val Thr Thr Glu Glu Leu Lys Thr Trp Ile Lys Arg Val Gln
            100                 105                 110

Lys Arg Tyr Ile Phe Asp Asn Val Ala Lys Val Trp Lys Asp Tyr Asp
        115                 120                 125

Arg Asp Lys Asp Asp Lys Ile Ser Trp Glu Glu Tyr Lys Gln Ala Thr
    130                 135                 140

Tyr Gly Tyr Tyr Leu Gly Asn Pro Ala Glu Phe His Asp Ser Ser Asp
145                 150                 155                 160

His His Thr Phe Lys Lys Met Leu Pro Arg Asp Glu Arg Arg Phe Lys
                165                 170                 175

Ala Ala Asp Leu Asn Gly Asp Leu Thr Ala Thr Arg Glu Glu Phe Thr
            180                 185                 190

Ala Phe Leu His Pro Glu Glu Phe Glu His Met Lys Glu Ile Val Val
        195                 200                 205

Leu Glu Thr Leu Glu Asp Ile Asp Lys Asn Gly Asp Gly Phe Val Asp
    210                 215                 220

Gln Asp Glu Tyr Ile Ala Asp Met Phe Ser His Glu Glu Asn Gly Pro
225                 230                 235                 240

Glu Pro Asp Trp Val Leu Ser Glu Arg Glu Gln Phe Asn Glu Phe Arg
                245                 250                 255

Asp Leu Asn Lys Asp Gly Lys Leu Asp Lys Asp Glu Ile Arg His Trp
            260                 265                 270

Ile Leu Pro Gln Asp Tyr Asp His Ala Gln Ala Glu Ala Arg His Leu
        275                 280                 285

Val Tyr Glu Ser Asp Lys Asn Lys Asp Glu Lys Leu Thr Lys Glu Glu
    290                 295                 300

Ile Leu Glu Asn Trp Asn Met Phe Val Gly Ser Gln Ala Thr Asn Tyr
305                 310                 315                 320

Gly Glu Asp Leu Thr Lys Asn His Asp Glu Leu
                325                 330

<210> SEQ ID NO 12
<211> LENGTH: 512
<212> TYPE: PRT
<213> ORGANISM: Homo sapiens
```

```
<400> SEQUENCE: 12

Met Ala Thr Ala Asn Gly Ala Val Glu Asn Gly Gln Pro Asp Gly Lys
 1               5                  10                  15

Pro Pro Ala Leu Pro Arg Pro Ile Arg Asn Leu Glu Val Lys Phe Thr
            20                  25                  30

Lys Ile Phe Ile Asn Asn Glu Trp His Glu Ser Lys Ser Gly Lys Lys
        35                  40                  45

Phe Ala Thr Cys Asn Pro Ser Thr Arg Glu Gln Ile Cys Glu Val Glu
    50                  55                  60

Glu Gly Asp Lys Pro Asp Val Asp Lys Ala Val Glu Ala Ala Gln Val
 65                  70                  75                  80

Ala Phe Gln Arg Gly Ser Pro Trp Arg Arg Leu Asp Ala Leu Ser Arg
                85                  90                  95

Gly Arg Leu Leu His Gln Leu Ala Asp Leu Val Glu Arg Asp Arg Ala
            100                 105                 110

Thr Leu Ala Ala Leu Glu Thr Met Asp Thr Gly Lys Pro Phe Leu His
        115                 120                 125

Ala Phe Phe Ile Asp Leu Glu Gly Cys Ile Arg Thr Leu Arg Tyr Phe
    130                 135                 140

Ala Gly Trp Ala Asp Lys Ile Gln Gly Lys Thr Ile Pro Thr Asp Asp
145                 150                 155                 160

Asn Val Val Cys Phe Thr Arg His Glu Pro Ile Gly Val Cys Gly Ala
                165                 170                 175

Ile Thr Pro Trp Asn Phe Pro Leu Leu Met Leu Val Trp Lys Leu Ala
            180                 185                 190

Pro Ala Leu Cys Cys Gly Asn Thr Met Val Leu Lys Pro Ala Glu Gln
        195                 200                 205

Thr Pro Leu Thr Ala Leu Tyr Leu Gly Ser Leu Ile Lys Glu Ala Gly
    210                 215                 220

Phe Pro Pro Gly Val Val Asn Ile Val Pro Gly Phe Gly Pro Thr Val
225                 230                 235                 240

Gly Ala Ala Ile Ser Ser His Pro Gln Ile Asn Lys Ile Ala Phe Thr
                245                 250                 255

Gly Ser Thr Glu Val Gly Lys Leu Val Lys Glu Ala Ala Ser Arg Ser
            260                 265                 270

Asn Leu Lys Arg Val Thr Leu Glu Leu Gly Gly Lys Asn Pro Cys Ile
        275                 280                 285

Val Cys Ala Asp Ala Asp Leu Asp Leu Ala Val Glu Cys Ala His Gln
    290                 295                 300

Gly Val Phe Phe Asn Gln Gly Gln Cys Cys Thr Ala Ala Ser Arg Val
305                 310                 315                 320

Phe Val Glu Glu Gln Val Tyr Ser Glu Phe Val Arg Arg Ser Val Glu
                325                 330                 335

Tyr Ala Lys Lys Arg Pro Val Gly Asp Pro Phe Asp Val Lys Thr Glu
            340                 345                 350

Gln Gly Pro Gln Ile Asp Gln Lys Gln Phe Asp Lys Ile Leu Glu Leu
        355                 360                 365

Ile Glu Ser Gly Lys Lys Glu Gly Ala Lys Leu Glu Cys Gly Gly Ser
    370                 375                 380

Ala Met Glu Asp Lys Gly Leu Phe Ile Lys Pro Thr Val Phe Ser Glu
385                 390                 395                 400

Val Thr Asp Asn Met Arg Ile Ala Lys Glu Glu Ile Phe Gly Pro Val
```

```
                    405                 410                 415
Gln Pro Ile Leu Lys Phe Lys Ser Ile Glu Glu Val Ile Lys Arg Ala
                420                 425                 430
Asn Ser Thr Asp Tyr Gly Leu Thr Ala Ala Val Phe Thr Lys Asn Leu
            435                 440                 445
Asp Lys Ala Leu Lys Leu Ala Ser Ala Leu Glu Ser Gly Thr Val Trp
        450                 455                 460
Ile Asn Cys Tyr Asn Ala Leu Tyr Ala Gln Ala Pro Phe Gly Gly Phe
465                 470                 475                 480
Lys Met Ser Gly Asn Gly Arg Glu Leu Gly Glu Tyr Ala Leu Ala Glu
                485                 490                 495
Tyr Thr Glu Val Lys Thr Val Thr Ile Lys Leu Gly Asp Lys Asn Pro
                500                 505                 510

<210> SEQ ID NO 13
<211> LENGTH: 1781
<212> TYPE: PRT
<213> ORGANISM: Homo sapiens

<400> SEQUENCE: 13

Met Gly Ala Gly Ser Ser Thr Glu Gln Arg Ser Pro Glu Gln Pro Pro
1               5                   10                  15
Glu Gly Ser Ser Thr Pro Ala Glu Pro Glu Pro Ser Gly Gly Gly Pro
                20                  25                  30
Ser Ala Glu Ala Ala Pro Asp Thr Thr Ala Asp Pro Ala Ile Ala Ala
            35                  40                  45
Ser Asp Pro Ala Thr Lys Leu Leu Gln Lys Asn Gly Gln Leu Ser Thr
        50                  55                  60
Ile Asn Gly Val Ala Glu Gln Asp Glu Leu Ser Leu Gln Glu Gly Asp
65                  70                  75                  80
Leu Asn Gly Gln Lys Gly Ala Leu Asn Gly Gln Gly Ala Leu Asn Ser
                85                  90                  95
Gln Glu Glu Glu Glu Val Ile Val Thr Glu Val Gly Gln Arg Asp Ser
                100                 105                 110
Glu Asp Val Ser Glu Arg Asp Ser Asp Lys Glu Met Ala Thr Lys Ser
            115                 120                 125
Ala Val Val His Asp Ile Thr Asp Asp Gly Gln Glu Glu Asn Arg Asn
        130                 135                 140
Ile Glu Gln Ile Pro Ser Ser Glu Ser Asn Leu Glu Glu Leu Thr Gln
145                 150                 155                 160
Pro Thr Glu Ser Gln Ala Asn Asp Ile Gly Phe Lys Lys Val Phe Lys
                165                 170                 175
Phe Val Gly Phe Lys Phe Thr Val Lys Lys Asp Lys Thr Glu Lys Pro
                180                 185                 190
Asp Thr Val Gln Leu Leu Thr Val Lys Lys Asp Glu Gly Glu Gly Ala
            195                 200                 205
Ala Gly Ala Gly Asp His Gln Asp Pro Ser Leu Gly Ala Gly Glu Ala
        210                 215                 220
Ala Ser Lys Glu Ser Glu Pro Lys Gln Ser Thr Glu Lys Pro Glu Glu
225                 230                 235                 240
Thr Leu Lys Arg Glu Gln Ser His Ala Glu Ile Ser Pro Pro Ala Glu
                245                 250                 255
Ser Gly Gln Ala Val Glu Glu Cys Lys Glu Glu Gly Glu Glu Lys Gln
                260                 265                 270
```

-continued

```
Glu Lys Glu Pro Ser Lys Ser Ala Glu Ser Pro Thr Ser Pro Val Thr
        275                 280                 285

Ser Glu Thr Gly Ser Thr Phe Lys Lys Phe Phe Thr Gln Gly Trp Ala
        290                 295                 300

Gly Trp Arg Lys Lys Thr Ser Phe Arg Lys Pro Lys Glu Asp Glu Val
305                 310                 315                 320

Glu Ala Ser Glu Lys Lys Lys Glu Gln Glu Pro Glu Lys Val Asp Thr
                325                 330                 335

Glu Glu Asp Gly Lys Ala Glu Val Ala Ser Glu Lys Leu Thr Ala Ser
                340                 345                 350

Glu Gln Ala His Pro Gln Glu Pro Ala Glu Ser Ala His Glu Pro Arg
                355                 360                 365

Leu Ser Ala Glu Tyr Glu Lys Val Glu Leu Pro Ser Glu Glu Gln Val
        370                 375                 380

Ser Gly Ser Gln Gly Pro Ser Glu Glu Lys Pro Ala Pro Leu Ala Thr
385                 390                 395                 400

Glu Val Phe Asp Glu Lys Ile Glu Val His Gln Glu Val Val Ala
                405                 410                 415

Glu Val His Val Ser Thr Val Glu Glu Arg Thr Glu Glu Gln Lys Thr
                420                 425                 430

Glu Val Glu Glu Thr Ala Gly Ser Val Pro Ala Glu Glu Leu Val Gly
                435                 440                 445

Met Asp Ala Glu Pro Gln Glu Ala Glu Pro Ala Lys Glu Leu Val Lys
        450                 455                 460

Leu Lys Glu Thr Cys Val Ser Gly Glu Asp Pro Thr Gln Gly Ala Asp
465                 470                 475                 480

Leu Ser Pro Asp Glu Lys Val Leu Ser Lys Pro Pro Glu Gly Val Val
                485                 490                 495

Ser Glu Val Glu Met Leu Ser Ser Gln Glu Arg Met Lys Val Gln Gly
                500                 505                 510

Ser Pro Leu Lys Lys Leu Phe Thr Ser Thr Gly Leu Lys Lys Leu Ser
        515                 520                 525

Gly Lys Lys Gln Lys Gly Lys Arg Gly Gly Asp Glu Glu Ser Gly
        530                 535                 540

Glu His Thr Gln Val Pro Ala Asp Ser Pro Asp Ser Gln Glu Glu Gln
545                 550                 555                 560

Lys Gly Glu Ser Ser Ala Ser Ser Pro Glu Glu Pro Glu Glu Ile Thr
                565                 570                 575

Cys Leu Glu Lys Gly Leu Ala Glu Val Gln Gln Asp Gly Glu Ala Glu
                580                 585                 590

Glu Gly Ala Thr Ser Asp Gly Glu Lys Lys Arg Glu Gly Val Thr Pro
                595                 600                 605

Trp Ala Ser Phe Lys Lys Met Val Thr Pro Lys Lys Arg Val Arg Arg
        610                 615                 620

Pro Ser Glu Ser Asp Lys Glu Asp Glu Leu Asp Lys Val Lys Ser Ala
625                 630                 635                 640

Thr Leu Ser Ser Thr Glu Ser Thr Ala Ser Glu Met Gln Glu Met
                645                 650                 655

Lys Gly Ser Val Glu Glu Pro Lys Pro Glu Pro Lys Arg Lys Val
                660                 665                 670

Asp Thr Ser Val Ser Trp Glu Ala Leu Ile Cys Val Gly Ser Ser Lys
                675                 680                 685

Lys Arg Ala Arg Arg Arg Ser Ser Ser Asp Glu Glu Gly Gly Pro Lys
```

-continued

```
            690                 695                 700
Ala Met Gly Gly Asp His Gln Lys Ala Asp Glu Ala Gly Lys Asp Lys
705                 710                 715                 720

Glu Thr Gly Thr Asp Gly Ile Leu Ala Gly Ser Gln Glu His Asp Pro
                725                 730                 735

Gly Gln Gly Ser Ser Ser Pro Glu Gln Ala Gly Ser Pro Thr Glu Gly
            740                 745                 750

Glu Gly Val Ser Thr Trp Glu Ser Phe Lys Arg Leu Val Thr Pro Arg
            755                 760                 765

Lys Lys Ser Lys Ser Lys Leu Glu Glu Lys Ser Glu Asp Ser Ile Ala
770                 775                 780

Gly Ser Gly Val Glu His Ser Thr Pro Asp Thr Glu Pro Gly Lys Glu
785                 790                 795                 800

Glu Ser Trp Val Ser Ile Lys Lys Phe Ile Pro Gly Arg Arg Lys Lys
                805                 810                 815

Arg Pro Asp Gly Lys Gln Glu Gln Ala Pro Val Glu Asp Ala Gly Pro
            820                 825                 830

Thr Gly Ala Asn Glu Asp Asp Ser Asp Val Pro Ala Val Val Pro Leu
            835                 840                 845

Ser Glu Tyr Asp Ala Val Glu Arg Glu Lys Met Glu Ala Gln Gln Ala
850                 855                 860

Gln Lys Gly Ala Glu Gln Pro Glu Gln Lys Ala Ala Thr Glu Val Ser
865                 870                 875                 880

Lys Glu Leu Ser Glu Ser Gln Val His Met Met Ala Ala Ala Val Ala
                885                 890                 895

Asp Gly Thr Arg Ala Ala Thr Ile Ile Glu Glu Arg Ser Pro Ser Trp
            900                 905                 910

Ile Ser Ala Ser Val Thr Glu Pro Leu Glu Gln Val Glu Ala Glu Ala
            915                 920                 925

Ala Leu Leu Thr Glu Glu Val Leu Glu Arg Glu Val Ile Ala Glu Glu
            930                 935                 940

Glu Pro Pro Thr Val Thr Glu Pro Leu Pro Glu Asn Arg Glu Ala Arg
945                 950                 955                 960

Gly Asp Thr Val Val Ser Glu Ala Glu Leu Thr Pro Glu Ala Val Thr
                965                 970                 975

Ala Ala Glu Thr Ala Gly Pro Leu Gly Ser Glu Glu Gly Thr Glu Ala
            980                 985                 990

Ser Ala Ala Glu Glu Thr Thr Glu Met Val Ser Ala Val Ser Gln Leu
            995                 1000                1005

Thr Asp Ser Pro Asp Thr Thr Glu Glu Ala Thr Pro Val Gln Glu Val
   1010                 1015                1020

Glu Gly Gly Val Pro Asp Ile Glu Glu Gln Glu Arg Arg Thr Gln Glu
1025                1030                1035                1040

Val Leu Gln Ala Val Ala Glu Lys Val Lys Glu Glu Ser Gln Leu Pro
                1045                1050                1055

Gly Thr Gly Gly Pro Glu Asp Val Leu Gln Pro Val Gln Arg Ala Glu
            1060                1065                1070

Ala Glu Arg Pro Glu Glu Gln Ala Glu Ala Ser Gly Leu Lys Lys Glu
            1075                1080                1085

Thr Asp Val Val Leu Lys Val Asp Ala Gln Glu Ala Lys Thr Glu Pro
    1090                1095                1100

Phe Thr Gln Gly Lys Val Val Gly Gln Thr Thr Pro Glu Ser Phe Glu
1105                1110                1115                1120
```

-continued

Lys Ala Pro Gln Val Thr Glu Ser Ile Glu Ser Ser Glu Leu Val Thr
                1125                1130                1135

Thr Cys Gln Ala Glu Thr Leu Ala Gly Val Lys Ser Gln Glu Met Val
                1140                1145                1150

Met Glu Gln Ala Ile Pro Pro Asp Ser Val Glu Thr Pro Thr Asp Ser
                1155                1160                1165

Glu Thr Asp Gly Ser Thr Pro Val Ala Asp Phe Asp Ala Pro Gly Thr
       1170                1175                1180

Thr Gln Lys Asp Glu Ile Val Glu Ile His Glu Glu Asn Glu Val Ala
1185                1190                1195                1200

Ser Gly Thr Gln Ser Gly Gly Thr Glu Ala Glu Ala Val Pro Ala Gln
                1205                1210                1215

Lys Glu Arg Pro Pro Ala Pro Ser Ser Phe Val Phe Gln Glu Glu Thr
                1220                1225                1230

Lys Glu Gln Ser Lys Met Glu Asp Thr Leu Glu His Thr Asp Lys Glu
                1235                1240                1245

Val Ser Val Glu Thr Val Ser Ile Leu Ser Lys Thr Glu Gly Thr Gln
       1250                1255                1260

Glu Ala Asp Gln Tyr Ala Asp Glu Lys Thr Lys Asp Val Pro Phe Phe
1265                1270                1275                1280

Glu Gly Leu Glu Gly Ser Ile Asp Thr Gly Ile Thr Val Ser Arg Glu
                1285                1290                1295

Lys Val Thr Glu Val Ala Leu Lys Gly Glu Gly Thr Glu Glu Ala Glu
                1300                1305                1310

Cys Lys Lys Asp Asp Ala Leu Glu Leu Gln Ser His Ala Lys Ser Pro
       1315                1320                1325

Pro Ser Pro Val Glu Arg Glu Met Val Val Gln Val Glu Arg Glu Lys
       1330                1335                1340

Thr Glu Ala Glu Pro Thr His Val Asn Glu Glu Lys Leu Glu His Glu
1345                1350                1355                1360

Thr Ala Val Thr Val Ser Glu Glu Val Ser Lys Gln Leu Leu Gln Thr
                1365                1370                1375

Val Asn Val Pro Ile Ile Asp Gly Ala Lys Glu Val Ser Ser Leu Glu
                1380                1385                1390

Gly Ser Pro Pro Pro Cys Leu Gly Gln Glu Glu Ala Val Cys Thr Lys
       1395                1400                1405

Ile Gln Val Gln Ser Ser Glu Ala Ser Phe Thr Leu Thr Ala Ala Ala
       1410                1415                1420

Glu Glu Glu Lys Val Leu Gly Glu Thr Ala Asn Ile Leu Glu Thr Gly
1425                1430                1435                1440

Glu Thr Leu Glu Pro Ala Gly Ala His Leu Val Leu Glu Glu Lys Ser
                1445                1450                1455

Ser Glu Lys Asn Glu Asp Phe Ala Ala His Pro Gly Glu Asp Ala Val
                1460                1465                1470

Pro Thr Gly Pro Asp Cys Gln Ala Lys Ser Thr Pro Val Ile Val Ser
       1475                1480                1485

Ala Thr Thr Lys Lys Gly Leu Ser Ser Asp Leu Glu Gly Glu Lys Thr
       1490                1495                1500

Thr Ser Leu Lys Trp Lys Ser Asp Glu Val Asp Glu Gln Val Ala Cys
1505                1510                1515                1520

Gln Glu Val Lys Val Ser Val Ala Ile Glu Asp Leu Glu Pro Glu Asn
                1525                1530                1535

-continued

```
Gly Ile Leu Glu Leu Glu Thr Lys Ser Ser Lys Leu Val Gln Asn Ile
            1540                1545                1550
Ile Gln Thr Ala Val Asp Gln Phe Val Arg Thr Glu Glu Thr Ala Thr
        1555                1560                1565
Glu Met Leu Thr Ser Glu Leu Gln Thr Gln Ala His Val Ile Lys Ala
    1570                1575                1580
Asp Ser Gln Asp Ala Gly Gln Glu Thr Glu Lys Glu Gly Glu Pro
1585                1590                1595                1600
Gln Ala Ser Ala Gln Asp Glu Thr Pro Ile Thr Ser Ala Lys Glu Glu
            1605                1610                1615
Ser Glu Ser Thr Ala Val Gly Gln Ala His Ser Asp Ile Ser Lys Asp
        1620                1625                1630
Met Ser Glu Ala Ser Glu Lys Thr Met Thr Val Glu Val Glu Gly Ser
    1635                1640                1645
Thr Val Asn Asp Gln Gln Leu Glu Glu Val Val Leu Pro Ser Glu Glu
1650                1655                1660
Glu Gly Gly Gly Ala Gly Thr Lys Ser Val Pro Glu Asp Asp Gly His
1665                1670                1675                1680
Ala Leu Leu Ala Glu Arg Ile Glu Lys Ser Leu Val Glu Pro Lys Glu
            1685                1690                1695
Asp Glu Lys Gly Asp Asp Val Asp Asp Pro Glu Asn Gln Asn Ser Ala
        1700                1705                1710
Leu Ala Asp Thr Asp Ala Ser Gly Gly Leu Thr Lys Glu Ser Pro Asp
    1715                1720                1725
Thr Asn Gly Pro Lys Gln Lys Glu Lys Glu Asp Ala Gln Glu Val Glu
1730                1735                1740
Leu Gln Glu Gly Lys Val His Ser Glu Ser Asp Lys Ala Ile Thr Pro
1745                1750                1755                1760
Gln Ala Gln Glu Glu Leu Gln Lys Gln Glu Arg Glu Ser Ala Lys Ser
            1765                1770                1775
Glu Leu Thr Glu Ser
        1780
```

```
<210> SEQ ID NO 14
<211> LENGTH: 1247
<212> TYPE: PRT
<213> ORGANISM: Homo sapiens

<400> SEQUENCE: 14

Met Leu Ala Ser Ser Arg Ile Arg Ala Ala Trp Thr Arg Ala Leu
1                5                10                15
Leu Leu Pro Leu Leu Leu Ala Gly Pro Val Gly Cys Leu Ser Arg Gln
            20                25                30
Glu Leu Phe Pro Phe Gly Pro Gly Gln Gly Asp Leu Glu Leu Glu Asp
        35                40                45
Gly Asp Asp Phe Val Ser Pro Ala Leu Glu Leu Ser Gly Ala Leu Arg
    50                55                60
Phe Tyr Asp Arg Ser Asp Ile Asp Ala Val Tyr Val Thr Thr Asn Gly
65                70                75                80
Ile Ile Ala Thr Ser Glu Pro Pro Ala Lys Glu Ser His Pro Gly Leu
            85                90                95
Phe Pro Pro Thr Phe Gly Ala Val Ala Pro Phe Leu Ala Asp Leu Asp
        100                105                110
Thr Thr Asp Gly Leu Gly Lys Val Tyr Tyr Arg Glu Asp Leu Ser Pro
    115                120                125
```

-continued

```
Ser Ile Thr Gln Arg Ala Ala Glu Cys Val His Arg Gly Phe Pro Glu
130                 135                 140
Ile Ser Phe Gln Pro Ser Ser Ala Val Val Thr Trp Glu Ser Val
145                 150                 155                 160
Ala Pro Tyr Gln Gly Pro Ser Arg Asp Pro Asp Gln Lys Gly Lys Arg
                    165                 170                 175
Asn Thr Phe Gln Ala Val Leu Ala Ser Ser Asp Ser Ser Ser Tyr Ala
                180                 185                 190
Ile Phe Leu Tyr Pro Glu Asp Gly Leu Gln Phe His Thr Thr Phe Ser
            195                 200                 205
Lys Lys Glu Asn Asn Gln Val Pro Ala Val Val Ala Phe Ser Gln Gly
        210                 215                 220
Ser Val Gly Phe Leu Trp Lys Ser Asn Gly Ala Tyr Asn Ile Phe Ala
225                 230                 235                 240
Asn Asp Arg Glu Ser Ile Glu Asn Leu Ala Lys Ser Ser Asn Ser Gly
                245                 250                 255
Gln Gln Gly Val Trp Val Phe Glu Ile Gly Ser Pro Ala Thr Thr Asn
            260                 265                 270
Gly Val Val Pro Ala Asp Val Ile Leu Gly Thr Glu Asp Gly Ala Glu
        275                 280                 285
Tyr Asp Asp Glu Asp Glu Asp Tyr Asp Leu Ala Thr Thr Arg Leu Gly
290                 295                 300
Leu Glu Asp Val Gly Thr Thr Pro Phe Ser Tyr Lys Ala Leu Arg Arg
305                 310                 315                 320
Gly Gly Ala Asp Thr Tyr Ser Val Pro Ser Val Leu Ser Pro Arg Arg
                325                 330                 335
Ala Ala Thr Glu Arg Pro Leu Gly Pro Pro Thr Glu Arg Thr Arg Ser
            340                 345                 350
Phe Gln Leu Ala Val Glu Thr Phe His Gln Gln His Pro Gln Val Ile
        355                 360                 365
Asp Val Asp Glu Val Glu Glu Thr Gly Val Val Phe Ser Tyr Asn Thr
370                 375                 380
Asp Ser Arg Gln Thr Cys Ala Asn Asn Arg His Gln Cys Ser Val His
385                 390                 395                 400
Ala Glu Cys Arg Asp Tyr Ala Thr Gly Phe Cys Cys Ser Cys Val Ala
                405                 410                 415
Gly Tyr Thr Gly Asn Gly Arg Gln Cys Val Ala Glu Gly Ser Pro Gln
            420                 425                 430
Arg Val Asn Gly Lys Val Lys Gly Arg Ile Phe Val Gly Ser Ser Gln
        435                 440                 445
Val Pro Ile Val Phe Glu Asn Thr Asp Leu His Ser Tyr Val Val Met
450                 455                 460
Asn His Gly Arg Ser Tyr Thr Ala Ile Ser Thr Ile Pro Glu Thr Val
465                 470                 475                 480
Gly Tyr Ser Leu Leu Pro Leu Ala Pro Val Gly Gly Ile Ile Gly Trp
                485                 490                 495
Met Phe Ala Val Glu Gln Asp Gly Phe Lys Asn Gly Phe Ser Ile Thr
            500                 505                 510
Gly Gly Glu Phe Thr Arg Gln Ala Glu Val Thr Phe Val Gly His Pro
        515                 520                 525
Gly Asn Leu Val Ile Lys Gln Arg Phe Ser Gly Ile Asp Glu His Gly
530                 535                 540
```

-continued

```
His Leu Thr Ile Asp Thr Glu Leu Glu Gly Arg Val Pro Gln Ile Pro
545                 550                 555                 560

Phe Gly Ser Ser Val His Ile Glu Pro Tyr Thr Glu Leu Tyr His Tyr
                565                 570                 575

Ser Thr Ser Val Ile Thr Ser Ser Thr Arg Glu Tyr Thr Val Thr
            580                 585                 590

Glu Pro Glu Arg Asp Gly Ala Ser Pro Ser Arg Ile Tyr Thr Tyr Gln
                595                 600                 605

Trp Arg Gln Thr Ile Thr Phe Gln Glu Cys Val His Asp Asp Ser Arg
610                 615                 620

Pro Ala Leu Pro Ser Thr Gln Gln Leu Ser Val Asp Ser Val Phe Val
625                 630                 635                 640

Leu Tyr Asn Gln Glu Glu Lys Ile Leu Arg Tyr Ala Phe Ser Asn Ser
                645                 650                 655

Ile Gly Pro Val Arg Glu Gly Ser Pro Asp Ala Leu Gln Asn Pro Cys
                660                 665                 670

Tyr Ile Gly Thr His Gly Cys Asp Thr Asn Ala Ala Cys Arg Pro Gly
                675                 680                 685

Pro Arg Thr Gln Phe Thr Cys Glu Cys Ser Ile Gly Phe Arg Gly Asp
                690                 695                 700

Gly Arg Thr Cys Tyr Asp Ile Asp Glu Cys Ser Glu Gln Pro Ser Val
705                 710                 715                 720

Cys Gly Ser His Thr Ile Cys Asn Asn His Pro Gly Thr Phe Arg Cys
                725                 730                 735

Glu Cys Val Glu Gly Tyr Gln Phe Ser Asp Glu Gly Thr Cys Val Ala
                740                 745                 750

Val Val Asp Gln Arg Pro Ile Asn Tyr Cys Glu Thr Gly Leu His Asn
                755                 760                 765

Cys Asp Ile Pro Gln Arg Ala Gln Cys Ile Tyr Thr Gly Gly Ser Ser
770                 775                 780

Tyr Thr Cys Ser Cys Leu Pro Gly Phe Ser Gly Asp Gly Gln Ala Cys
785                 790                 795                 800

Gln Asp Val Asp Glu Cys Gln Pro Ser Arg Cys His Pro Asp Ala Phe
                805                 810                 815

Cys Tyr Asn Thr Pro Gly Ser Phe Thr Cys Gln Cys Lys Pro Gly Tyr
                820                 825                 830

Gln Gly Asp Gly Phe Arg Cys Val Pro Gly Glu Val Glu Lys Thr Arg
                835                 840                 845

Cys Gln His Glu Arg Glu His Ile Leu Gly Ala Ala Gly Ala Thr Asp
850                 855                 860

Pro Gln Arg Pro Ile Pro Pro Gly Leu Phe Val Pro Glu Cys Asp Ala
865                 870                 875                 880

His Gly His Tyr Ala Pro Thr Gln Cys His Gly Ser Thr Gly Tyr Cys
                885                 890                 895

Trp Cys Val Asp Arg Asp Gly Arg Glu Val Glu Gly Thr Arg Thr Arg
                900                 905                 910

Pro Gly Met Thr Pro Pro Cys Leu Ser Thr Val Ala Pro Pro Ile His
                915                 920                 925

Gln Gly Pro Ala Val Pro Thr Ala Val Ile Pro Leu Pro Pro Gly Thr
                930                 935                 940

His Leu Leu Phe Ala Gln Thr Gly Lys Ile Glu Arg Leu Pro Leu Glu
945                 950                 955                 960

Gly Asn Thr Met Arg Lys Thr Glu Ala Lys Ala Phe Leu His Val Pro
```

-continued

Ala Lys Val Ile Ile Gly Leu Ala Phe Asp Cys Val Asp Lys Met Val
        965                 970                 975
                    980                 985                 990

Tyr Trp Thr Asp Ile Thr Glu Pro Ser Ile Gly Arg Ala Ser Leu His
        995                 1000                1005

Gly Gly Glu Pro Thr Thr Ile Ile Arg Gln Asp Leu Gly Ser Pro Glu
    1010                1015                1020

Gly Ile Ala Val Asp His Leu Gly Arg Asn Ile Phe Trp Thr Asp Ser
1025                1030                1035                1040

Asn Leu Asp Arg Ile Glu Val Ala Lys Leu Asp Gly Thr Gln Arg Arg
                1045                1050                1055

Val Leu Phe Glu Thr Asp Leu Val Asn Pro Arg Gly Ile Val Thr Asp
            1060                1065                1070

Ser Val Arg Gly Asn Leu Tyr Trp Thr Asp Trp Asn Arg Asp Asn Pro
        1075                1080                1085

Lys Ile Glu Thr Ser Tyr Met Asp Gly Thr Asn Arg Arg Ile Leu Val
    1090                1095                1100

Gln Asp Asp Leu Gly Leu Pro Asn Gly Leu His Phe Asp Ala Phe Ser
1105                1110                1115                1120

Ser Gln Leu Cys Trp Val Asp Ala Gly Thr Asn Arg Ala Glu Cys Leu
                1125                1130                1135

Asn Pro Ser Gln Pro Ser Arg Arg Lys Ala Leu Glu Gly Leu Gln Tyr
            1140                1145                1150

Pro Phe Ala Val Thr Ser Tyr Gly Lys Asn Leu Tyr Phe Thr Asp Trp
        1155                1160                1165

Lys Met Asn Ser Val Val Ala Leu Asp Leu Ala Ile Ser Lys Glu Thr
    1170                1175                1180

Asp Ala Phe Gln Pro His Lys Gln Thr Arg Leu Tyr Gly Ile Thr Thr
1185                1190                1195                1200

Ala Leu Ser Gln Cys Pro Gln Gly His Asn Tyr Cys Ser Val Asn Asn
                1205                1210                1215

Gly Gly Cys Thr His Leu Cys Leu Ala Thr Pro Gly Ser Arg Thr Cys
            1220                1225                1230

Arg Cys Pro Asp Asn Thr Leu Gly Val Asp Cys Ile Glu Arg Lys
        1235                1240                1245

<210> SEQ ID NO 15
<211> LENGTH: 997
<212> TYPE: PRT
<213> ORGANISM: Homo sapiens

<400> SEQUENCE: 15

Met Pro Ser Glu Lys Lys Ile Ser Ser Ala Asn Asp Cys Ile Ser Phe
1               5                   10                  15

Met Gln Ala Gly Cys Glu Leu Lys Lys Val Arg Pro Asn Ser Arg Ile
            20                  25                  30

Tyr Asn Arg Phe Phe Thr Leu Asp Thr Asp Leu Gln Ala Leu Arg Trp
        35                  40                  45

Glu Pro Ser Lys Lys Asp Leu Glu Lys Ala Lys Leu Asp Ile Ser Ala
    50                  55                  60

Ile Lys Glu Ile Arg Leu Gly Lys Asn Thr Glu Thr Phe Thr Asn Asn
65                  70                  75                  80

Gly Leu Ala Asp Gln Ile Cys Glu Asp Cys Ala Phe Ser Ile Leu His
            85                  90                  95

-continued

```
Gly Glu Asn Tyr Glu Ser Leu Asp Leu Val Ala Asn Ser Ala Asp Val
            100                 105                 110

Ala Asn Ile Trp Val Ser Gly Leu Arg Tyr Leu Val Ser Arg Ser Lys
            115                 120                 125

Gln Pro Leu Asp Phe Met Glu Gly Asn Gln Asn Thr Pro Arg Phe Met
130                 135                 140

Trp Leu Lys Thr Val Phe Glu Ala Ala Asp Val Asp Gly Asn Gly Ile
145                 150                 155                 160

Met Leu Glu Asp Thr Ser Val Glu Leu Ile Lys Gln Leu Asn Pro Thr
                165                 170                 175

Leu Lys Glu Ala Lys Ile Arg Leu Lys Phe Lys Glu Ile Gln Lys Ser
            180                 185                 190

Lys Glu Lys Leu Thr Thr Arg Val Thr Glu Glu Phe Cys Glu Ala
            195                 200                 205

Phe Cys Glu Leu Cys Thr Arg Pro Glu Val Tyr Phe Leu Leu Val Gln
    210                 215                 220

Ile Ser Lys Asn Lys Glu Tyr Leu Asp Ala Asn Asp Leu Met Leu Phe
225                 230                 235                 240

Leu Glu Ala Glu Gln Gly Val Thr His Ile Thr Glu Asp Ile Cys Leu
                245                 250                 255

Asp Ile Ile Arg Arg Tyr Glu Leu Ser Glu Glu Gly Arg Gln Lys Gly
            260                 265                 270

Phe Leu Ala Ile Asp Gly Phe Thr Gln Tyr Leu Leu Ser Ser Glu Cys
            275                 280                 285

Asp Ile Phe Asp Pro Glu Gln Lys Lys Val Ala Gln Asp Met Thr Gln
290                 295                 300

Pro Leu Ser His Tyr Tyr Ile Asn Ala Ser His Asn Thr Tyr Leu Ile
305                 310                 315                 320

Glu Asp Gln Phe Arg Gly Pro Ala Asp Ile Asn Gly Tyr Ile Arg Ala
                325                 330                 335

Leu Lys Met Gly Cys Arg Ser Val Glu Leu Asp Val Ser Asp Gly Ser
            340                 345                 350

Asp Asn Glu Pro Ile Leu Cys Asn Arg Asn Asn Met Thr Thr His Val
            355                 360                 365

Ser Phe Arg Ser Val Ile Glu Val Ile Asn Lys Phe Ala Phe Val Ala
370                 375                 380

Ser Glu Tyr Pro Leu Ile Leu Cys Leu Gly Asn His Cys Ser Leu Pro
385                 390                 395                 400

Gln Gln Lys Val Met Ala Gln Met Lys Lys Val Phe Gly Asn Lys
            405                 410                 415

Leu Tyr Thr Glu Ala Pro Leu Pro Ser Glu Ser Tyr Leu Pro Ser Pro
            420                 425                 430

Glu Lys Leu Lys Arg Met Ile Ile Val Lys Gly Lys Lys Leu Pro Ser
            435                 440                 445

Asp Pro Asp Val Leu Glu Gly Glu Val Thr Asp Glu Asp Glu Glu Ala
450                 455                 460

Gln Met Ser Arg Arg Met Ser Val Asp Tyr Asn Gly Glu Gln Lys Gln
465                 470                 475                 480

Ile Arg Leu Cys Arg Glu Leu Ser Asp Leu Val Ser Ile Cys Lys Ser
            485                 490                 495

Val Gln Tyr Arg Asp Phe Glu Leu Ser Met Lys Ser Gln Asn Tyr Trp
            500                 505                 510

Glu Met Cys Ser Phe Ser Glu Thr Glu Ala Ser Arg Ile Ala Asn Glu
```

-continued

```
                515                 520                 525
Tyr Pro Glu Asp Phe Val Asn Tyr Asn Lys Lys Phe Leu Ser Arg Ile
        530                 535                 540
Tyr Pro Ser Ala Met Arg Ile Asp Ser Ser Asn Leu Asn Pro Gln Asp
545                 550                 555                 560
Phe Trp Asn Cys Gly Cys Gln Ile Val Ala Met Asn Phe Gln Thr Pro
                565                 570                 575
Gly Pro Met Met Asp Leu His Thr Gly Trp Phe Leu Gln Asn Gly Gly
                580                 585                 590
Cys Gly Tyr Val Leu Arg Pro Ser Ile Met Arg Asp Glu Val Ser Tyr
        595                 600                 605
Phe Ser Ala Asn Thr Lys Gly Ile Leu Pro Gly Val Ser Pro Leu Ala
        610                 615                 620
Leu His Ile Lys Ile Ile Ser Gly Gln Asn Phe Pro Lys Pro Lys Gly
625                 630                 635                 640
Ala Cys Ala Lys Gly Asp Val Ile Asp Pro Tyr Val Cys Ile Glu Ile
                645                 650                 655
His Gly Ile Pro Ala Asp Cys Ser Glu Gln Arg Thr Lys Thr Val Gln
                660                 665                 670
Gln Asn Ser Asp Asn Pro Ile Phe Asp Glu Thr Phe Glu Phe Gln Val
        675                 680                 685
Asn Leu Pro Glu Leu Ala Met Ile Arg Phe Val Val Leu Asp Asp Asp
        690                 695                 700
Tyr Ile Gly Asp Glu Phe Ile Gly Gln Tyr Thr Ile Pro Phe Glu Cys
705                 710                 715                 720
Leu Gln Pro Gly Tyr Arg His Val Pro Leu Arg Ser Phe Val Gly Asp
                725                 730                 735
Ile Met Glu His Val Thr Leu Phe Val His Ile Ala Ile Thr Asn Arg
                740                 745                 750
Ser Gly Gly Gly Lys Ala Gln Lys Arg Ser Leu Ser Val Arg Met Gly
        755                 760                 765
Lys Lys Val Arg Glu Tyr Thr Met Leu Arg Asn Ile Gly Leu Lys Thr
        770                 775                 780
Ile Asp Asp Ile Phe Lys Ile Ala Val His Pro Leu Arg Glu Ala Ile
785                 790                 795                 800
Asp Met Arg Glu Asn Met Gln Asn Ala Ile Val Ser Ile Lys Glu Leu
                805                 810                 815
Cys Gly Leu Pro Pro Ile Ala Ser Leu Lys Gln Cys Leu Leu Thr Leu
                820                 825                 830
Ser Ser Arg Leu Ile Thr Ser Asp Asn Thr Pro Ser Val Ser Leu Val
        835                 840                 845
Met Lys Asp Ser Phe Pro Tyr Leu Glu Pro Leu Gly Ala Ile Pro Asp
        850                 855                 860
Val Gln Lys Lys Met Leu Thr Ala Tyr Asp Leu Met Ile Gln Glu Ser
865                 870                 875                 880
Arg Phe Leu Ile Glu Met Ala Asp Thr Val Gln Glu Lys Ile Val Gln
                885                 890                 895
Cys Gln Lys Ala Gly Met Glu Phe His Glu Leu His Asn Leu Gly
                900                 905                 910
Ala Lys Glu Gly Leu Lys Gly Arg Lys Leu Asn Lys Ala Thr Glu Ser
        915                 920                 925
Phe Ala Trp Asn Ile Thr Val Leu Lys Gly Gln Gly Asp Leu Leu Lys
        930                 935                 940
```

```
Asn Ala Lys Asn Glu Ala Ile Glu Asn Met Lys Gln Ile Gln Leu Ala
945                 950                 955                 960

Cys Leu Ser Cys Gly Leu Ser Lys Ala Pro Ser Ser Ser Ala Glu Ala
                965                 970                 975

Lys Ser Lys Arg Ser Leu Glu Ala Ile Glu Glu Lys Glu Ser Ser Glu
                980                 985                 990

Glu Asn Gly Lys Leu
            995
```

METHOD FOR IN VITRO DIAGNOSIS OF ENDOMETRIOSIS

This application claims the benefit of the filing date of U.S. Provisional Application Serial No. 60/243,265 filed Oct. 26, 2000.

The invention relates to a method for in vitro diagnosis of endometriosis.

Endometriosis is one of the most frequently occurring gynecological diseases, by which roughly 5–10% of all women of child-bearing age are affected (Sillem, M. 1998; Programmed(R) 23, Suppl. 1, 1–28). It is characterized by the occurrence of endometrial tissue outside of the physiological mucous membrane lining of the uterus. In addition to pain and numerous other symptoms, many endometriosis patients are sterile, and a large portion of IVF patients (IVF=in vitro fertilization) suffer from endometriosis (Adamson, G. D. 1997; Sem. Reprod. Biol. 15, 263–271). Very recently, publications that speak for a genetic predisposition in the development of an endometriosis have been multiplying (Kennedy, S. 1997; Sem. Reprod. Biol. 15, 309–318). The loss of tumor suppressor molecules and family clusters in the case of endometriosis patients was thus described.

Endometriosis is currently diagnosed with the aid of laparoscopy. This is an invasive method, which frequently results in complications (Chapron, C. et al. 1998; Hum. Reprod. 13, 867–872; Jansen, F. W. et al., 1997; Br. J. Obstet. Gynecol. 104, 595–600). It is performed under anesthesia and requires a fully set-up operating room.

There is therefore a need for new diagnostic methods. A method that would impose less of a burden for the patients and that could be performed by the attending physician would be desirable.

This problem is achieved according to the invention by the identification of genes that are differentially regulated in endometriosis and the preparation of a method for detection of their gene products.

The invention relates to a method for in vitro diagnosis of endometriosis, whereby the amount of gene product of at least one gene from the group that consists of fibronectin, insulin-like growth factor binding protein-2, transmembrane receptor PTK7, platelet-derived growth factor receptor alpha, collagen type XVIII alpha 1, subtilisin-like protein (PACE4), laminin M chain (merosin), elastin, collagen type IV alpha 2, p27 interferon alpha-inducible gene, reticulocalbin, aldehyde dehydrogenase 6, gravin, nidogen and phospholipase C epsilon is determined in a patient sample and is compared to the amount of this gene product in a control sample, whereby a smaller amount of this gene product indicates the presence of an endometriosis.

The group of genes is described in more detail in FIG. 1. The expression strength, i.e., the amount of gene product, is determined by at least one of the genes in a patient sample that is mentioned in FIGS. 1a and 1b and compared to that of a control sample (women without endometriosis). The samples that are to be compared must both originate from the secretory phase, thus from the range of days 15–28 after the last menstruation. A decreased expression strength of at least one of the above-mentioned genes in the patient sample indicates the presence of an endometriosis.

A patient sample can be a sample from endometrial tissue, peritoneal fluid, blood, vaginal secretion or urine of the patient.

A gene product is either mRNA, the cDNA that is derived therefrom, a polypeptide or portions of a polypeptide. The amino acid sequences of the polypeptides are depicted in FIGS. 2a–m.

The methods according to the invention can be used for first-time diagnosis of endometriosis. In this case, the amount of the gene product in the patient sample is compared to a control sample of undiseased women. The method according to the invention can also be used to evaluate the course of the disease. Thus, e.g., the success of a therapy can be determined. In this case, the patient sample is compared to a prior sample from the same patient.

The gene product polypeptide or a segment of a polypeptide is detected by immunoassay. To this end, specific antibodies are produced using one or more polypeptides that are selected from the group that is described in FIGS. 2a–m. The antibodies can be monoclonal or polyclonal. They can be directed against respectively the entire polypeptide or against fragments thereof. Such an antibody is obtained according to standard methods by immunization of test animals. The antibodies are then used in, e.g., an ELISA (enzyme-linked-immunosorbent assay), in an RIA (radioimmunoassay) or in the immunohistochemistry for determining the amount of the gene product (Aoki, K. et al. 1996; Forensic Sci. Int. 80, 163–173).

The invention further relates to the use of an antibody chip according to the invention for diagnosis of endometriosis. Antibody chips are miniaturized vehicles, in most cases made of glass or silicon, on whose surface antibodies of known specificity are immobilized in an ordered grid of high density. The detection of the protein/protein interactions can be carried out by mass spectrometry, fluorescence or surface plasmon resonance. Antibodies that specifically bind the proteins that are selected from the group that is described in FIGS. 2a–m can be immobilized on the antibody chip. Methods for the production and use of antibody chips are described in Kreider BL, Med Res Rev 2000, 20:212–215.

The mRNA gene products or the cDNA derived therefrom can be determined by hybridization with oligonucleotides, e.g., by a Northern Blot. These oligonucleotides have sequences that are complementary to partial sequences of the gene product that is to be detected and can be labeled with, e.g., a chromogenic, radioactive or fluorescent group. Before hybridization, the cDNA can be amplified with the aid of PCR (Sambrook, J. et al. 1989; Cold Spring Harbor Laboratory Press).

The mRNA gene products or the cDNA derived therefrom can also be determined by quantitative PCR (polymerase chain reaction).

The mRNA can also be determined by in situ hybridization with antisense-RNA. In this case, the antisense-RNA can be labeled with dioxigenin, $^{32}P$ or $^{33}P$. Antisense nucleic acid is a DNA and/or RNA, which is complementary to an mRNA. It can comprise the entire complementary sequence or partial sequences. This method is known to one skilled in the art (Barlati, S. et al. 1999; Histol. Histopathol. 14, 1231–1240).

The hybridization can also be carried out with the aid of a DNA chip. In addition, the invention therefore relates to a DNA chip, on which at least one oligonucleotide is immobilized, which corresponds to the complete cDNA sequence or a partial sequence or a complementary sequence of a gene that is selected from the group that is described in FIGS. 1a and 1b. The invention thus further relates to the use of a DNA chip according to the invention for diagnosis of endometriosis.

DNA chips, also known as DNA microarrays, are miniaturized vehicles, in most cases made of glass or silicon, on whose surface DNA molecules of known sequence are immobilized in an ordered grid of high density. The surface-bonded DNA molecules are hybridized with complementary, optionally labeled nucleic acids. The labeling can be a fluorescence dye.

In the case of oligonucleotide chips, the oligonucleotides that can be bonded to a DNA chip according to the invention represent partial sequences of the gene products (mRNA or cDNA derived therefrom) in the sense or antisense direction. One or more oligonucleotides per gene can be bonded to the DNA chip. Preferred are 25 nucleotide-long oligonucleotides, which are derived from the non-coding strand. The latter are preferably selected from the respective 3'-untranslated end of the gene. For detection, oligonucleotides of one gene, several genes or all genes that are selected from the group that is described in FIG. 1 can be used. Methods for the production and use of DNA chips are described in, e.g., U.S. Pat. Nos. 5,578,832, 5,556,752 and 5,510,270.

In the case of cDNA chips, the complete gene products (cDNAs) or subfragments (200–500 bp long) are bonded to the chip. The method is described in, e.g., Eckmann, L. et al., J. Biol. Chem. 2000, 275: 14084–14094.

The mRNA gene product can also be determined by chromogenic assays.

DESCRIPTION OF THE FIGURES

Various other features and attendant advantages of the present invention will be more fully appreciated as the same becomes better understood when considered in conjunction with the accompanying drawings, in which like reference characters designate the same or similar parts throughout the several views, and wherein:

FIGS. 1a and 1b shows the list of genes that can be adjusted downward in the secretory phase in the presence of an endometriosis and thus can be used for a diagnosis of the endometriosis. Listed in column 1 are the names and the data bank number (accession numbers) of the genes, which were found in analysis to be differentially regulated. In column 2 is found the comparison of samples from the secretory phase (secr. phase), in each case endometriosis versus normal (no endometriosis); down refers to the state of downward adjustment. The first number in parentheses indicates how often the gene was found to be regulated upward, and the second number indicates how often the gene was found to be adjusted downward. For this analysis, 20 individual comparisons were performed. In column 3, the comparison of samples from the proliferative phase (prol. phase) is found. For this analysis, 30 individual comparisons were performed. The designation down describes the same state as in column 1, nc means no correlation (no correlation), i.e., this gene is found to be regulated both downward and upward. The meaning of the numbers is analogous to column 2. In the fourth column, the comparison of samples from the secretory phase with samples from the proliferative phase is found. Here, the endometrium of women without endometriosis was compared to one another. For this analysis, 25 individual comparisons were performed. The designation up describes the state of the upward regulation. The meaning of the numbers is analogous to column 2.

FIGS. 2a–m show a list of polypeptides, which are coded by the genes that are depicted in FIGS. 1a and 1b and are expressed to a reduced extent in the presence of an endometriosis.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of U.S. Provisional Application Serial No. 60/243,265, filed Oct. 26, 2000 and German Application No. 100 48 633.9, filed Sept. 25, 2000, are hereby incorporated by reference.

EXAMPLES

The molecular-biological methods that are used in the examples, such as, e.g., isolation of RNA, sequencing of DNA, RNAse protection, Northern Blot analysis, polymerase-chain reaction (PCR) were performed according to standard protocols, as described in known textbooks, such as in, e.g., Molecular Cloning, A Laboratory Manual (Sambrook, J. et al. 1989; Cold Spring Harbor Laboratory Press). Methods for subtraction analyses of gene expression are described in, e.g., Liang, P. and Pardee, A. B. 1995; Curr. Opin. Immunol. 7, 274–280.

Example 1

Identification of Endometriosis-Associated Genes

Genes that are associated with the disease image of endometriosis were identified by comparison of endometrium samples of the following patient groups:

1. Proliferative phase: Days 4–14 after the last menstruation. This group consisted of patients in whom a hysteroscopy or hysterectomy was performed because of leiomyomas.
2. Secretory phase: Days 15–28 after the last menstruation. This group consisted of patients as described under 1.
3. Proliferative phase plus endometriosis: Days 4–14 after the last menstruation. The patients of this group suffered from endometriosis.
4. Secretory phase plus endometriosis: Days 15–28 after the last menstruation. The patients of this group suffered from endometriosis.

The endometrium of women with endometriosis was obtained by means of string curettage. The endometrium of the comparison group was obtained from women within the framework of a hysteroscopy or a hysterectomy, which was performed because of a leiomyoma. The tissue was deep-frozen after removal in liquid nitrogen. Then, whole-RNA was extracted from the samples. This RNA was amplified, labeled by a fluorescence marker, and hybridized with a DNA chip (human SL array of the Affymetrix Company that contains oligonucleotides for about 7000 human genes). After the hybridization process, the DNA chip was analyzed in a scanner. The hybridization patterns of all gene sequences, which are found on the chip, were compared between all samples. Altogether, 20 individual comparisons with samples from the secretory phase and 30 individual comparisons with samples from the proliferative phase were performed in which in each case a sample was supplied from a woman with endometriosis and a sample from a woman who did not suffer from endometriosis.

All the genes that were adjusted upward or downward in at least half of the cases (10 comparisons) by at least the factor 1.5 relative to the control group (samples of women without endometriosis) were considered to be differentially regulated. In addition, 25 individual comparisons of samples from the secretory phase were performed with samples from the proliferative phase. Here, the endometrium of women without endometriosis was compared.

The results are depicted in FIGS. 1a and b. The listed genes can be considered as differentiation markers. Assuming that the proliferative phase is dominated by the names according to proliferative processes, the secretory phase is more likely considered as a differentiation phase. Against this background, genes that are important to the differentiation should be regulated upward during this phase (cf. FIGS. 1a and b, column 4) and regulated downward or regulated to remain at the same level during the proliferative phase (cf. FIGS. 1a and b, column 3). The genes that are listed in column 1 meet these criteria and are therefore referred to as differentiation markers. The fact that these genes are adjusted downward in women with endometriosis (column 2) indicates a disrupted differentiation in the secretory phase.

Example 2

Diagnosis of Endometriosis

1. Sample Taking

For the DNA-chip analysis, endometrial tissue is obtained from patients and whole-RNA is isolated therefrom. The RNA is then amplified and coupled to a fluorescence marker. For the immune test, peritoneal fluid, blood, vaginal secretion, urine or endometrial tissue can be obtained from the patient.

2. Detection of Gene Products

2a. Using a DNA Chip

First, the suitable DNA sequences are determined from the genes that are selected from the group that is described in FIGS. 1a and b. Sequences that can hybridize with the selected gene transcripts are suitable. The oligonucleotides are then produced on the chip by a chemical process that is based on the photolithographic process. To this end, photolithographic masks are used, which were produced by suitable computer algorithms.

The labeled RNA is incubated with the chip in a hybridization furnace. The chip is then analyzed in a scanner, which determines the hybridization profile. As a result, it can be determined whether one or more of the genes of the genes listed in FIGS. 1a and b is regulated downward in the secretory phase, which indicates an endometriosis.

2b. By Immune Test

To perform an immune test, specific antibodies that bind to the polypeptides that are described in FIGS. 2a–m are required. The antibodies can be monoclonal or polyclonal antibodies, which are directed against the purified proteins, peptides, selected from the coded proteins, or recombinantly produced fragments or whole protein.

If the analysis is carried out by means of immunohistochemistry, the endometrium that was removed from the patient to be analysed is used. After suitable fixing of the tissue, e.g., by means of formaldehyde and subsequent embedding in paraffin, the tissue can be used for the immunohistochemical analysis. To this end, sections of suitable thickness, e.g., 4 μm, are prepared from the fixed and embedded tissue with a microtome. The specific antibody or antibodies are then incubated with the further prepared tissue sections (e.g., process of removing paraffin, blocks) for awhile under suitable temperature conditions, e.g., for one hour at room temperature. After washing steps are carried out with a suitable solution, e.g., PBS, the sections are incubated in a second step with a suitable second antibody that is, e.g., biotinylated for the subsequent reactions. The second antibody binds to the region of the first antibody that is constant for the respective species. After a suitable incubation time and washing steps, the tissue sample is now incubated in a third step with, e.g., horseradish peroxidase, coupled to streptavidin. After a suitable incubation time and washing steps, an enzyme reaction is now catalyzed in a last step by adding a suitable dye, e.g., DAB, from the peroxidase, which results in a color reaction where the first antibody specifically bonded. After the enzyme reaction and washing steps are stopped, the tissue section that is dried, fixed and provided with a cover glass can now be analyzed under the microscope. To decide whether a quantitative or else qualitative difference exists in the tissue sample, a corresponding control of a sample from a woman without endometriosis must be used as comparison.

If the analysis is done with Western Blots, the tissue samples or extracts that are obtained are separated from the peritoneal fluid, blood, vaginal secretion or urine by means of a polyacrylamide-gel electrophoresis. After the separation, the polypeptides that are separated in the gel are moved to a suitable carrier membrane, e.g., nitrocellulose, by application of an electric current. The proteins that are fixed to the carrier membrane are now incubated in a first step with the specific antibody or antibodies. After suitable washing processes with, e.g., TBS/TBST, the carrier membrane is incubated in a second step with a second antibody, which binds to the region of the first antibody that is constant for the respective species. The second antibody can carry a radioactive labelling or a coupled enzyme, e.g., alkaline phosphatase, which converts a colorless substrate into a colored substrate in a subsequent color reaction. Since the amount of the antigen is proportional to that of the second antibody that is bonded to the antigen, the amount of the measured dye can therefore be used for a quantitative analysis of the polypeptide or polypeptides that are present in the extract.

If the analysis is done with a solid-phase immunoassay, the specific antibody or antibodies are bonded to a polymer carrier matrix, e.g., polyvinyl chloride. The fixed antibody or antibodies are then incubated with the extract, which was obtained from, e.g., the peritoneal fluid, blood, vaginal secretion or urine. After suitable washing processes, a second antibody that specifically binds to another site of the antigen that is to be detected is added in a second step. The second antibody carries, e.g., a radioactive or fluorescence labeling and can therefore be detected in a highly sensitive manner in a third step. The amount of the second antibody that is bonded to the antigen is proportional to that of the antigen and can therefore be used for a quantitative analysis of the protein or proteins that are present in the extract.

If the analysis is done by means of ELISA (enzyme linked immunosorbent assay), the specific antibody or antibodies are bonded to a polymer carrier matrix, e.g., polyvinyl chloride. The fixed antibody or antibodies are then incubated with the extract, which was obtained from, e.g., the peritoneal fluid, blood, vaginal secretion or urine. After suitable washing processes, a second antibody is added in a second step, and said antibody specifically binds to another site of the antigen that is to be detected. In addition, the second antibody carries a coupled enzyme, e.g., an alkaline phosphatase. This enzyme now catalyzes in a subsequent step the conversion of a colorless substrate into a colored product. A non-fluorescent substrate can also be converted into a fluorescent substrate, however. The amount of colored or fluorescent product can be measured calorimetrically. Since the amount of the second antibody that is bonded to the antigen is proportional to that of the antigen, the amount of the measured dye or fluorescence product can therefore be used for a quantitative analysis of the polypeptide or polypeptides that are present in the extract.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method for in vitro diagnosis of endometriosis in a subject in need thereof, comprising:

determining the amount of gene product of at least one gene in an endometrial sample obtained during said subject's uterine secretory phase, wherein said gene is selected from: fibronectin, insulin-like growth factor binding protein-2, transmembrane receptor PTK7, platelet-derived growth factor receptor alpha, collagen type XVIII alpha 1, subtilisin-like protein (PACE4), laminin M chain (merosin), elastin, collagen type IV alpha 2, p27 interferon alpha-inducible gene, reticulocalbin, aldehyde dehydrogenase 6, gravin, nidogen, and phospholipase C epsilon, and comparing the amount of said gene product to a normal endometrial secretory phase control, whereby a smaller amount of said gene product in said subject's sample indicates the presence of an endometriosis.

2. A method of claim 1, wherein said determining is performed on a DNA chip comprising at least one oligonucleotide which corresponds to the complete cDNA sequence, a partial sequence thereof, or a complement thereof, selected from at least one said gene.

3. A method claim 1, wherein said DNA chip comprises at least one cDNA, or oligonucleotide thereof, corresponding to a gene selected from: insulin-like growth factor binding protein-2, transmembrane receptor PTK7, platelet-derived growth factor receptor alpha, collagen type XVIII alpha 1, subtilisin-like protein (PACE4), laminin M chain (merosin), elastin, collagen type IV alpha 2, p27 interferon alpha-inducible gene, reticulocalbin, aldehyde dehydrogenase 6, gravin, nidogen, phospholipase C epsilon, or a complement thereof.

4. A method of claim 1, wherein said determining is performed by polymerase chain reaction or Northern blot.

5. A method of claim 1, wherein said determining is performed on a plurality of said genes.

6. A method of claim 1, wherein said control is obtained from the same subject after therapy to evaluate the course of the disease.

7. A method for in vitro diagnosis of endometriosis in a subject in need thereof, comprising:

determining the amount of gene product of at least one gene in sample obtained during said subject's uterine secretory phase, wherein said gene is selected from: insulin-like growth factor binding protein-2, transmembrane receptor PTK7, platelet-derived growth factor receptor alpha, collagen type XVIII alpha 1, subtilisin-like protein (PACE4), laminin M chain (merosin), elastin, collagen type IV alpha 2, p27 interferon alpha-inducible gene, reticulocalbin, aldehyde dehydrogenase 6, gravin, nidogen, and phospholipase C epsilon, and comparing said amount of said gene product to a normal uterine secretory phase control, whereby a smaller amount of said gene product in said subject's sample indicates the presence of an endometriosis.

8. A method of claim 7, wherein said determining is performed on a DNA chip comprising at least one oligonucleotide which corresponds to the complete cDNA sequence, a partial sequence thereof, or a complement thereof, selected from at least one said gene.

9. A method of claim 7, wherein said determining is performed by polymerase chain reaction or Northern blot.

10. A method of claim 1, wherein said determining is performed on a plurality of said genes.

11. A method of claim 1, wherein said control is obtained from the same subject after therapy to evaluate the course of the disease.

* * * * *

UNITED STATES PATENT AND TRADEMARK OFFICE
CERTIFICATE OF CORRECTION

PATENT NO. : 6,780,594 B2
DATED : August 24, 2004
INVENTOR(S) : Hess-Stumpp et al.

It is certified that error appears in the above-identified patent and that said Letters Patent is hereby corrected as shown below:

<u>Title page,</u>
Item [75], Inventors, change "Berrholt Kreft, Berlin (DE)" to -- Bertolt Kreft, Berlin (DE) --.

Signed and Sealed this

Twenty-sixth Day of April, 2005

JON W. DUDAS
*Director of the United States Patent and Trademark Office*